United States Patent
Oft

(10) Patent No.: US 9,943,568 B2
(45) Date of Patent: Apr. 17, 2018

(54) METHODS OF USING PEGYLATED INTERLEUKIN-10 FOR TREATING CANCER

(71) Applicant: ARMO BioSciences, Inc., Redwood City, CA (US)

(72) Inventor: Martin Oft, Palo Alto, CA (US)

(73) Assignee: ARMO BioSciences, Inc., Redwood City, CA (US)

( * ) Notice: Subject to any disclaimer, the term of this patent is extended or adjusted under 35 U.S.C. 154(b) by 0 days.

(21) Appl. No.: 14/779,929

(22) PCT Filed: Apr. 15, 2014

(86) PCT No.: PCT/US2014/034247
§ 371 (c)(1),
(2) Date: Sep. 24, 2015

(87) PCT Pub. No.: WO2014/172392
PCT Pub. Date: Oct. 23, 2014

(65) Prior Publication Data
US 2016/0058838 A1 Mar. 3, 2016

Related U.S. Application Data

(60) Provisional application No. 61/813,563, filed on Apr. 18, 2013.

(51) Int. Cl.
| | | |
|---|---|---|
| A61K 38/20 | (2006.01) | |
| A61K 47/48 | (2006.01) | |
| C07K 14/54 | (2006.01) | |
| A61K 47/60 | (2017.01) | |
| A61K 9/00 | (2006.01) | |
| A61K 47/02 | (2006.01) | |

(52) U.S. Cl.
CPC .......... *A61K 38/2066* (2013.01); *A61K 47/60* (2017.08); *C07K 14/5428* (2013.01); *A61K 9/0019* (2013.01); *A61K 47/02* (2013.01); *C07K 2319/30* (2013.01); *C07K 2319/31* (2013.01)

(58) Field of Classification Search
None
See application file for complete search history.

(56) References Cited

U.S. PATENT DOCUMENTS

| | | | |
|---|---|---|---|
| 5,231,012 A | 7/1993 | Mosmann et al. | |
| 5,252,714 A | 10/1993 | Harris et al. | |
| 5,328,989 A | 7/1994 | Vellekamp et al. | |
| 5,624,823 A | 4/1997 | Sachs et al. | |
| 5,643,575 A | 7/1997 | Martinez et al. | |
| 5,665,345 A | 9/1997 | Yarchoan et al. | |
| 5,710,251 A | 1/1998 | Vellekamp et al. | |
| 5,824,784 A | 10/1998 | Kinstler et al. | |
| 5,866,134 A | 2/1999 | Fine et al. | |
| 5,876,969 A | 3/1999 | Fleer et al. | |
| 5,908,621 A | 6/1999 | Glue et al. | |
| 5,919,455 A | 7/1999 | Greenwald et al. | |
| 5,932,462 A | 8/1999 | Harris et al. | |
| 5,945,097 A | 8/1999 | Cutler | |
| 5,951,974 A | 9/1999 | Gilbert et al. | |
| 5,985,263 A | 11/1999 | Lee et al. | |
| 5,985,265 A | 11/1999 | Kinstler et al. | |
| 5,985,857 A | 11/1999 | Kinstler et al. | |
| 5,989,867 A | 11/1999 | Knappe et al. | |
| 6,217,857 B1 | 4/2001 | Mosmann et al. | |
| 6,248,514 B1 | 6/2001 | Hutchins et al. | |
| 6,387,364 B1 | 5/2002 | Fersuson | |
| 6,428,985 B1 | 8/2002 | Bromberg et al. | |
| 6,660,258 B1 | 12/2003 | Tovey | |
| 6,685,931 B1 | 2/2004 | Grint et al. | |
| 6,770,272 B2 | 8/2004 | Strom et al. | |
| 6,989,377 B2 | 1/2006 | Hayes et al. | |
| 7,001,770 B1 | 2/2006 | Atencio et al. | |
| 7,052,684 B2 | 5/2006 | Ferguson | |
| 7,052,686 B2 * | 5/2006 | Lee .................. | A61K 47/48215 424/78.3 |
| 7,056,701 B2 | 6/2006 | Fleer et al. | |
| 7,261,882 B2 | 8/2007 | Watkins | |
| 7,462,351 B2 | 12/2008 | Conroy et al. | |
| 7,611,700 B2 | 12/2009 | Gantier et al. | |
| 7,650,243 B2 | 1/2010 | Gantier et al. | |
| 7,666,400 B2 | 2/2010 | Chang et al. | |
| 7,749,490 B2 | 7/2010 | Sommer et al. | |
| 7,939,056 B2 | 5/2011 | Horwitz et al. | |
| 8,044,175 B2 | 10/2011 | Dransfield et al. | |
| 8,067,532 B2 | 11/2011 | MacLean | |

(Continued)

FOREIGN PATENT DOCUMENTS

| | | |
|---|---|---|
| CN | 1760209 | 10/2004 |
| CN | 102145178 | 8/2011 |

(Continued)

OTHER PUBLICATIONS

Mattos et al. PEGylation of interleukin-10 improves the pharmacokinetic profile and enhances the antifibrotic effectivity in CCl4-induced fibrogenesis in mice. J. Contr. Rel., 162, 84-91, 2012.*
Alvarez et al. Effects of PEGylation and immune complex formation on the pharmacokinetics and biodistribution of recombinant Interleukin-10 in mice. Drug Metab. Distrib. 40, 360-373, 2012.*
"Blood volume calculator" by EasySurf, Internet URL: https://web.archive.org/web/20121001142649/http://www.easysurf.cc/cnver22.htm) (Sep. 23, 2012—accessed Feb. 22, 2016).*
Recombinant Human IL-10 Protein, CF_ R&D Systems, accessed Feb. 22, 2016.*
Recombinant Mouse IL-10 Protein_ R&D Systems, accessed Feb. 22, 2016.*
Accession NP_036986.2; GI 148747382; Aug. 10, 2014.
Accession NP_776513.1; GI 41386772; Jan. 4, 2015.

(Continued)

*Primary Examiner* — Elly-Gerald Stoica
(74) *Attorney, Agent, or Firm* — Carol L. Francis; Bozicevic, Field & Francis LLP

(57) ABSTRACT

Methods of treating subjects having a disease or disorder responsive to IL-10, including methods of administration and dosing regimens associated therewith, are provided.

16 Claims, 3 Drawing Sheets

(56) References Cited

U.S. PATENT DOCUMENTS

| | | | |
|---|---|---|---|
| 8,287,856 B2 | 10/2012 | Li et al. | |
| 8,398,968 B2 | 3/2013 | Mayall | |
| 8,618,256 B2 | 12/2013 | Cox | |
| 8,691,205 B2 | 4/2014 | Blaisdell et al. | |
| 8,697,045 B2 | 4/2014 | Lee et al. | |
| 8,865,652 B2 | 10/2014 | Oft et al. | |
| 9,238,079 B2 | 1/2016 | Lee et al. | |
| 9,259,478 B2 | 2/2016 | Blaisdell et al. | |
| 9,364,517 B2 | 6/2016 | Oft et al. | |
| 2002/0044921 A1 | 4/2002 | Lee et al. | |
| 2003/0012775 A1 | 1/2003 | Brandt et al. | |
| 2003/0186386 A1 | 10/2003 | Hansen et al. | |
| 2004/0101965 A1 | 5/2004 | Griesenbach et al. | |
| 2004/0213795 A1 | 10/2004 | Collins et al. | |
| 2005/0008615 A1 | 1/2005 | Bam et al. | |
| 2005/0260767 A1 | 11/2005 | Clerici et al. | |
| 2006/0046961 A1 | 3/2006 | McKay et al. | |
| 2006/0210534 A1 | 9/2006 | Lee et al. | |
| 2006/0258607 A1 | 11/2006 | Jarosch et al. | |
| 2006/0270041 A1 | 11/2006 | Howe et al. | |
| 2007/0122379 A1 | 5/2007 | Nielsen et al. | |
| 2007/0134197 A1 | 6/2007 | Eichner et al. | |
| 2008/0058246 A1 | 3/2008 | Bhaskaran et al. | |
| 2008/0069797 A1 | 3/2008 | Roncarolo et al. | |
| 2008/0081031 A1* | 4/2008 | Oft | A61K 38/2066 424/85.2 |
| 2008/0096252 A1 | 4/2008 | Zamonst et al. | |
| 2008/0107629 A1 | 5/2008 | LaFace et al. | |
| 2009/0035256 A1 | 2/2009 | Sommer et al. | |
| 2009/0048148 A1 | 2/2009 | Engler et al. | |
| 2009/0214463 A1 | 8/2009 | Slobedman et al. | |
| 2009/0214471 A1 | 8/2009 | Oft et al. | |
| 2010/0068147 A1 | 3/2010 | Hibberd et al. | |
| 2010/0111898 A1 | 5/2010 | Pelura | |
| 2010/0129386 A1 | 5/2010 | Elson et al. | |
| 2010/0255496 A1 | 10/2010 | Schrader et al. | |
| 2010/0266532 A1 | 10/2010 | Ferguson | |
| 2010/0297070 A1 | 11/2010 | Dugan et al. | |
| 2011/0064690 A1 | 3/2011 | Lee et al. | |
| 2011/0091419 A1 | 4/2011 | Oft et al. | |
| 2011/0250163 A1* | 10/2011 | Blaisdell | A61K 38/2066 424/78.17 |
| 2011/0275123 A1 | 11/2011 | Paciotti et al. | |
| 2011/0305665 A1 | 12/2011 | Lee et al. | |
| 2011/0312010 A1 | 12/2011 | Manuilov | |
| 2012/0003221 A1 | 1/2012 | McDonagh et al. | |
| 2012/0115926 A1 | 5/2012 | Geary et al. | |
| 2012/0213793 A1 | 8/2012 | Huang et al. | |
| 2012/0219559 A1 | 8/2012 | Chen | |
| 2012/0252742 A1 | 10/2012 | Kranz et al. | |
| 2012/0270899 A1 | 10/2012 | Bannister et al. | |
| 2012/0321617 A1 | 12/2012 | Osterroth et al. | |
| 2013/0039911 A1 | 2/2013 | Bedi et al. | |
| 2013/0156774 A1 | 6/2013 | Kuchroo et al. | |
| 2014/0199750 A1 | 7/2014 | Weng et al. | |
| 2014/0256626 A1 | 9/2014 | Santi et al. | |
| 2014/0314795 A1 | 10/2014 | Riddell et al. | |
| 2014/0349402 A1 | 11/2014 | Cooper et al. | |
| 2015/0038678 A1 | 2/2015 | Eaton et al. | |
| 2015/0118244 A1 | 4/2015 | Shahabi et al. | |
| 2016/0340406 A1 | 11/2016 | Zhao et al. | |
| 2016/0361415 A1 | 12/2016 | Mumm et al. | |
| 2016/0375101 A1 | 12/2016 | Oft | |

FOREIGN PATENT DOCUMENTS

| | | |
|---|---|---|
| EP | 0251304 | 1/1988 |
| EP | 2066336 | 9/2012 |
| WO | WO 92/012725 | 8/1992 |
| WO | WO 92/012726 | 8/1992 |
| WO | 199417773 | 8/1994 |
| WO | 199503411 | 2/1995 |
| WO | WO 95/006058 | 3/1995 |
| WO | WO 95/019780 | 7/1995 |
| WO | WO 96/011953 | 4/1996 |
| WO | 199634969 | 11/1996 |
| WO | WO 97/003690 | 2/1997 |
| WO | WO 99/032134 | 7/1999 |
| WO | 199957297 | 11/1999 |
| WO | 200022124 | 4/2000 |
| WO | 200022137 | 4/2000 |
| WO | 200029599 | 5/2000 |
| WO | 200071718 | 11/2000 |
| WO | WO 01/005821 | 1/2001 |
| WO | 200117537 | 3/2001 |
| WO | 200128569 | 4/2001 |
| WO | WO 01/058950 | 8/2001 |
| WO | WO 02/026265 | 4/2002 |
| WO | WO 04/044006 | 5/2004 |
| WO | 2004056850 | 7/2004 |
| WO | WO 04/056850 | 7/2004 |
| WO | 2004106486 | 12/2004 |
| WO | 2004108088 | 12/2004 |
| WO | WO 06/075138 | 7/2006 |
| WO | WO 06/119170 | 11/2006 |
| WO | WO 08/054585 | 5/2008 |
| WO | WO 09/016043 | 2/2009 |
| WO | 2009036568 | 3/2009 |
| WO | 2010077853 | 7/2010 |
| WO | WO 10/077853 | 7/2010 |
| WO | WO 11/051489 | 5/2011 |
| WO | WO 12/004384 | 1/2012 |
| WO | WO 12/050923 | 4/2012 |
| WO | WO 12/050930 | 4/2012 |
| WO | 2013012414 | 1/2013 |
| WO | WO 13/113008 | 8/2013 |
| WO | 2014172392 | 10/2014 |
| WO | 2015070060 | 5/2015 |
| WO | 2015153753 | 10/2015 |

OTHER PUBLICATIONS

Accession NP_001009327.1; GI 57164347; Feb. 13, 2011.
Accession ABY86619.1; GI 166244598 ; Feb. 4, 2008.
Accession AAC23839.1; GI 3242896; Jun. 8, 2000.
"Guidance for Industry Immunogenicity Assessment for Therapeutic Protein Products," (2013) *FDA Guidances*.
"Highlights of Prescribing Information," (1997) *Rituxan*.
Recombinant Human IL-1 0 Protein, CF R&D Systems, accessed Feb. 22, 2016.
Recombinant Mouse I L -1 0 Protein R&D Systems, accessed Feb. 22, 2016.
Agata et al. (1996) "Expression of the PD-1 antigen on the surface of stimulated mouse T and B lymphocytes," *Int Immunol;* 8(5):765-772.
Aggen (2010) "Engineering Human Single-Chain T Cell Receptors," *Dissertation;* http://hdl.handle.net/2142/18585.
Alvarez et al. (2012) "Effects of PEGylation and Immune Complex Formation on the Pharmacokinetics and Biodistribution of Recombinant Interleukin10 in Mice," *Drug Metab Dispos;* 40(2):360-373.
Ansari and Raghava (2010) "Identification of conformational B-cell Epitopes in an antigen from its primary sequence," *Immunome Res;* 6:9pgs.
Ansell et al. (2002) "Phase 1 study of interleukin-12 in combination with rituximab in patients with B-cell non-Hodgkin lymphoma," *Blood;* 99:67-74.
Arakawa and Tsumoto (2003) "The effects of arginine on refolding of aggregated proteins: not facilitate refolding, but suppress aggregation," *Biochemical and Biophysical Research Communications;* 304:148-152.
Armstrong et al. (1996) "Interleukin 10 (IL-10) regulation of tumour necrosis factor cx (TNF-cx) from human alveolar macrophages and peripheral blood monocytes," *Thorax;* 51:143-149.
Asadullah et al. (1999) "Interleukin 10 Treatment of Psoriasis," *Arch Dermatol.;* 135-187-192.
Asadullah et al. (2003) "Interleukin 10 Therapy—Review of a New Approach," *Pharmacol. Rev.;* 55-241-269.

(56) References Cited

OTHER PUBLICATIONS

Bajetta et al. (1998) "Pilot Study of Subcutaneous Recombinant Human Interleukin 12 in Metastatic Melanoma," *Clinical Cancer Research;* 4:75-85.
Banerjee et al. (2012) "Poly(ethylene glycol)-Prodrug Conjugates: Concept, Design, and Applications," *Journal of Drug Delivery;* Article ID 103973:17 pages.
Bea at al. (2011) "Performance Evaluation of a Multiplex Assay for Future Use in Biomarker Discovery Efforts to Predict Body Composition," *Clin Chem Lab Med.;* 49(5):817-824.
Berger et al. (2009) "Safety and immunologic effects of IL-15 administration in nonhuman primates," *Blood;* 114:2417-2426.
Berman et al. (1996) "Systemic administration of cellular IL-10 induces an effective, specific, and long-lived immune response against established tumors in mice," *J Immunol;* 157:231-238.
Bilzer et al. (2006) "Role of Kupffer cells in host defense and liver disease," *Liver International;* 26:1175-1186.
Biswas et al. (2007) "Pathogen_specific CD8 T Cell Responses Are Directly Inhibited by IL-10," *J Immunol.;* 179:4520-4528.
Brady et al. (1994) "Reflections on a peptide," *Nature;* 368:692-693.
Brooks et al. (2008) "IL-10 and PD-L1 operate through distinct pathways to suppress T-cell activity during persistent viral infection," *PNAS;* 105(51):20428-20433.
Burgess (2009) "Refolding Solubilized Inclusion Body Proteins," *Methods in Enzymology;* 463:259-282.
Cai et al. (1999) "IL-10 enhances NK cell proliferation, cytotoxicity and production of IFN-q when combined with IL-18," *Eur. J. Immunol.;* 29:2658-2665.
Caliceti et al. (2012) "Effect of Plasma Membrane Cholesterol Depletion on Glucose Transport Regulation in Leukemia Cells," *PLoS One;* 7:e41246.
Cannistra & Niloff (1996) "Cancer of the uterine cervix," *New Eng I J Med* 334:1030-1038.
Cao et al. (2011) "Janus kinase activation by cytokine oncostatin M decreases PCSK9 expression in liver cells," *J Lipid Res.;* 52(3):513-530.
Capitini et al. (2009) "Modulating T cell Homeostasis with IL-7: Preclinical and Clinical Studies," *J Intern Med;* 266(2):141-153.
Cebon et al. (2003) "Two phase I studies of low dose recombinant human IL-12 with Melan-A and influenza peptides in subjects with advanced malignant melanoma," *Cancer Immunity;* 3:7 (18 pages).
Chamow et al. (1994) "Modification of CD4 Immunoadhesin with Monomethoxypoly(ethylene glycol) Aldehyde via Reductive Alkylation," *Bioconjugate Chern.;* 5:133-140.
Chan et al. (2015) "The Potentiation of IFN-γ and Induction of Cytotoxic Proteins by Pegylated IL-10 in Human CD8 T Cells," *J Interferon Cytokine Res;* 35(12):948-955.
Chen & Zlotnik (1991) "IL-10: a novel cytotoxic T cell differentiation factor," *J Immunol;* 147:528-534.
Chen et al. (2007) "Prediction of linear B-cell epitopes using amino acid pair antigenicity scale," *Amino Acids;* 33:423-428.
Choi et al. (2006) "Serum adiponectin, interleukin-10 levels and inflammatory markers in the metabolic 1-18 syndrome," *Diabetes Research and Clinical Practice;* 75:235-240.
Collins et al. (2012) "Trastuzumab induces antibody-dependent cellmediated cytotoxicity (ADCC) in HER-2-non-amplified breast cancer cell lines," *Annals of Oncology;* 23:1788-1795.
Compton et al. (2004) "Pathogenesis of Enterotropic Mouse Hepatitis Virus in Immunocompetent and Immunodeficient Mice," *Comparative Medicine;* 54(6):681-689.
Conlon et al. (2014) "Redistribution, Hyperproliferation, Activation of Natural Killer Cells and CDS T Cells, and Cytokine Production During First-in-Human Clinical Trial of Recombinant Human Interleukin-15 in Patients With Cancer," *Journal of Clinical Oncology;* 33(1):74-82.
Couder et al. (1993) "Synthesis and biological activities of ψ(CH2NH) pseudopeptide analogues of the C-terminal hexapeptide of neurotensin," *Int. J. Peptide Protein Res.;* 41:181-184.

D'Andrea et al. (1993) "Interleukin 10 (IL-10) Inhibits Human Lymphocyte Interferon 3,-Production by Suppressing Natural Killer Cell Stimulatory Factor/IL-12 Synthesis in Accessory Cells," *J. Exp. Med;* 178:1041-1048.
Das et al. (2012) "IL-10—Producing Regulatory B Cells in the Pathogenesis of Chronic Hepatitis B Virus Infection," *J. Immunol.;* 189(8):3925-3935.
Davidson & Diamond (2001) "Autoimmune diseases," *New Engl J Med;* 345:340-350.
De Waal Malefyt et al. (1991) "Interleukin 10 (IL-10) and viral IL-10 strongly reduce antigen-specific human T cell proliferation by diminishing the antigen-presenting capacity of monocytes via downregulation of class II major histocompatibility complex expression," *J Exp Med;* 174(4):915-924.
De Waal Malefyt et al. (1991) "Interleukin 10(IL-10) Inhibits Cytokine Synthesis by Human Monocytes: An Autoregulatory Role of IL-10 Produced by Monocytes," *J. Exp. Med;* 174:1209-1220.
Devay et al. (2013) "Characterization of Proprotein Convertase Subtilisin/Kexin Type 9 (PCSK9) Trafficking Reveals a Novel Lysosomal Targeting Mechanism via Amyloid Precursor-like Protein 2 (APLP2)," *J. Biol. Chem.;* 288:10805-10818.
Dolgin (2011) "Trial puts niacin- and cholesterol dogma—in the line of fire," *Natue Medicine;* 17(7):356.
Dorner et al. (2011) "A genetically humanized mouse model for hepatitis C virus infection," *Nature;* 474:208-211.
Easy Surf. Blood Volume Calculator [online]Oct. 1, 2012 [retrieved Aug. 18, 2014]. Available on the internet: <URL: https://web.archive.org/web/20121 001142649/http://www.easysurfcc/cnver22.htm >.
Ehrlich et al. (2013) "Preparation and Characterization of Albumin Conjugates of a Truncated Peptide YY Analogue for Half-Life Extension," *Bioconjug. Chem.;* 24(12):2015-2024.
El-Manzalawy et al. (2008) "Predicting linear B-cell epitopes using string kernels," *J Mol Recognit;* 21:243-255.
Emmerich et al. (2012) "IL-10 directly activates and expands tumor-resident CD8(+) T cells without de novo infiltration from secondary lymphoid organs," *Cancer Res;* 72(14):3570-3581.
Engel et al. (2006) "Using Endoproteinases Asp-N and Glu-C to Improve Protein Characterization," *Promega Corporation;* $10^{th}$ edition.
Enzinger & Mayer (2003) "Esophageal cancer," *New Eng I J Med;* 349:2241-2252.
Fahnert et al. (2012) "Using Folding Promoting Agents in Recombinant Protein Production: A Review," *Methods inn Molecular Biology;* 824:3-36.
Fang et al. (2015) "Programmed Death 1 (PD-1) is involved in the development of proliferative diabetic retinopathy by mediating activation-induced apoptosis," *Mol Vis;* 21:901-910.
Farrar et al. (1999) "Cancer dormancy. VII. A regulatory role for COB+ T cells and IFN-gamma in establishing and maintaining the tumor-dormant state," *J Immunol* 162:2842-2849.
Fehniger and Caligiuri (2001) "Interleukin 15: biology and relevance to human disease," *Blood;* 97:14-32.
Feingold et al. (1996) "Endotoxin, TNF, and IL-I decrease cholesterol 7a-hydroxylase mRNA levels and activity," *Journ of Lipid Res;* 37:223-228.
Fiorentino et al. (1989) "Two types of mouse T helper cell. IV. Th2 clones secrete a factor that inhibits cytokine production by Th1 clones," *J Exp Med;* 170:2081-2095.
Forastiere et al. (2001) "Head and neck cancer," *New Engl J Med* 345:1890-1900.
Fridman et al. (2012) "The immune contexture in human tumours: impact on clinical outcome," *Nature;* 12:298-306.
Fry and Mackall (2002) "Interleukin-7: from bench to clinic," *Blood;* 99:3892-3904.
Fujiwara et al. (2010) "Extraction and purification of human interleukin-10 from transgenic rice seeds," *Protein Expression and Purification;* 72:125-130.
Galon et al. (2013) "The Continuum of Cancer Immunosurveillance: Prognostic, Predictive, and Mechanistic Signatures," *Immunity;* 39:11-26.
Gameren et al. (1994) "Effects of Recombinant human interleukin-6 in cancer patients: a phase I-II study," *Blood;* 84:1434-1441.

(56) References Cited

OTHER PUBLICATIONS

Gao et al. (2012) "BEST: Improved Prediction of B-Cell Epitopes from Antigen Sequences," *PLoS ONE;* 7(6): e40104.
GenBank Accession No. M37897 "Mouse interleukin 10 mRNA, complete cds," dated Apr. 27, 1993.
GenBank Accession No. NP 000563 "interleukin-10 precursor [*Homo sapiens*]," dated Mar. 3, 1995.
Georgescu et al. (1997) "Interleukin-10 Promotes Activation-induced Cell Death of SLE Lymphocytes Mediated by Fas Ligand," *J. Clin. Invest.;* 100:2622-2633.
Gerstein et al. (2008) "Effects of Intensive Glucose Lowering in Type 2 Diabetes," *New England J of Medicine;* 358(24):2545-2559.
Gesser et al. (1997) "Identification of functional domains on human interleukin 10," *Proc. Natl. Acad. Sci.;* 94:14620-14625.
Gierens et al. (2000) "Interleukin-6 Stimulates LDL Receptor Gene Expression via Activation of Sterol-Responsive and Sp1 Binding Elements," *Arterioscler Thromb Vasc Biol.;* 20:1777-1783.
Gregoriadis et al., (2005) "Improving the therapeutic efficacy of peptides and proteins: A role for polysialic acids," *Int. J. Pharmaceutics;* 300(1-2):125-130.
Groux et al. (1998) "A transgenic model to analyze the immunoregulatory role of IL-10 secreted by antigen-presenting cells," *J Immunol;* 162:1723-1729.
Groux et al. (1998) "Inhibitory and stimulatory effects of IL-10 on human COB+ T cells," *J Immunol;* 160:3188-3193.
Hagenbaugh et al. (1997) "Altered immune responses in interleukin 10 transgenic mice," *J Exp Med;* 185:2101-2110.
Hamada et al. (2009) "Effect of Additives on Protein Aggregation," *Current Pharm Biotech;* 10:400-407.
Hashizume et al. (2010) "Overproduced interleukin 6 decreases blood lipid levels via upregulation of very-low-density lipoprotein receptor," *Ann Rheum Dis;* 69:741-746.
Heeschen et al. (2003) "Serum Level of the Antiinflammatory Cytokine Interleukin-1 0 Is an Important Prognostic Determinant in Patients With Acute Coronary Syndromes," *Circulation;* 107:2109-2114.
Hombach et al. (2013) "Arming Cytokine-induced Killer Cells With Chimeric Antigen Receptors: CD28 Outperforms Combined CD28-OX40 'Super-stimulation'," *Molecular Therapy;* 12:2268-2277.
Howard et al. (1993) "Interleukin 10 Protects Mice from Lethal Endotoxemia," *J. Exp. Med.;* 177:1205-1208.
Huang et al. (1996) "Interleukin 10 Suppresses Tumor Growth and Metastasis of Human Melanoma Cells: Potential Inhibition of Angiogenesis," Clinical Cancer Research, *The American Assn for Cancer Research;* 2(12):1969-1979.
Huang et al. (2010) "Depletion of Liver Kupffer Cells Prevents the Development of Diet-Induced Hepatic Steatosis and Insulin Resistance," 59:347-357.
Huntington et al. (2008) "IL-15 trans-presentation promotes human NK cell development and diff erentiation in vivo," *J. Exp. Med.;* 206:25-34.
Hustoft et al. (2012) "A Critical Review of Trypsin Digestion for LC-MS Based Proteomics," *InTech;* Chapter 4.
Infante et al. (2015) "A first-in-human dose escalation study of PEGylated recombinant human IL-10 (AM0010) in advanced solid tumors," *ASCO Meeting Abstracts;* 33(15 suppl):3017.
International Search Report; PCT/US01/42431, dated Aug. 20, 2002.
Ishikawa et al. (2005) "Interleukin-10 plasmid DNA inhibits liver and lung metastasis of Colon 26 adenocarcinoma in mice," *Proceedings of the Annual Meeting, American Association for Cancer Research;* vol. 46, Abstract # 3364.
Izbicki et al. (1997) "Prognostic value of immunohistochemically identifiable tumor cells in lymph nodes of patients with completely resected esophageal cancer," *New Engl J Med;* 337:1188-1194.
Jameson et al. (1994) "A rationally designed CD4 analogue inhibits experimental allergic encephalomyelitis," *Nature;* 368:744-746.
Jevšhevar et al. (2010) "PEGylation of therapeutic proteins," *Biotechnol. J.;* 5:113-128.

Jiang et al. (2015) "T-cell exhaustion in the tumor microenvironment," *Cell Death Dis;* 6:e1792.
Josephson et al. (2001) "Crystal Structure of the IL-10/IL-10R1 Complex Reveals a Shared Receptor Binding Site," *Immunity;* 14:35-46.
Jungbauer et al. (2007) "Current status of Technical protein refolding," *Journal of Biotechnology;* 128:587-596.
Katre (1993) "The Conjugation of Proteins with Polyethylene Glycol and Other Polymers Altering Properties of Proteins to Enhance their Therapeutic Potential," *Advanced Drug Delivery Reviews;* 10(1):91-114.
Khow and Suntrarachun (2012) "Strategies for production of active eukaryotic proteins in bacterial expression system," *Asian Pac. J. Biomed.;* 2(2):159-162.
Kimball et al (2002) "Clinical and Immunologic Assessment of Patients With Psoriasis in a Randomized, Double-blind, Placebo-Controlled Trial Using Recombinant Human Interleukin 10," *Arch Dermatol;* 138:1341-1346.
Kinstler et al. (1996) "Characterization and Stability of N-terminally PEGylated rhG-CSF," *Pharm. Res.;* 13:996-1002.
Kinstler et al. (2002) "Mono-N-terminal poly(ethylene glycol)-protein conjugates," *Advanced Drug Delivery Reviews;* 54:477-485.
Klompus et al. (2008) "A simple novel method for the preparation of noncovalent homodimeric, biologically active human interleukin 10 in *Escherichia coli*—Enhancing protein expression by degenerate PCR of 59 DNA in the open reading frame," *Protein Expression and Purification;* 62:199-205.
Kokura et al. (2003) "The blocking of NFkB activation by systemicinterleukin-10 gene therapy inhibits liver and lung metastasis of colon 26 adenocarcinoma in mice" *Gastroenterology;* 124(4): Abstract No. W965.
Kokura et al. (2005) "Interleukin-1 0 plasmid DNA inhibits subcutaneous tumor growth of Colon adenocarcinoma in mice," *Cancer Letters;* 218:171-179.
Kong et al. (2005) "In vivo activities of cytokine oncostatin M in the regulation of plasma lipid levels," *Journal of Lipid Research;* 46:1163-1171.
Körholz et al. (1997) "The Role of Interleukin-10 (IL-10) in IL-15-Mediated T-Cell Responses," *Blood;* 90(11):4513-4521.
Kundu et al. (1996) "Antimetastatic and antitumor activities of interleukin 10 in a murine model of breast cancer," *J Nail Cancer Inst;* 88:536-541.
Kundu et al. (1997) "Interleukin-10 inhibits tumor metastasis, down regulates MHC class I, enhances NK lysis," *Cellular Immunology, Academic Press;* 180(1):55-61.
Kute et al. (2012) "Understanding key assay parameters that affect measurements of trastuzumab-mediated ADCC against Her2 positive breast cancer cells," *OncoImmunology;* 1(6):810-821.
Langowski et al. (2006) "IL-23 promotes tumour incidence and growth," *Nature;* 442:461-465.
Lasek et al. (2014) "Interleukin 12: still a promising candidate for tumor immunotherapy?" *Cancer Immunol Immunother;* 63:419-435.
Le et al. (2001) "Pre-existing tumor-sensitized T cells are essential for eradication of established tumors by IL-12 and cyclophosphamide plus IL-12," *J Immunol;* 167:6765-6772.
Lehmann et al. (2014) "IL-12 Directs Further Maturation of Ex Vivo Differentiated NK Cells with Improved Therapeutic Potential," *PLoS One;* 9(1):e87131 (12 pages).
Lewington and Clark (2005) "Combined Effects of Systolic Blood Pressure and Total Cholesterol on Cardiovascular Disease Risk," *Circulation;* 112:3373-3374.
Lindhout et al. (2011) "Site-specific enzymatic polysialylation of therapeutic proteins using bacterial enzymes," *PNAS;* 108(18)7397-7402.
Liu et al. (2003) "IL-10 Mediates Suppression of the CD8 T Cell IFN-γ Response to a Novel Viral Epitope in a Primed Host," *J Immunol;* 171:4765-4772.
Loebbermann et al. (2012) "IL-10 Regulates Viral Lung Immunopathology during Acute Respiratory Syncytial Virus Infection in Mice," *PLoS ONE;* 7(2):e32371.

(56) References Cited

OTHER PUBLICATIONS

Lopez et al. (2005) "IL-12 and IL-10 Expression Synergize to Induce the Immune-Mediated Eradication of Established Colon and Mammary Tumors and Lung Metastasis," *J Immunol;* 175:5885-5894.
Lowe et al. (1998) "Impact of Major Cardiovascular Disease Risk Factors, Particularly in Combination, on 22-Year Mortality in Women and Men," *Arch Intern Med;* 158:2007-2014.
Lu et al. (2004) "Prognostic factors in resected stage I non-small-cell lung cancer: a multivariate analysis of six molecular markers," *J Clin Oneal;* 22:4575-4583.
Lugli et al. (2010) "Transient and persistent effects of IL-15 on lymphocyte homeostasis in nonhuman primates," *Blood;* 116:3238-3248.
Lynch and Chapelle (2003) "Hereditary colorectal cancer," *New Eng I J Med;* 348:919-932.
Martin et al. (2001) "B-Cell Deficiency Suppresses Vaccine-Induced Protection against Murine Filariasis but Does Not Increase the Recovery Rate for Primary Infection," *Infect. Immun.;* 69(11):7067-7073.
Mattos et al. (2012) "PEGylation of interleukin-10 improves the pharmacokinetic profile and enhances the antifibrotic effectivity in CCl.-induced fibrogenesis in mice," *J Control Release;* 162(1):84-91.
Maus et al. (2014) "Antibody-modified T cells: CARs take the front seat for hematologic malignancies," *Blood;* 123(17):2625-2635.
Miki Toyokazu et al. (2000) "Anti-metastatic effect of IL-10 gene modification in human lung cancer cells is differentially regulated by organ microenvironments," *Proceedings of the Annual Meeting American Association for Cancer Research;* 41:3.
Monk (2011) "A Strategy for the Quantification of Protein Polyethylene Glycol (PEG) Derivatized Sites using iTRAQ," University of California, San Diego; 1-51.
Moore et al. (1990) "Homology of cytokine synthesis inhibitory factor (IL-10) to the Epstein-Barr virus gene BCRFI," *Science;* 248:1230-1234.
Moran et al. (1994) "Human leukemia inhibitory factor inhibits development of experimental atherosclerosis," *Arterioscler Thromb Vasc Biol.;* 14(8):1356-1363.
Motzer et al. (2001) "Randomized Multicenter Phase II Trial of Subcutaneous Recombinant Human Interleukin-12 Versus Interferon-α2a for Patients with Advanced Renal Cell Carcinoma," *Journal of Interferon and Cytokine Research;* 21:257-263.
Naicker et al. (2009) "Interleukin-10 Promoter Polymorphisms Influence HIV-1 Susceptibility and Primary HIV-1 Pathogenesis," *J. Infect. Dis.;* 200(3):448-452.
Natsume et al. (2009) "Improving effector functions of antibodies for cancer treatment: Enhancing ADCC and CDC," *Drug Design, Development and Therapy;* 3:7-16.
Nenseter et al. (1992) "Role of liver endothelial and Kupffer cells in clearing low density lipoprotein from blood in hypercholesterolemic rabbits," *J of Lipid Res;* 33:867-877.
Neven et al. (2013) "A Mendelian predisposition to B cell lymphoma caused by IL-10R deficiency," *Blood;* 122(23):3712-3722.
Neyrinck et al. (2009) "Critical role of Kupffer cells in the management of diet-induced diabetes and obesity," *Biochemical and Biophysical Research Communications;* 385:351-356.
Nicholls et al. (2012) "Is niacin ineffective? or did AIM-HIGH miss its target?," *Cleveland Clinic Journ of Med;* 79(1):38-43.
Noguchi et al. (2003) "PDX-1 Protein Containing Its Own Antennapedia-Like Protein Transduction Domain Can Transduce Pancreatic Duct and Islet Cells," *Diabetes;* 52(7):1732-1737.
Osaki et al. (1999) "Potent antitumor effects mediated by local expression of the mature form of the interferon-γ inducing factor, interleukin-18 (IL-18)," *Gene Therapy;* 6:808-815.
Osborne (1998) "Tamoxifen in the treatment of breast cancer," *New Engl J Med;* 339:1609-1618.
Overdijk et al. (2011) "Epidermal Growth Factor Receptor (EGFR) Antibody-Induced Antibody-Dependent Cellular Cytotoxicity Plays a Prominent Role in Inhibiting Tumorigenesis, Even of Tumor Cells Insensitive to EGFR Signaling Inhibition," *Journal of Immunology;* 187:3383-3390.
Pardoll (2012) "The blockade of immune checkpoints in cancer immunotherapy," *Cancer;* 12:252-264.
Park et al. (2011) "IL-15-Induced IL-10 Increases the Cytolytic Activity of Human Natural Killer Cells," *Mol. Cells;* 32:265-272.
Pasut and Veronese (2012) "State of the art in PEGylation: The great versatility achieved after forty years of research," *Journal of Controlled Release;* 161:461-472.
Payne et al. (2010) "Product development issues for PEGylated proteins," *Pharmaceutical Development and Technology;* 16:423-440.
Pegram et al. (2012) "Interleukin 12: Stumbling Blocks and Stepping Stones to Effective Anti-Tumor Therapy," *Advancements in Tumor Immunotherapy and Cancer Vaccines;* Chapter 10:197-218.
Pellegrini et al. (2011) "IL-7 Engages Multiple Mechanisms to Overcome Chronic Viral Infection and Limit Organ Pathology," *Cell;* 144:1-13.
Pettit et al. (1997) "Structure-Function Studies of Interleukin 15 using Site-specific Mutagenesis, Polyethylene Glycol Conjugation, and Homology Modeling," *J. Biol. Chem.* 272:2312-2318.
Rachmawati et al. (2004) "Pharmacokinetic and Biodistribution Profile of Recombinant Human Interleukin-10 Following Intravenous Administration in Rats with Extensive Liver Fibrosis," *Pharm. Res.;* 21(11):2072-2078.
Rachmawati et al. (2007) "Chemical Modification of Interleukin-10 with Mannose 6-Phosphate Groups Yields a Liver-Selective Cytokine," *Drug Metabolism and Disposition;* 35(5):814-821.
Radwanski et al. (1998) "Pharmacokinetics and Leukocyte Responses of Recombinant Human Interleukin-10," *Pharm. Res.;* 15(12):1895-1901
Ramirez-Montagut et al. (2003) "Immunity to melanoma: unraveling the relation of tumor immunity and autoimmunity," *Oncogene;* 22:3180-3187.
Re et al. (2002) "Preclinical evaluation of the antiproliferative potential of STI571 in Hodgkin's disease," *British Journal of Cancer;* 86:1333-1335.
Reynolds, et al. (2002) "Proteolytic 18O Labeling for Comparative Proteomics: Evaluation of Endoprotease Glu-C as the Catalytic Agent," *Journal of Proteome Research;* 1(1):27-33.
Roberts et al. (2012) "Chemistry for peptide and protein PEGylation," *Advanced Drug Delivery Reviews;* 64:116-127.
Rolfe et al. (2003) "Leukaemia inhibitory factor retards the progression of atherosclerosis," *Cardiovascular Research;* 58:222-230.
Russo et al. (2006) "Randomized trial of pegylated interferon a-2b monotherapy in haemodialysis patients with chronic hepatitis C," *Nephrol Dial Transplant;* 21:437-443.
Saha and Raghava (2006) "Prediction of continuous B-cell epitopes in an antigen using recurrent neural network," *Proteins;* 65:40-48.
Sakamoto et al. (2003) "Interleukin-10 gene therapy enhances antitumor effect of CPT-11 for lung metastasis of colon26 adenocarcinoma in mice," *Gastroenterology;* 124(4):A456-A457.
Sawaya et al. (2003) "Risk of cervical cancer associated with extending the interval between cervical-cancer screenings," *New Engl J Med;* 349:1501-1509.
Schäffner et al. (2001) "Cosecretion of Chaperones and Low-Molecular-Size Medium Additives Increases the Yield of Recombinant Disulfide-Bridged Proteins," *Applied and Environmental Microbiology;* 67(9):3994-4000.
Sela and Zisman (1997) "Different roles of D-amino acids in immune phenomena," *Faseb J.;* 11:449-456.
Shen et al. (2013) "Proprotein convertase subtilisin/kexin type 9 potentially influences cholesterol uptake in macrophages and reverse cholesterol transport," *FEBS Letters;* 587:1271-1274.
Smith et al. (1996) "Administration of interleukin-1 0 at the time of priming protects Corynebacterium parvum-primed mice against LPS- and TNF-alpha-induced lethality," *Cellular Immunology* 173(2):207-214.
Sneller et al. (2011) "IL-15 administered by continuous infusion to rhesus macaques induces massive expansion of CD8 T effector memory population in peripheral blood," *Blood;* 118(26):6845-6848.

(56) References Cited

OTHER PUBLICATIONS

Soman et al. (2009) "MTS dye based colorimetric CTLL-2 cell proliferation assay for product release and stability monitoring of Interleukin-15: Assay qualification, standardization and statistical analysis," *J Immunol Methods;* 348(1-2):83-94.
Song et al. (2012) "CD27 costimulation augments the survival and antitumor activity of redirected human T cells in vivo," *Blood;* 119(3):696-706.
Srivastava et al. (2013) "Effects of interleukin-18 on natural killer cells: costimulation of activation through Fc receptors for immunoglobulin," *Cancer Immunol Immunother;* 62(6):1073-1082.
Storici and Resnick (2006) "The delitto perfetto approach to in vivo site-directed mutagenesis and chromosome rearrangements with synthetic oligonucleotides in yeast," *Methods in Enzymology;* 409:329-345.
Sweredoski and Baldi (2009) "COBEpro: a novel system for predicting continuous B-cell epitopes," *Protein Eng Des Sel;* 22:113-120.
Syto et al. (1998) "Structural and biological stability of the human interleukin 10 homodimer," *Biochemistry;* 37(48):16943-16951.
Teng et al. (2015) "IL-12 and IL-23 cytokines: from discovery to targeted therapies for immune-mediated inflammatory diseases," *Nature Medicine;* 21:719-729.
Tilg et al. (2002) "Treatment of Crohn's disease with recombinant human interleukin 10 induces the proinflammatory cytokine interferon γ," *Gut;* 50:191-195.
Trandem et al. (2011) "Virally Expressed Interleukin-10 Ameliorates Acute Encephalomyelitis and Chronic Demyelination in Coronavirus-Infected Mice," *J. Virol.;* 85(14):6822-6831.
Tréhin et al. (2004) "Cellular uptake but low permeation of human calcitonin-derived cell penetrating peptides and Tat(47-57) through well-differentiated epithelial models," *Pharm. Research;* 21:1248-1256.
Tsumoto et al. (2003) "Practical considerations in refolding proteins from inclusion bodies," *Protein Expression and Purification;* 28:1-8.
Tsumoto et al. (2004) "Role of Arginine in Protein Refolding, Solubilization, and Purification," *Biotechnol. Prog.;* 20:1301-1308.
Valabrega et al. (2007) "Trastuzumab: mechanism of action, resistance and future perspectives in HER2-overexpressing breast cancer," *Annals of Oncology;* 18:977-984.
Van Deventer et al. (1997) "Multiple Doses of Intravenous Interleukin 10 in Steroid-Refractory Crohn's Disease," *Gastroenterology,* 113:383-389.
Vicari and Trinchieri (2004) "Interleukin-10 in viral diseases and cancer: exiting the labyrinth?," *Immunological Reviews;* 202:223-236.
Vigneron et al. (2013) "Database of T cell-defined human tumor antigens: the 2013 update," *Cancer Immunity;* 13:15-20.
Virgin, et al. (2009) "Redefining Chronic Viral Infection," *Cell;* 138:30-50.
Von Andrian and Mackay (2000) "T-cell function and migration. Two sides of the same coin," *New Engl J Med;* 343:1020-1034.
Waldmann et al. (2011) "Safety (toxicity), pharmacokinetics, immunogenicity, and impact on elements of the normal immune system of recombinant human IL-15 in rhesus macaques," *Blood;* 117:4787-4795.
Walter and Nagabhushan (1995) "Crystal structure of interleukin 10 reveals an interferon gamma-like fold," *Biochemistry;* (38):12118-12125.
Wee et al. (2010) "SVM-based prediction of linear B-cell epitopes using Bayes Feature Extraction," *BMC Genomics;* 11(Supp 4):S21.
Wender et al. (2000) "The design, synthesis, and evaluation of molecules that enable or enhance cellular uptake: peptoid molecular transporters," *Proc. Natl. Acad. Sci. USA;* 97:13003-13008.
Wilson et al. (2011) "The role of IL-10 in regulating immunity to persistent viral infections," *Curr Top Microbiol Immunol.;* 350:39-65.
Witsch et al. (2010) "Roles for Growth Facotes in Cancer Progression," *Physiology;* 25(2):85-101.

Wu et al. (2012) "Immunotherapies: The Blockade of Inhibitory Signals," *Int. J. Biol. Sci.;* 8:1420-1430.
Xu et al. (2010) "Regulation of Antitumor Immune Responses by the IL-12 Family Cytokines, IL-12, IL-23, and IL-27," Clinical and Developmental Immunology; Article ID:832454 (9 pages).
Yamaguchi and Miyazaki (2014) "Refolding Techniques for Recovering Biologically Active Recombinant Proteins from Inclusion Bodies," *Biomolecules;* 4:235-251.
Yoshioka et al. (2011) "Development of a novel DDS for site-specific PEGylated proteins," *Chem. Central J.;* 5:25.
Younes et al. (2004) "Phase II Clinical Trial of Interleukin-12 in Patients with Relapsed and Refractory Non-Hodgkin's Lymphoma and Hodgkin's Disease," *Clinical Cancer Research;* 10:5432-5438.
Zauner et al. (1996) "Glycerol Enhancement of Ligand-Polylysine/DNA Transfection," *BioTechniques;* 20:905-913.
Zdanov et al. (1995) "Crystal structure of interleukin-10 reveals the functional dimer with an unexpected topological similarity to interferon γ," *Structure;* 3:591-601.
Zdanov et al. (1996) "Crystal structure of human interleukin-10 at 1.6 A resolution and a model of a complex with its soluble receptor," *Protein Sci.;* (10):1955-1962.
Zender et al. (2002) "VP22-mediated intercellular transport of p53 in hepatoma cells in vitro and in vivo," *Cancer Gene Ther.;* 9(6):489-496.
Zheng et al. (1996) "Interleukin-10 inhibits tumor metastasis through an NK cell-dependent mechanism," *J Exp Med;* 184:579-584.
Emmerich J., et al., (2012) "Autochthonous T cells to the rescue: IL-10 directly activates tumor-resident CD8(+) T cells", Oncoimmunology, 1(9):1637-1639.
Mumm, JB, et al., (2012) "Killing from within", Oncoimmunology, 1(9):1598-1600.
Emmerich J., et al., (2012) "IL-10 directly activates and expands tumor-resident CD8(+) T cells without de novo infiltration from secondary lymphoid organs", Cancer Res., 72(14):3570-3581.
Mumm, JB, et al., (2011) "IL-10 elicits IFNγ-dependent tumor immune surveillance", Cancer Cell, 20(6):781-796.
Mumm, JB and Oft M., (2008) "Cytokine-based transformation of immune surveillance into tumor-promoting inflammation", Oncogene, 27(45):5913-5919.
Josephson, K. et al., (2001) "Crystal Structure of the IL-10/IL-10R1 Complex Reveals a Shared Receptor Binding Site", Immunity, 15(1):35-46.
Payne, et al. (2010) "Product development issues for PEGylated proteins," Pharmaceutical Development and Technology, 16:423-440.
Monk, R., (2014) "A Strategy for the Quantification of Protein Polyethylene Glycol (PEG) Derivatized 27 Sites using iTRAQ" University of California, San Diego, 1-51. Retrieved from the Internet: <https://escholarship.org/uc/item/0bk9f1f4>.
Heeschen et al., (2003) "Serum Level of the Antiinflammatory Cytokine Interleukin-10 Is an Important Prognostic Determinant in Patients With Acute Coronary Syndromes," Circulation, 107:2109-2114.
Choi et al., (2006) "Serum adiponectin, interleukin-10 levels and inflammatory markers in the metabolic syndrome," Diabetes Research and Clinical Practice, 75:235-240.
Lindsay et al., (2002) "IL-10 gene therapy prevents TNBS-induced colitis," Gene Therapy, 9(24):1715-1721.
Mumm et al., (2013) "Pegylated .IL-10 induces cancer immunity the surprising role of IL-10 as a potent inducer of IFN-g-mediated C_D8p T cell cytotoxicity," BioEssays, 35:623-631.
Mattos et al.,(2012) "11 PEGylation of interleukin-10 improves the pharmacokinetic profile and enhances the antifibrotic effectivity in eel-induced fibrogenesis in mice", Journal of Controlled Release, Elsevier, Amsterdam, NL, 162(I):84-91.
Gargett et al., (2015) "Different cytokine and stimul ation conditions influence t he expansion and immune phenotype of third-generat ion chimeric antigen receptor T cells specific for tumor antigen GD2", Cytotherapy, 17 (4):487-495.
Gill et al., (2015) "Going viral: Chimericantigen receptor T-cell therapy forhematological malignancies", Immunological Reviews 28150181 Blackwell Publishing Ltd GBR, 263(1):68-89.

(56) References Cited

OTHER PUBLICATIONS

Teng et al., (2011) "Stable IL-10: A new therapeutic that promotes tumor immunity" Cancer Cell 2011 Cell Press USA, 20(6):691-693.
Mumm et al. (2011) "IL-10 elicits IFNγ-dependent tumor immune surveillance," Cancer Cell; 20(6):781-796.
Muecke, Susanne, et al., (2000) "Suppression of the Tumorigenic Growth of Burkitt's Lymphoma Cells in Immunodeficient Mice by Cytokine Gene Transfer Using EBV-Derived Episomal Expression Vectors", Int. J. Cancer, 86:301-306.
Steel, JC et al., (2012) "Biology and its Therapeutic Implications in Cancer", Trends in Pharmacological Sciences, 33 :11:35-41.
Klebanoff, CA et al., (2004) "IL-15 Enhances the in vivo Antitumor Activity of Tumor-reactive CD8+ T Cells", Proceedings of the National Academy of the Sciences of the U.S.A., 101(7):1969-1974.
NCT02009449, "A Phase 1, OpenLabel Dose Escalation FirstinHuman Study to Evaluate the Tolerability, Safety, Maximum Tolerated Dose, Preliminary Clinical Activity and Pharmacokinetics of AM0010 in Patients With Advanced Solid Tumors", ClinicalTrials. gov, Dec. 11, 2013, 3 pages.
NCT02009449, "A Phase 1, OpenLabel Dose Escalation FirstinHuman Study to Evaluate the Tolerability, Safety, Maximum Tolerated Dose, Preliminary Clinical Activity and Pharmacokinetics of AM0010 in Patients With Advanced Solid Tumors", ClinicalTrials. gov, Jan. 31, 2014, 3 pages.
NCT02009449, "A Phase 1, OpenLabel Dose Escalation FirstinHuman Study to Evaluate the Tolerability, Safety, Maximum Tolerated Dose, Preliminary Clinical Activity and Pharmacokinetics of AM0010 in Patients With Advanced Solid Tumors", ClinicalTrials. gov, Jul. 17, 2014, 6 pages.
NCT02009449, "A Phase 1, OpenLabel Dose Escalation FirstinHuman Study to Evaluate the Tolerability, Safety, Maximum Tolerated Dose, Preliminary Clinical Activity and Pharmacokinetics of AM0010 in Patients With Advanced Solid Tumors", ClinicalTrials. gov, Mar. 24, 2015, 7 pages.
NCT02009449, "A Phase 1, OpenLabel Dose Escalation FirstinHuman Study to Evaluate the Tolerability, Safety, Maximum Tolerated Dose, Preliminary Clinical Activity and Pharmacokinetics of AM0010 in Patients With Advanced Solid Tumors", ClinicalTrials. gov, Jan. 12, 2016, 7 pages.
NCT02009449, "A Phase 1, OpenLabel Dose Escalation FirstinHuman Study to Evaluate the Tolerability, Safety, Maximum Tolerated Dose, Preliminary Clinical Activity and Pharmacokinetics of AM0010 in Patients With Advanced Solid Tumors", ClinicalTrials. gov, Oct. 2, 2016, 7 pages.
NCT02923921, "Randomized Study of AM0010 in Combination With FOLFOX Compared to FOLFOX Alone as Secondline Tx in Pts With Meta Pancreatic Cancer That Has Progressed During or Following a FirstLine Gemcitabine containing Regimen", ClinicalTrials.gov, Oct. 4, 2016, 3 pages.
Cindric, et al., (2007) "Structural 1-16 characterization of PEGylated rHuG-CSF and location of PEG attachment sites". Journal of Pharmaceutical and Biomedical Analysis. New York. NY. US, 44(2):388-395.
Schneiderheinze, J., et al., (2009) "Rapid online proteolytic mapping of PEGylated rhGH for identity confirmation. quantitation of methionine oxidation and quantitation of UnPEGylated N-terminus using HPLC with UV detection", Journal of Chromatography B: Biomedical Sciences & Applications. Elsevier. Amsterdam. NL., 877(31):4065-4070.
Bowie, James, U., et al. (1990) "Deciphering the Message in Protein Sequences: Tolerance to Amino Acid Substitutions", Science, 247:1306-1310.
Burgess, Wilson, H., et al. (1990) "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue", J. Cell Bioi., 111:2129-2138.
Bork, Peer, (2000) "Powers and Pitfalls in Sequence Analysis: The 70% Hurdle", Genome Research, 10:398-400.
Lazar, Eliane, et al. (1988) "Transforming Growth Factor alpha: Mutation of Aspartic Acid 47 and Leucine 48 Results in Different Biological Activities", Mol. Cell. Bioi., 8:1247-1252.
UniProt reference P79338 (1L 1 O_MACFA) (downloaded from http://www.uniprot.org/uniprot/P79338, last sequence update May 1, 1997).
UniProt reference A2T6Z6 (1L 1 O_PANTR) (downloaded from http://www.uniprot.org/uniprot!A2T6Z6, last sequence update Mar. 6, 2007).
Soderquist, et al. (2010) "PEGylation of interleukin-1 0 for the mitigation of enhanced pain states", J Biomed Mater Res A, 3(93):1169-1179.
Chang, et al., (2017) "CARs: Synthetic immunoreceptors for cancer therapy and beyond", Trends Mol. Med., 23:430-450.
Hermanson, et al., (2015) "Utilizing chimeric antigen receptors to direct natural killer cell activity", Frontiers in Immunology, 6:195.
Jaspers, et al., (2017) "Development of CART cells designed to improve antitumor efficacy and safety", Pharmac. & Therap., http://dx.doi.org/1 0.1 016/j.pharmthera.2017.03.012.
Jensen, et al., (2015) "Designing chimeric antigen receptors to effectively and safely target tumors", Curr. Opin. Immunol., 33:9-15.
Chmielewski, et al, (2015) "TRUCKs: the fourth generation of CARs", Exp. Opin. Bioi. Ther., 15:1145-1154.
Hombach, et al., (2012) "OX40 costimulation by a chimeric antigen receptor abrogates CD28 and IL-2 induced IL-10 secretion by redirected CD4+ T cells", OncoImmunol., 1:458-466.
Newick, et al., (2016) "CART cell therapy for solid tumors", Annu. Rev. Med., 68:139-152.
Gillet, et al., (2015) "Going Viral: chimeric antigen receptor T-cell therapy for hematological malignancies", Immunol. Rev., 263:68-89.
Aukrust et al., (2005) "Potential role for immunomodulatory therapy in atherosclerotic plaque stabilization", Expert Opinion Pharmacother, 6:2169-2180.
Cheon, H.G. (2013) "Latest research and development trends in non insulin anti-diabetics", Arch. Pharm. Res., 36:145-153.
Fichtlscherer et al., (2004) "Interleukin-10 serum levels and systemic endothelial vasoreactivity in patients with coronary artery desease", J. Am. Coll. Cardiol., 44:44-49.
Dinant, et al., (2007) "IL-10 attenuates hepatic I/R injury and promotes hepatocyte proliferation", J. Surg. Res., 141:176-182.
Gotoh, et al., (2012) "A novel anti-inflammatory role for spleen-derived Interleukin-10 in obesity-induced inflammation in white adipose tissue and liver", Diabetes, 61:1994-2003.
Kumagai, et al., (2013) "Effects of Ezetimibe on hypercholesterolemia in the lipid profile in patients with metabolic syndrome", IJC Metabolic and Endocrine, 1:7-12.
Mumm, John B., et al. "IL-10 Elicits IFNy-Dependent Tumor Immune Surveillance", Cancer Cell, 2011, 20:781-796.
Sinha, Ian, et al. "A Systematic Review of Studies That Aim to Determine Which Outcomes to Measure in Clinical Trials in Children", PLOS:One, Apr. 29, 2008, 13 pages.
Mauri, Massimo C., et al., (2007) "Clinical Pharmacokinetics of Atypical Antipsychotics" Clinical Pharmacokinetics, 46(5):359-388.
FDA: Limit Use of 80 mg Simvastatin, Jun. 8, 2011, (https://www.fda.gov/ForConsumers/ConsumerUpdates/ucm257884.htm) 3 pages.
Bruserud, O., et al., (1995) "Effects of interleukin 10 on blast cells derived from patients with acute myelogenous leukemia", Leukemia, 9:1910-1920.

\* cited by examiner

FIG. 1

Human IL-10 (NP_000563) (SEQ ID NO://):

| | |
|---|---|
| 1 | mhssallccl vlltgvrasp gqgtqsensc thfpgnlpnm lrdlrdafsr vktffqmkdq |
| 61 | ldnlllkesl ledfkgylgc qalsemiqfy leevmpqaen qdpdikahvn slgenlktlr |
| 121 | lrlrrchrfl pcenkskave qvknafnklq ekgiykamse fdifinyiea ymtmkirn |

Mouse IL-10 (NP_034678) (SEQ ID NO://):

| | |
|---|---|
| 1 | mpgsallccl llltgmrisr gqysrednnc thfpvgqshm llelrtafsq vktffqtkdq |
| 61 | ldnilltdsl mqdfkgylgc qalsemiqfy lvevmpqaek hgpeikehln slgeklktlr |
| 121 | mrlrrchrfl pcenkskave qvksdfnklq dqgvykamne fdifinciea ymmikmks |

METHODS OF USING PEGYLATED INTERLEUKIN-10 FOR TREATING CANCER

CROSS-REFERENCE TO RELATED APPLICATION

This application claims priority benefit of U.S. provisional application Ser. No. 61/813,563, filed Apr. 18, 2013, which application is incorporated herein by reference in its entirety.

FIELD OF THE INVENTION

This invention relates to methods of using IL-10 and related agents in the treatment or prevention of a diverse array of diseases and disorders.

INTRODUCTION

The cytokine interleukin-10 (IL-10) is a pleiotropic cytokine that regulates multiple immune responses through actions on T cells, B cells, macrophages, and antigen presenting cells (APC). IL-10 may suppress immune responses by inhibiting expression of IL-1α, IL-1β, IL-6, IL-8, TNF-α, GM-CSF and G-CSF in activated monocytes and activated macrophages, and it also suppresses IFN-γ production by NK cells. Although IL-10 is predominantly expressed in macrophages, expression has also been detected in activated T cells, B cells, mast cells, and monocytes. In addition to suppressing immune responses, IL-10 exhibits immunostimulatory properties, including stimulating the proliferation of IL-2- and IL-4-treated thymocytes, enhancing the viability of B cells, and stimulating the expression of MHC class II.

Human IL-10 is a homodimer that becomes biologically inactive upon disruption of the non-covalent interactions between the two monomer subunits. Data obtained from the published crystal structure of IL-10 indicates that the functional dimer exhibits certain similarities to IFN-γ (Zdanov et al, (1995) Structure (Lond) 3:591-601).

As a result of its pleiotropic activity, IL-10 has been linked to a broad range of diseases, disorders and conditions, including inflammatory conditions, immune-related disorders, fibrotic disorders and cancer. Clinical and pre-clinical evaluations with IL-10 for a number of such diseases, disorders and conditions have solidified its therapeutic potential. Moreover, pegylated IL-10 has been shown to be more efficacious than non-pegylated IL-10 in certain therapeutic settings.

In view of the prevalence and severity of IL-10-associated diseases, disorders and conditions, novel dosing regimens and parameters that optimize efficacy, patient tolerance and the like would be of tremendous value in furthering the therapeutic usefulness of IL-10 and pegylated IL-10, and agents related thereto.

SUMMARY

The present disclosure contemplates methods of using IL-10, modified (e.g., pegylated) IL-10, and associated agents described herein, and compositions thereof, to treat and/or prevent various diseases, disorders and conditions, and/or the symptoms thereof. More particularly, the present disclosure relates to optimized dosing parameters to achieve and maintain efficacy in the treatment and/or prevention of various diseases, disorders and conditions in a subject, while minimizing the adverse effects associated therewith. As set forth in the in detail hereafter, such optimization of dosing parameters involves, for example, the assessment of pharmacokinetic and pharmacodynamic parameters associated with absorption, distribution, metabolism, and excretion ("ADME"), taking into consideration the route of administration and other factors. It is understood that, unless indicated otherwise herein, terms related to ADME and other parameters are intended to have their ordinary accepted meanings in the relevant scientific fields. By way of example, the terms "serum half-life" or "$t_{1/2}$" refer to elimination half-life (i.e., the time at which the serum concentration of an agent has reached one-half of its initial or maximum value).

According to the methods described herein, the disease, disorder or condition, and/or symptoms thereof, may be a proliferative disorder, such as cancer or a cancer-related disorder, or a fibrotic disorder, such as cirrhosis, NASH and NAFLD. Though not limited to particular cancers, the cancer may be a solid tumor, including tumors associated with colon cancer, melanoma, and squamous cell carcinoma, or it may be a hematological disorder.

In other embodiments, the disease, disorder or condition is a viral disorder, including, but not limited to, human immunodeficiency virus, hepatitis B or C virus or cytomegalovirus. In still further embodiments, the disease, disorder or condition is an immune or inflammatory disorder, which may be acute or chronic. Examples of immune and inflammatory disorders include inflammatory bowel disease, psoriasis, rheumatoid arthritis, multiple sclerosis, and Alzheimer's disease.

In particular embodiments, the disease, disorder or condition is a cardiovascular disorder, including atherosclerosis. The subject having a cardiovascular disorder may have elevated cholesterol.

In still further embodiments, the disease, disorder or condition is thrombosis or a thrombotic condition.

As discussed further hereafter, human IL-10 is a homodimer and each monomer comprises 178 amino acids, the first 18 of which comprise a signal peptide. Particular embodiments of the present disclosure comprise mature human IL-10 polypeptides lacking the signal peptide (see, e.g., U.S. Pat. No. 6,217,857), or mature human PEG-IL-10. In further particular embodiments, the IL-10 agent is a variant of mature human IL-10. The variant may exhibit activity less than, comparable to, or greater than the activity of mature human IL-10; in certain embodiments the activity is comparable to or greater than the activity of mature human IL-10.

Certain embodiments of the present disclosure contemplate modification of IL-10 in order to enhance one or more properties (e.g., pharmacokinetic parameters, efficacy, etc.). In particular embodiments, IL-10 is modified by, for example, pegylation, glycosylation, albumin (e.g., human serum albumin (HSA)) conjugation, and hesylation. In further embodiments, modification of IL-10 does not result in a therapeutically relevant, detrimental effect on immunogenicity, and in still further embodiments modified IL-10 is less immunogenic than unmodified IL-10. The terms "IL-10", "IL-10 polypeptide(s)," "agent(s)" and the like are intended to be construed broadly and include, for example, human and non-human IL-10-related polypeptides, including homologs, variants (including muteins), and fragments thereof, as well as IL-10 polypeptides having, for example, a leader sequence (e.g., the signal peptide), and modified versions of the foregoing. In further particular embodiments, the terms "IL-10", "IL-10 polypeptide(s), "agent(s)" are agonists. Particular embodiments relate to pegylated IL-10, which is also referred to herein as "PEG-IL-10". The present disclosure also contemplates nucleic acid molecules encoding the foregoing.

Particular embodiments of the present disclosure relate to methods of treating or preventing a disease, disorder or condition in a subject, comprising administering to the subject a therapeutically effective amount of an IL-10 agent, wherein the amount is sufficient to achieve a mean IL-10 serum trough concentration of at least 0.1 ng/mL. The methods of treating or preventing may be mediated by CD8+ T cells.

Other embodiments relate to methods of treating or preventing a disease, disorder or condition in a subject (e.g., a human), comprising administering to the subject a therapeutically effective amount of an IL-10 agent, wherein the amount is sufficient to maintain a mean IL-10 serum trough concentration over a period of time, wherein the mean IL-10 serum trough concentration is at least 0.1 ng/mL, and wherein the mean IL-10 serum trough concentration is maintained for at least 90% of the period of time. In particular embodiments of the present disclosure, the mean IL-10 serum trough concentration is at least 0.2 ng/mL, at least 0.3 ng/mL, and least 0.4 ng/mL, at least 0.5 ng/mL, at least 0.6 ng/mL, at least 0.7 ng/mL, at least 0.8 ng/mL, at least 0.9 ng/mL, at least 1 ng/mL, at least 1.2 ng/mL, at least 1.25 ng/mL, at least 1.3 ng/mL, at least 1.4 ng/mL, at least 1.5 ng/mL, at least 1.6 ng/mL, at least 1.7 ng/mL, at least 1.8 ng/mL, at least 1.85 ng/mL, at least 1.9 ng/mL, at least 1.95 ng/mL, at least 1.97 ng/mL, and least 1.98 ng/mL, at least 1.99 ng/mL, at least 2.0 ng/mL or greater than 2 ng/mL.

In further embodiments, the period of time is at least 12 hours, at least 24 hours, at least 48 hours, at least 72 hours, at least 1 week, at least 2 weeks, at least 3 weeks, at least 1 month, at least 6 weeks, at least 2 months, at least 3 months, or greater than 3 months.

In particular embodiments of the present disclosure, the mean IL-10 serum trough concentration is maintained for at least 85% of the period of time, at least 90%, at least 95%, at least 98%, at least 99% or 100% of the period of time.

It is envisaged that a dosing regimen sufficient to maintain a desired steady state serum trough concentration (e.g., 0.1 ng/mL or 2 ng/mL) may result in an initial serum trough concentration that is higher than the desired steady state serum trough concentration. Because of the pharmacodynamic and pharmacokinetic characteristics of IL-10 in a mammalian subject, an initial trough concentration (achieved, for example, through the administration of one or more loading doses followed by a series of maintenance doses) gradually but continually decreases over a period of time even when the dosing parameters (amount and frequency) are kept constant. After that period of time, the gradual but continual decrease ends and a steady state serum trough concentration is maintained.

By way of example, parenteral administration (e.g., SC and IV) of ~0.1 mg/kg/day of an IL-10 agent (e.g., mIL-10) to a mouse (e.g., a C57BL/6 mouse) is required to maintain a steady state serum trough concentration of, for example, 2.0 ng/mL. However, that steady state serum trough concentration may not be achieved until approximately 30 days after initiation of dosing at 0.1 mg/kg/day (and also after any loading dose(s)). Rather, after an initial serum trough concentration has been achieved (e.g., 2.5 ng/mL), that concentration gradually but continually decreases over the course of, for example, the approximately 30-day period, after which time the desired steady state serum trough concentration (e.g., 2.0 ng/mL) is maintained. One of skill in the art will be able to determine the dose needed to maintain the desired steady state trough concentration using, for example, ADME and patient-specific parameters.

The present disclosure contemplates methods wherein the IL-10 agent may comprise at least one modification to form a modified IL-10 agent, wherein the modification does not alter the amino acid sequence of the IL-10 agent. In some embodiments, the modified IL-10 agent is a PEG-IL-10 agent. The PEG-IL-10 agent may comprise at least one PEG molecule covalently attached to at least one amino acid residue of at least one subunit of IL-10 or comprise a mixture of mono-pegylated and di-pegylated IL-10 in other embodiments. The PEG component of the PEG-IL-10 agent may have a molecular mass greater than about 5 kDa, greater than about 10 kDa, greater than about 15 kDa, greater than about 20 kDa, greater than about 30 kDa, greater than about 40 kDa, or greater than about 50 kDa. In some embodiments, the molecular mass is from about 5 kDa to about 10 kDa, from about 5 kDa to about 15 kDa, from about 5 kDa to about 20 kDa, from about 10 kDa to about 15 kDa, from about 10 kDa to about 20 kDa, from about 10 kDa to about 25 kDa or from about 10 kDa to about 30 kDa.

In some embodiments, the modified IL-10 agent comprises at least one Fc fusion molecule, at least one serum albumin (e.g., HSA or BSA), an HSA fusion molecule or an albumin conjugate. In additional embodiments, the modified IL-10 agent is glycosylated, is hesylated, or comprises at least one albumin binding domain. Some modified IL-10 agents may comprise more than one type of modification. In particular embodiments, the modification is site-specific. Some embodiments comprise a linker. Modified IL-10 agents are discussed in detail hereafter.

The present disclosure also contemplates the use of gene therapy in conjunction with the teachings herein. For gene therapy uses and methods, a cell in a subject can be transformed with a nucleic acid that encodes an IL-10-related polypeptide as set forth herein in vivo. Alternatively, a cell can be transformed in vitro with a transgene or polynucleotide, and then transplanted into a tissue of subject in order to effect treatment. In addition, a primary cell isolate or an established cell line can be transformed with a transgene or polynucleotide that encodes an IL-10-related polypeptide, and then optionally transplanted into a tissue of a subject.

The present disclosure contemplates methods wherein the IL-10 agent is administered to the subject at least twice daily, at least once daily, at least once every 48 hours, at least once every 72 hours, at least once weekly, at least once every 2 weeks, at least once monthly, at least once every 2 months, or at least once every 3 months. Some embodiments also comprise administering the IL-10 agent with at least one additional prophylactic or therapeutic agent, examples of which are set forth hereafter.

The IL-10 agent may be administered by any effective route. In some embodiments, it is administered by parenteral injection, including subcutaneous injection.

Particular embodiments of the present disclosure relate to pharmaceutical compositions comprising an amount of an IL-10 agent (e.g., a therapeutically effective amount), including those agents described above, along with one or more pharmaceutically acceptable diluent, carrier or excipient (e.g., an isotonic injection solution). The pharmaceutical composition is generally one that is suitable for human administration. Furthermore, in some embodiments the pharmaceutical composition comprises at least one additional prophylactic or therapeutic agent.

Certain embodiments of the present disclosure contemplate a sterile container that contains one of the above-mentioned pharmaceutical compositions and optionally one or more additional components. By way of example, but not limitation, the sterile container may be a syringe. In still further embodiments, the sterile container is one component of a kit; the kit may also contain, for example, a second sterile container that comprises at least one prophylactic or therapeutic agent.

BRIEF DESCRIPTION OF THE DRAWINGS

FIG. 1 depicts the amino acid sequences of human and mouse IL-10.

DETAILED DESCRIPTION

Figure 2A:
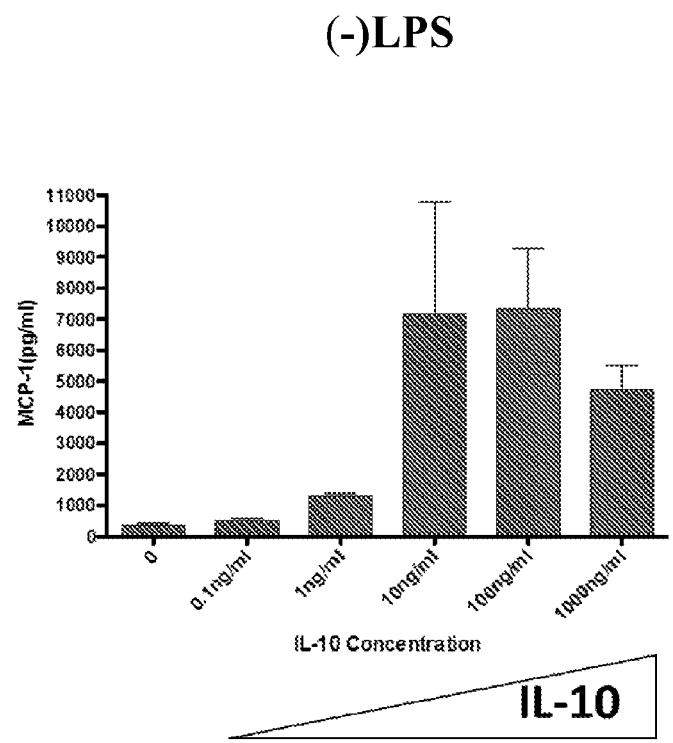
FIG. 2A depicts the concentration of MCP-1 (pg/mL) in PBMCs at increasing concentrations of IL-10. At concentrations of 1 ng/mL and above, IL-10 increased the secretion of MCP-1.

Before the present disclosure is further described, it is to be understood that the disclosure is not limited to the particular embodiments set forth herein, and it is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention. Unless defined otherwise, all technical and scientific terms used herein have the same meaning as commonly understood by one of ordinary skill in the art to which this invention belongs.

It must be noted that as used herein and in the appended claims, the singular forms "a," "an," and "the" include plural referents unless the context clearly dictates otherwise. It is further noted that the claims may be drafted to exclude any optional element. As such, this statement is intended to serve as antecedent basis for use of such exclusive terminology such as "solely," "only" and the like in connection with the recitation of claim elements, or use of a "negative" limitation.

The publications discussed herein are provided solely for their disclosure prior to the filing date of the present application. Further, the dates of publication provided may be different from the actual publication dates, which may need to be independently confirmed.

Overview

The present disclosure contemplates the use of the agents described herein, and compositions thereof, to treat and/or prevent various diseases, disorders and conditions, and/or the symptoms thereof. In certain aspects of the present disclosure, such treatment or prevention is effected by utilizing particular dosing parameters. In some embodiments the agents are administered so as to achieve a serum trough concentration that is optimized for treating, for example, inflammatory- and immune-related disorders, fibrotic disorders, cancer and cancer-related disorders, or cardiovascular disorders (e.g., atherosclerosis).

In some embodiments of the present disclosure, a subject having, or at risk of having, a disease or disorder treatable by an IL-10 agent (e.g., an IL-10 polypeptide) is administered the IL-10 agent in an amount sufficient to achieve a serum trough concentration greater than about 0.1 ng/mL, in certain embodiments the serum trough concentration is greater than about 1 ng/mL, whereas in other embodiments the serum trough concentration is greater than about 2 ng/mL.

It should be noted that any reference to "human" in connection with the polypeptides and nucleic acid molecules of the present disclosure is not meant to be limiting with respect to the manner in which the polypeptide or nucleic acid is obtained or the source, but rather is only with reference to the sequence as it may correspond to a sequence of a naturally occurring human polypeptide or nucleic acid molecule. In addition to the human polypeptides and the nucleic acid molecules which encode them, the present disclosure contemplates IL-10-related polypeptides and corresponding nucleic acid molecules from other species.

Definitions

Unless otherwise indicated, the following terms are intended to have the meaning set forth below. Other terms are defined elsewhere throughout the specification.

The terms "patient" or "subject" are used interchangeably to refer to a human or a non-human animal (e.g., a mammal).

The terms "administration", "administer" and the like, as they apply to, for example, a subject, cell, tissue, organ, or biological fluid, refer to contact of, for example, IL-10 or PEG-IL-10, a nucleic acid (e.g., a nucleic acid encoding native human IL-10); a pharmaceutical composition comprising the foregoing, or a diagnostic agent to the subject, cell, tissue, organ, or biological fluid. In the context of a cell, administration includes contact (e.g., in vitro or ex vivo) of a reagent to the cell, as well as contact of a reagent to a fluid, where the fluid is in contact with the cell.

The terms "treat", "treating", treatment" and the like refer to a course of action (such as administering IL-10 or a pharmaceutical composition comprising IL-10) initiated after a disease, disorder or condition, or a symptom thereof, has been diagnosed, observed, and the like so as to eliminate, reduce, suppress, mitigate, or ameliorate, either temporarily or permanently, at least one of the underlying causes of a disease, disorder, or condition afflicting a subject, or at least one of the symptoms associated with a disease, disorder, or condition afflicting a subject. Thus, treatment includes inhibiting (e.g., arresting the development or further development of the disease, disorder or condition or clinical symptoms association therewith) an active disease. The terms may also be used in other contexts, such as situations where IL-10 or PEG-IL-10 contacts an IL-10 receptor in, for example, the fluid phase or colloidal phase.

The term "in need of treatment" as used herein refers to a judgment made by a physician or other caregiver that a subject requires or will benefit from treatment. This judgment is made based on a variety of factors that are in the realm of the physician's or caregiver's expertise.

The terms "prevent", "preventing", "prevention" and the like refer to a course of action (such as administering IL-10 or a pharmaceutical composition comprising IL-10) initiated in a manner (e.g., prior to the onset of a disease, disorder, condition or symptom thereof) so as to prevent, suppress, inhibit or reduce, either temporarily or permanently, a subject's risk of developing a disease, disorder, condition or the like (as determined by, for example, the absence of clinical symptoms) or delaying the onset thereof, generally in the context of a subject predisposed to having a particular disease, disorder or condition. In certain instances, the terms also refer to slowing the progression of the disease, disorder or condition or inhibiting progression thereof to a harmful or otherwise undesired state.

The term "in need of prevention" as used herein refers to a judgment made by a physician or other caregiver that a subject requires or will benefit from preventative care. This judgment is made based on a variety of factors that are in the realm of a physician's or caregiver's expertise.

The phrase "therapeutically effective amount" refers to the administration of an agent to a subject, either alone or as part of a pharmaceutical composition and either in a single dose or as part of a series of doses, in an amount capable of having any detectable, positive effect on any symptom, aspect, or characteristic of a disease, disorder or condition when administered to the subject. The therapeutically effective amount can be ascertained by measuring relevant physiological effects, and it can be adjusted in connection with the dosing regimen and diagnostic analysis of the subject's condition, and the like. By way of example, measurement of the amount of inflammatory cytokines produced following administration may be indicative of whether a therapeutically effective amount has been used.

The phrase "in a sufficient amount to effect a change" means that there is a detectable difference between a level of an indicator measured before (e.g., a baseline level) and after administration of a particular therapy. Indicators include any objective parameter (e.g., serum concentration of IL-10) or subjective parameter (e.g., a subject's feeling of well-being).

The term "small molecules" refers to chemical compounds having a molecular weight that is less than about 10 kDa, less than about 2 kDa, or less than about 1 kDa. Small molecules include, but are not limited to, inorganic molecules, organic molecules, organic molecules containing an inorganic component, molecules comprising a radioactive atom, and synthetic molecules. Therapeutically, a small molecule may be more permeable to cells, less susceptible to degradation, and less likely to elicit an immune response than large molecules.

The term "ligand" refers to, for example, a peptide, polypeptide, membrane-associated or membrane-bound molecule, or complex thereof, that can act as an agonist or antagonist of a receptor. "Ligand" encompasses natural and synthetic ligands, e.g., cytokines, cytokine variants, analogs, muteins, and binding compositions derived from antibodies. "Ligand" also encompasses small molecules, e.g., peptide mimetics of cytokines and peptide mimetics of antibodies. The term also encompasses an agent that is neither an agonist nor antagonist, but that can bind to a receptor without significantly influencing its biological properties, e.g., signaling or adhesion. Moreover, the term includes a membrane-bound ligand that has been changed, e.g., by chemical or recombinant methods, to a soluble version of the membrane-bound ligand. A ligand or receptor may be entirely intracellular, that is, it may reside in the cytosol, nucleus, or some other intracellular compartment. The complex of a ligand and receptor is termed a "ligand-receptor complex".

The terms "inhibitors" and "antagonists", or "activators" and "agonists" refer to inhibitory or activating molecules, respectively, for example, for the activation of, e.g., a ligand, receptor, cofactor, gene, cell, tissue, or organ Inhibitors are molecules that decrease, block, prevent, delay activation, inactivate, desensitize, or down-regulate, e.g., a gene, protein, ligand, receptor, or cell. Activators are molecules that increase, activate, facilitate, enhance activation, sensitize, or up-regulate, e.g., a gene, protein, ligand, receptor, or cell. An inhibitor may also be defined as a molecule that reduces, blocks, or inactivates a constitutive activity. An "agonist" is a molecule that interacts with a target to cause or promote an increase in the activation of the target. An "antagonist" is a molecule that opposes the action(s) of an agonist. An antagonist prevents, reduces, inhibits, or neutralizes the activity of an agonist, and an antagonist can also prevent, inhibit, or reduce constitutive activity of a target, e.g., a target receptor, even where there is no identified agonist.

The terms "modulate", "modulation" and the like refer to the ability of a molecule (e.g., an activator or an inhibitor) to increase or decrease the function or activity of an IL-10 agent (or the nucleic acid molecules encoding them), either directly or indirectly; or to enhance the ability of a molecule to produce an effect comparable to that of an IL-10 agent. The term "modulator" is meant to refer broadly to molecules that can effect the activities described above. By way of example, a modulator of, e.g., a gene, a receptor, a ligand, or a cell, is a molecule that alters an activity of the gene, receptor, ligand, or cell, where activity can be activated, inhibited, or altered in its regulatory properties. A modulator may act alone, or it may use a cofactor, e.g., a protein, metal ion, or small molecule. The term "modulator" includes agents that operate through the same mechanism of action as IL-10 (i.e., agents that modulate the same signaling pathway as IL-10 in a manner analogous thereto) and are capable of eliciting a biological response comparable to (or greater than) that of IL-10.

Examples of modulators include small molecule compounds and other bioorganic molecules. Numerous libraries of small molecule compounds (e.g., combinatorial libraries) are commercially available and can serve as a starting point for identifying a modulator. The skilled artisan is able to develop one or more assays (e.g., biochemical or cell-based assays) in which such compound libraries can be screened in order to identify one or more compounds having the desired properties; thereafter, the skilled medicinal chemist is able to optimize such one or more compounds by, for example, synthesizing and evaluating analogs and derivatives thereof. Synthetic and/or molecular modeling studies can also be utilized in the identification of an Activator.

The "activity" of a molecule may describe or refer to the binding of the molecule to a ligand or to a receptor; to catalytic activity; to the ability to stimulate gene expression or cell signaling, differentiation, or maturation; to antigenic activity; to the modulation of activities of other molecules; and the like. The term may also refer to activity in modulating or maintaining cell-to-cell interactions (e.g., adhesion), or activity in maintaining a structure of a cell (e.g., a cell membrane). "Activity" can also mean specific activity, e.g., [catalytic activity]/[mg protein], or [immunological activity]/[mg protein], concentration in a biological compartment, or the like. The term "proliferative activity" encompasses an activity that promotes, that is necessary for, or that is specifically associated with, for example, normal cell division, as well as cancer, tumors, dysplasia, cell transformation, metastasis, and angiogenesis.

As used herein, "comparable", "comparable activity", "activity comparable to", "comparable effect", "effect comparable to", and the like are relative terms that can be viewed quantitatively and/or qualitatively. The meaning of the terms is frequently dependent on the context in which they are used. By way of example, two agents that both activate a receptor can be viewed as having a comparable effect from a qualitative perspective, but the two agents can be viewed as lacking a comparable effect from a quantitative perspective if one agent is only able to achieve 20% of the activity of the other agent as determined in an art-accepted assay (e.g., a dose-response assay) or in an art-accepted animal model. When comparing one result to another result (e.g., one result to a reference standard), "comparable" frequently means that one result deviates from a reference standard by less than 35%, by less than 30%, by less than 25%, by less than 20%, by less than 15%, by less than 10%, by less than 7%, by less than 5%, by less than 4%, by less than 3%, by less than 2%, or by less than 1%. In particular embodiments, one result is comparable to a reference standard if it deviates by less than 15%, by less than 10%, or by less than 5% from the reference standard. By way of example, but not limitation, the activity or effect may refer to efficacy, stability, solubility, or immunogenicity.

The term "response," for example, of a cell, tissue, organ, or organism, encompasses a change in biochemical or physiological behavior, e.g., concentration, density, adhesion, or migration within a biological compartment, rate of gene expression, or state of differentiation, where the change is correlated with activation, stimulation, or treatment, or with internal mechanisms such as genetic programming. In certain contexts, the terms "activation", "stimulation", and the like refer to cell activation as regulated by internal mechanisms, as well as by external or environmental factors; whereas the terms "inhibition", "down-regulation" and the like refer to the opposite effects.

The terms "polypeptide," "peptide," and "protein", used interchangeably herein, refer to a polymeric form of amino acids of any length, which can include genetically coded and non-genetically coded amino acids, chemically or biochemically modified or derivatized amino acids, and polypeptides having modified polypeptide backbones. The terms include fusion proteins, including, but not limited to, fusion proteins with a heterologous amino acid sequence; fusion proteins with heterologous and homologous leader sequences; fusion proteins with or without N-terminus methionine residues; fusion proteins with immunologically tagged proteins; and the like.

It will be appreciated that throughout this disclosure reference is made to amino acids according to the single letter or three letter codes. For the reader's convenience, the single and three letter amino acid codes are provided below:

| G | Glycine       | Gly | P | Proline       | Pro |
|---|---------------|-----|---|---------------|-----|
| A | Alanine       | Ala | V | Valine        | Val |
| L | Leucine       | Leu | I | Isoleucine    | Ile |
| M | Methionine    | Met | C | Cysteine      | Cys |
| F | Phenylalanine | Phe | Y | Tyrosine      | Tyr |
| W | Tryptophan    | Trp | H | Histidine     | His |
| K | Lysine        | Lys | R | Arginine      | Arg |
| Q | Glutamine     | Gln | N | Asparagine    | Asn |
| E | Glutamic Acid | Glu | D | Aspartic Acid | Asp |
| S | Serine        | Ser | T | Threonine     | Thr |

As used herein, the term "variant" encompasses naturally-occurring variants and non-naturally-occurring variants. Naturally-occurring variants include homologs (polypeptides and nucleic acids that differ in amino acid or nucleotide sequence, respectively, from one species to another), and allelic variants (polypeptides and nucleic acids that differ in amino acid or nucleotide sequence, respectively, from one individual to another within a species). Non-naturally-occurring variants include polypeptides and nucleic acids that comprise a change in amino acid or nucleotide sequence, respectively, where the change in sequence is artificially introduced (e.g., muteins); for example, the change is generated in the laboratory by human intervention ("hand of man"). Thus, herein a "mutein" refers broadly to mutated recombinant proteins that usually carry single or multiple amino acid substitutions and are frequently derived from cloned genes that have been subjected to site-directed or random mutagenesis, or from completely synthetic genes.

The terms "DNA", "nucleic acid", "nucleic acid molecule", "polynucleotide" and the like are used interchangeably herein to refer to a polymeric form of nucleotides of any length, either deoxyribonucleotides or ribonucleotides, or analogs thereof. Non-limiting examples of polynucleotides include linear and circular nucleic acids, messenger RNA (mRNA), complementary DNA (cDNA), recombinant polynucleotides, vectors, probes, primers and the like.

As used herein in the context of the structure of a polypeptide, "N-terminus" (or "amino terminus") and "C-terminus" (or "carboxyl terminus") refer to the extreme amino and carboxyl ends of the polypeptide, respectively, while the terms "N-terminal" and "C-terminal" refer to relative positions in the amino acid sequence of the polypeptide toward the N-terminus and the C-terminus, respectively, and can include the residues at the N-terminus and C-terminus, respectively. "Immediately N-terminal" or "immediately C-terminal" refers to a position of a first amino acid residue relative to a second amino acid residue where the first and second amino acid residues are covalently bound to provide a contiguous amino acid sequence.

"Derived from", in the context of an amino acid sequence or polynucleotide sequence (e.g., an amino acid sequence "derived from" an IL-10 polypeptide), is meant to indicate that the polypeptide or nucleic acid has a sequence that is based on that of a reference polypeptide or nucleic acid (e.g., a naturally occurring IL-10 polypeptide or an IL-10-encoding nucleic acid), and is not meant to be limiting as to the source or method in which the protein or nucleic acid is made. By way of example, the term "derived from" includes homologs or variants of reference amino acid or DNA sequences.

In the context of a polypeptide, the term "isolated" refers to a polypeptide of interest that, if naturally occurring, is in an environment different from that in which it may naturally occur. "Isolated" is meant to include polypeptides that are within samples that are substantially enriched for the polypeptide of interest and/or in which the polypeptide of interest is partially or substantially purified. Where the polypeptide is not naturally occurring, "isolated" indicates that the polypeptide has been separated from an environment in which it was made by either synthetic or recombinant means.

"Enriched" means that a sample is non-naturally manipulated (e.g., by a scientist) so that a polypeptide of interest is present in a) a greater concentration (e.g., at least 3-fold greater, at least 4-fold greater, at least 8-fold greater, at least 64-fold greater, or more) than the concentration of the polypeptide in the starting sample, such as a biological sample (e.g., a sample in which the polypeptide naturally occurs or in which it is present after administration), or b) a concentration greater than the environment in which the polypeptide was made (e.g., as in a bacterial cell).

"Substantially pure" indicates that a component (e.g., a polypeptide) makes up greater than about 50% of the total content of the composition, and typically greater than about 60% of the total polypeptide content. More typically, "substantially pure" refers to compositions in which at least 75%, at least 85%, at least 90% or more of the total composition is the component of interest. In some cases, the polypeptide will make up greater than about 90%, or greater than about 95% of the total content of the composition.

The terms "specifically binds" or "selectively binds", when referring to a ligand/receptor, antibody/antigen, or other binding pair, indicates a binding reaction which is determinative of the presence of the protein in a heterogeneous population of proteins and other biologics. Thus, under designated conditions, a specified ligand binds to a particular receptor and does not bind in a significant amount to other proteins present in the sample. The antibody, or binding composition derived from the antigen-binding site of an antibody, of the contemplated method binds to its antigen, or a variant or mutein thereof, with an affinity that is at least two-fold greater, at least ten times greater, at least 20-times greater, or at least 100-times greater than the affinity with any other antibody, or binding composition derived therefrom. In a particular embodiment, the antibody will have an affinity that is greater than about $10^9$ liters/mol, as determined by, e.g., Scatchard analysis (Munsen, et al. 1980 Analyt. Biochem. 107:220-239).

IL-10 and PEG-IL-10

The anti-inflammatory cytokine IL-10, also known as human cytokine synthesis inhibitory factor (CSIF), is classified as a type(class)-2 cytokine, a set of cytokines that includes IL-19, IL-20, IL-22, IL-24 (Mda-7), and IL-26, interferons (IFN-α, -β, -γ, -δ, -ε, -κ, -Ω, and -τ) and interferon-like molecules (limitin, IL-28A, IL-28B, and IL-29).

IL-10 is a cytokine with pleiotropic effects in immunoregulation and inflammation. It is produced by mast cells, counteracting the inflammatory effect that these cells have at the site of an allergic reaction. While it is capable of inhibiting the synthesis of pro-inflammatory cytokines such as IFN-γ, IL-2, IL-3, TNFα and GM-CSF, IL-10 is also stimulatory towards certain T cells and mast cells and stimulates B-cell maturation, proliferation and antibody production. IL-10 can block NF-κB activity and is involved in the regulation of the JAK-STAT signaling pathway. It also induces the cytotoxic activity of CD8+ T-cells and the antibody production of B-cells, and it suppresses macrophage activity and tumor-promoting inflammation. The regulation of CD8+ T-cells is dose-dependent, wherein higher doses induce stronger cytotoxic responses.

Human IL-10 is a homodimer with a molecular mass of 37 kDa, wherein each 18.5 kDa monomer comprises 178 amino acids, the first 18 of which comprise a signal peptide, and two pairs of cysteine residues that form two intramolecular disulfide bonds. The IL-10 dimer becomes biologically inactive upon disruption of the non-covalent interactions between the two monomer subunits.

The present disclosure contemplates human IL-10 and murine IL-10, which exhibit 80% homology, and use thereof. In addition, the scope of the present disclosure includes IL-10 orthologs, and modified forms thereof, from other mammalian species, including rat (accession NP_036986.2; GI 148747382); cow (accession NP_776513.1; GI 41386772); sheep (accession NP_001009327.1; GI 57164347); dog (accession ABY86619.1; GI 166244598); and rabbit (accession AAC23839.1; GI 3242896).

As alluded to above, the terms "IL-10", "IL-10 polypeptide(s), "IL-10 agent(s)" and the like are intended to be broadly construed and include, for example, human and non-human IL-10-related polypeptides, including homologs, variants (including muteins), and fragments thereof, as well as IL-10 polypeptides having, for example, a leader sequence (e.g., the signal peptide), and modified versions of the foregoing. In further particular embodiments, IL-10, IL-10 polypeptide(s), and IL-10 agent(s) are agonists.

The IL-10 receptor, a type II cytokine receptor, consists of alpha and beta subunits, which are also referred to as R1 and R2, respectively. Receptor activation requires binding to both alpha and beta. One homodimer of an IL-10 polypeptide binds to alpha and the other homodimer of the same IL-10 polypeptide binds to beta.

The utility of recombinant human IL-10 is frequently limited by its relatively short serum half-life, which may be due to, for example, renal clearance, proteolytic degradation and monomerization in the blood stream. As a result, various approaches have been explored to improve the pharmacokinetic profile of IL-10 without disrupting its dimeric structure and thus adversely affecting its activity. Pegylation of IL-10 results in improvement of certain pharmacokinetic parameters (e.g., serum half-life) and/or enhancement of activity. For example, particular embodiments of the present disclosure involve methods of optimizing the treatment of proliferative disorders (e.g., cancer) with PEG-IL-10.

As previously indicated, the present disclosure also contemplates the use of gene therapy in conjunction with the teachings herein. Gene therapy is effected by delivering genetic material, usually packaged in a vector, to endogenous cells within a subject in order to introduce novel genes, to introduce additional copies of pre-existing genes, to impair the functioning of existing genes, or to repair existing but non-functioning genes. Once inside cells, the nucleic acid is expressed by the cell machinery, resulting in the production of the protein of interest. In the context of the present disclosure, gene therapy is used as a therapeutic to deliver nucleic acid that encodes an IL-10 agent for use in the treatment or prevention of a disease, disorder or condition described herein.

As alluded to above, for gene therapy uses and methods, a cell in a subject can be transformed with a nucleic acid that encodes an IL-10-related polypeptide as set forth herein in vivo. Alternatively, a cell can be transformed in vitro with a transgene or polynucleotide, and then transplanted into a tissue of subject in order to effect treatment. In addition, a primary cell isolate or an established cell line can be transformed with a transgene or polynucleotide that encodes an IL-10-related polypeptide, and then optionally transplanted into a tissue of a subject.

As used herein, the terms "pegylated IL-10" and PEG-IL-10" refer to an IL-10 molecule having one or more polyethylene glycol molecules covalently attached to at least one amino acid residue of the IL-10 protein, generally via a linker, such that the attachment is stable. The terms "monopegylated IL-10" and "mono-PEG-IL-10" indicate that one polyethylene glycol molecule is covalently attached to a single amino acid residue on one subunit of the IL-10 dimer, generally via a linker. In certain embodiments, the PEG-IL-10 used in the present disclosure is a mono-PEG-IL-10 in which one to nine PEG molecules are covalently attached via a linker to the alpha amino group of the amino acid residue at the N-terminus of one subunit of the IL-10 dimer. Monopegylation on one IL-10 subunit generally results in a non-homogeneous mixture of non-pegylated, monopegylated and dipegylated IL-10 due to subunit shuffling. Moreover, allowing a pegylation reaction to proceed to completion will generally result in non-specific and multi-pegylated IL-10, thus reducing its bioactivity. Thus, particular embodiments of the present disclosure comprise the administration of a mixture of mono- and di-pegylated IL-10 produced by the methods described herein (e.g., the Experimental section).

In particular embodiments, the average molecular weight of the PEG moiety is between about 5 kDa and about 50 kDa. Although the method or site of PEG attachment to IL-10 is not critical, in certain embodiments the pegylation does not alter, or only minimally alters, the activity of the IL-10 agent. In certain embodiments, the increase in half-life is greater than any decrease in biological activity. The biological activity of PEG-IL-10 is typically measured by assessing the levels of inflammatory cytokines (e.g., TNF-α or IFN-γ) in the serum of subjects challenged with a bacterial antigen (lipopolysaccharide (LPS)) and treated with PEG-IL-10, as described in U.S. Pat. No. 7,052,686.

IL-10 variants can be prepared with various objectives in mind, including increasing serum half-life, reducing an immune response against the IL-10, facilitating purification or preparation, decreasing conversion of IL-10 into its monomeric subunits, improving therapeutic efficacy, and lessening the severity or occurrence of side effects during therapeutic use. The amino acid sequence variants are usually predetermined variants not found in nature, although some may be post-translational variants, e.g., glycosylated variants. Any variant of IL-10 can be used provided it retains a suitable level of IL-10 activity. In the tumor context, suitable IL-10 activity includes, for example, CD8+ T cell infiltration into tumor sites, expression of inflammatory cytokines such as IFN-γ, IL-4, IL-6, IL-10, and RANK-L, from these infiltrating cells, and increased levels of IFN-γ in biological samples.

The phrase "conservative amino acid substitution" refers to substitutions that preserve the activity of the protein by replacing an amino acid(s) in the protein with an amino acid with a side chain of similar acidity, basicity, charge, polarity, or size of the side chain. Conservative amino acid substitutions generally entail substitution of amino acid residues within the following groups: 1) L, I, M, V, F; 2) R, K; 3) F, Y, H, W, R; 4) G, A, T, S; 5) Q, N; and 6) D, E. Guidance for substitutions, insertions, or deletions may be based on alignments of amino acid sequences of different variant proteins or proteins from different species. Thus, in addition to any naturally-occurring IL-10 polypeptide, the present disclosure contemplates having 1, 2, 3, 4, 5, 6, 7, 8, 9, or 10 usually no more than 20, 10, or 5 amino acid substitutions, where the substitution is usually a conservative amino acid substitution.

The present disclosure also contemplates active fragments (e.g., subsequences) of mature IL-10 containing contiguous amino acid residues derived from the mature IL-10. The length of contiguous amino acid residues of a peptide or a polypeptide subsequence varies depending on the specific naturally-occurring amino acid sequence from which the subsequence is derived. In general, peptides and polypeptides may be from about 20 amino acids to about 40 amino acids, from about 40 amino acids to about 60 amino acids, from about 60 amino acids to about 80 amino acids, from about 80 amino acids to about 100 amino acids, from about 100 amino acids to about 120 amino acids, from about 120 amino acids to about 140 amino acids, from about 140 amino acids to about 150 amino acids, from about 150 amino acids to about 155 amino acids, from about 155 amino acids up to the full-length peptide or polypeptide.

Additionally, IL-10 polypeptides can have a defined sequence identity compared to a reference sequence over a defined length of contiguous amino acids (e.g., a "comparison window"). Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Madison, Wis.), or by manual alignment and visual inspection (see, e.g., Current Protocols in Molecular Biology (Ausubel et al., eds. 1995 supplement)).

As an example, a suitable IL-10 polypeptide can comprise an amino acid sequence having at least about 75%, at least about 80%, at least about 85%, at least about 90%, at least about 95%, at least about 98%, or at least about 99%, amino acid sequence identity to a contiguous stretch of from about 20 amino acids to about 40 amino acids, from about 40 amino acids to about 60 amino acids, from about 60 amino acids to about 80 amino acids, from about 80 amino acids to about 100 amino acids, from about 100 amino acids to about 120 amino acids, from about 120 amino acids to about 140 amino acids, from about 140 amino acids to about 150 amino acids, from about 150 amino acids to about 155 amino acids, from about 155 amino acids up to the full-length peptide or polypeptide.

As discussed further below, the IL-10 polypeptides may be isolated from a natural source (e.g., an environment other than its naturally-occurring environment) and may also be recombinantly made (e.g., in a genetically modified host cell such as bacteria, yeast, Pichia, insect cells, and the like), where the genetically modified host cell is modified with a nucleic acid comprising a nucleotide sequence encoding the polypeptide. The IL-10 polypeptides may also be synthetically produced (e.g., by cell-free chemical synthesis).

Nucleic acid molecules encoding the IL-10 agents are contemplated by the present disclosure, including their naturally-occurring and non-naturally occurring isoforms, allelic variants and splice variants. The present disclosure also encompasses nucleic acid sequences that vary in one or more bases from a naturally-occurring DNA sequence but still translate into an amino acid sequence that corresponds to an IL-10 polypeptide due to degeneracy of the genetic code.

IL-10 Serum Concentration

The blood plasma levels of IL-10 in the methods described herein may be characterized in several manners, including: (1) a mean IL-10 serum trough concentration above some specified level or in a range of levels; (2) a mean IL-10 serum trough concentration above some specified level for some amount of time; (3) a steady state IL-10 serum concentration level above or below some specified level or in a range of levels; or (4) a $C_{max}$ of the concentration profile above or below some specified level or in some range of levels. As set forth herein, mean serum trough IL-10 concentrations have been found to be of particular import for efficacy in certain indications.

In some embodiments of the present disclosure, blood plasma level concentration profiles that may be produced include: a mean IL-10 serum trough concentration of greater than about 0.1 ng/mL, greater than about 0.15 ng/mL, greater than about 0.2 ng/mL, greater than about 0.25 ng/mL, greater than about 0.3 ng/mL, greater than about 0.35 ng/mL, greater than about 0.4 ng/mL, greater than about 0.45 ng/mL, greater than about 0.5 ng/mL, greater than about 0.55 ng/mL, greater than about 0.6 ng/mL, greater than about 0.65 ng/mL, greater than about 0.7 ng/mL, greater than about 0.75 ng/mL, greater than about 0.8 ng/mL, greater than about 0.85 ng/mL, greater than about 0.9 ng/mL, greater than about 0.95 ng/mL, greater than about 1.0 ng/mL, greater than about 1.1 ng/mL, greater than about 1.2 ng/mL, greater than about 1.3 ng/mL, greater than about 1.4 ng/mL, greater than about 1.5 ng/mL, greater than about 1.6 ng/mL, greater than about 1.7 ng/mL, greater than about 1.8 ng/mL, greater than about 1.9 ng/mL, greater than about 2.0 ng/mL, greater than about 2.1 ng/mL, greater than about 2.2 ng/mL, greater than about 2.3 ng/mL, greater than about 2.4 ng/mL, greater than about 2.5 ng/mL, greater than about 2.75 ng/mL, or greater than about 3.0 ng/mL.

In particular embodiments directed to the treatment or prevention of cancer-related-diseases, disorders or condition, therapy is optimized by achieving a mean IL-10 serum trough concentration of greater than about 0.5 ng/mL, greater than about 0.55 ng/mL, greater than about 0.6 ng/mL, greater than about 0.65 ng/mL, greater than about 0.7 ng/mL, greater than about 0.75 ng/mL, greater than about 0.8 ng/mL, greater than about 0.85 ng/mL, greater than about 0.9 ng/mL, greater than about 0.95 ng/mL, greater than about 1.0 ng/mL, greater than about 1.1 ng/mL, greater than about 1.2 ng/mL, greater than about 1.3 ng/mL, greater than about 1.4 ng/mL, greater than about 1.5 ng/mL, greater than about 1.6 ng/mL, greater than about 1.7 ng/mL, greater than about 1.8 ng/mL, greater than about 1.9 ng/mL, greater than about 2.0 ng/mL, greater than about 2.1 ng/mL, greater than about 2.2 ng/mL, greater than about 2.3 ng/mL, greater than about 2.4 ng/mL, greater than about 2.5 ng/mL, greater than about 2.75 ng/mL, or greater than about 3.0 ng/mL.

Particular embodiments of the present disclosure comprise a mean IL-10 serum trough concentration in a range of from about 0.1 ng/mL to about 1.0 ng/mL, from about 0.1 ng/mL to about 0.9 ng/mL, from about 0.1 ng/mL to about 0.8 ng/mL, from about 0.1 ng/mL to about 0.7 ng/mL, from about 0.1 ng/mL to about 0.6 ng/mL, from about of 0.1 ng/mL to about 0.5 ng/mL, from about 0.2 ng/mL to about 1.0 ng/mL, from about 0.2 ng/mL to about 0.9 ng/mL, from about 0.2 ng/mL to about 0.8 ng/mL, from about 0.2 ng/mL to about 0.7 ng/mL, from about 0.2 ng/mL to about 0.6 ng/mL, from about 0.2 ng/mL to about 0.5 ng/mL, from about 0.3 ng/mL to about 1.0 ng/mL, from about 0.3 ng/mL to about 0.9 ng/mL, from about 0.3 ng/mL to about 0.8 ng/mL, from about 0.3 ng/mL to about 0.7 ng/mL, from about 0.3 ng/mL to about 0.6 ng/mL, from about 0.3 ng/mL to about 0.5 ng/mL, from about 0.3 ng/mL to about 0.4 ng/mL, from about 0.4 ng/mL to about 1.0 ng/mL, from about 0.4 ng/mL to about 0.9 ng/mL, from about 0.4 ng/mL to about 0.8 ng/mL, from about 0.4 ng/mL to about 0.7 ng/mL, from about 0.4 ng/mL to about 0.6 ng/mL, from about 0.4 ng/mL to about 0.5 ng/mL, from about 0.5 ng/mL to about 1.0 ng/mL, from about 0.5 ng/mL to about 0.9 ng/mL, from about 0.5 ng/mL to about 0.8 ng/mL, from about 0.5 ng/mL to about 0.7 ng/mL, from about 0.5 ng/mL to about 0.6 ng/mL, from about 0.7 ng/mL to about 2.3 n/mL, from about 0.8 ng/mL to about 2.2 ng/mL, from about 0.9 ng/mL to about 2.1 ng/mL, from about 1.0 ng/mL to about 2.1 ng/mL, from about 1.0 ng/mL to about 2.0 ng/mL, from about 1.0 ng/mL to about 1.9 ng/mL, from about 1.0 ng/mL to about 1.8 ng/mL, from about 1.0 ng/mL to about 1.7 ng/mL, from about 1.0 ng/mL to about 1.6 ng/mL, from about 1.0 ng/mL to about 1.5 ng/mL, from about 1.9 ng/mL to greater than about 2.5 ng/mL, from about 1.9 ng/mL to about 2.5 ng/mL, from about 1.9 ng/mL to about 2.4 ng/mL, from about 1.9 ng/mL to about 2.3 ng/mL, from about 1.9 ng/mL to about 2.2 ng/mL, or from about 1.9 ng/mL to about 2.1 ng/mL.

In particular embodiments directed to the treatment or prevention of anti-inflammatory diseases, disorders or conditions, therapy is optimized by achieving a mean IL-10 serum trough concentration of 0.1 ng/mL to 1.0 ng/mL, of 0.1 ng/mL to 0.9 ng/mL, of 0.1 ng/mL to 0.8 ng/mL, of 0.1 ng/mL to 0.7 ng/mL, of 0.1 ng/mL to 0.6 ng/mL, of 0.1 ng/mL to 0.5 ng/mL, of 0.2 ng/mL to 1.0 ng/mL, of 0.2 ng/mL to 0.9 ng/mL, of 0.2 ng/mL to 0.8 ng/mL, of 0.2 ng/mL to 0.7 ng/mL, of 0.2 ng/mL to 0.6 ng/mL, of 0.2 ng/mL to 0.5 ng/mL, of 0.3 ng/mL to 1.0 ng/mL, of 0.3 ng/mL to 0.9 ng/mL, of 0.3 ng/mL to 0.8 ng/mL, of 0.3 ng/mL to 0.7 ng/mL, of 0.3 ng/mL to 0.6 ng/mL, of 0.3 ng/mL to 0.5 ng/mL, of 0.3 ng/mL to 0.4 ng/mL, of 0.4 ng/mL to 1.0 ng/mL, of 0.4 ng/mL to 0.9 ng/mL, of 0.4 ng/mL to 0.8 ng/mL, of 0.4 ng/mL to 0.7 ng/mL, of 0.4 ng/mL to 0.6 ng/mL, of 0.4 ng/mL to 0.5 ng/mL, of 0.5 ng/mL to 1.0 ng/mL, of 0.5 ng/mL to 0.9 ng/mL, of 0.5 ng/mL to 0.8 ng/mL, of 0.5 ng/mL to 0.7 ng/mL, or of 0.5 ng/mL to 0.6 ng/mL.

The Experimental section describes evaluations of the therapeutic efficacy of mIL-10 and PEG-mIL-10 in PDV6 squamous cell carcinoma and CT-26 colon carcinoma, wherein the mIL-10 and mPEG-IL-10 dosing parameters (amount and frequency of administration) are sufficient to achieve a mean IL-10 serum trough concentration of 1-2 ng/mL. As described in the Experimental section, PEG-IL-10 treatment resulted in a complete response, whereas IL-10 treatment demonstrated anti-tumor function but not a complete response.

The effect of IL-10 treatment in hepatitis C can also be evaluated. A mouse model with a functional immune system that is susceptible to infection by the hepatitis C virus (see Dorner, M. (9 Jun. 2011) Nature 474:208-211) can be utilized to evaluate the pharmacokinetic and pharmacodynamic effects of mIL-10 and PEG-mIL-10. Using the teachings set forth herein and the knowledge base of the skilled artisan, the effect of mIL-10 and PEG-mIL-10 administered to achieve a mean IL-10 serum trough concentration of about 0.1 ng/mL, about 0.5 ng/mL, about 1.0 ng/mL, about 1.5 ng/mL and about 2 ng/mL can be assessed.

Although not prevalent at therapeutic doses in most patient populations, administration of higher doses of IL-10 has caused adverse effects (e.g., headache, anemia and effects on the liver) in a limited number of subjects. Fortunately, such adverse effects are not prevalent when a mean IL-10 serum concentration of 0.1-2 ng/mL is maintained over the duration of treatment. Nonetheless, another embodiment of the present disclosure provides a method for monitoring a subject receiving IL-10 therapy to predict, and thus potentially avoid, adverse effects, the method comprising: (1) measuring the subject's peak concentration of IL-10; (2) measuring the subject's trough concentration of IL-10; (3) calculating a peak-trough fluctuation; and, (4) using the calculated peak-trough fluctuation to predict potential adverse effects in the subject. A smaller peak-trough fluctuation indicates a lower probability that the subject will experience IL-10-related adverse effects. In certain embodiments, particular peak-trough fluctuations are determined for the treatment of particular diseases, disorders and conditions using particular dosing parameters, and those fluctuations are used as reference standards.

In addition to the IL-10 dosing-related parameters described above, volume of distribution considerations are also pertinent. For the majority of drugs, plasma drug concentrations decline in a multi-exponential fashion. Immediately after intravenous administration, the drug rapidly distributes throughout an initial space (minimally defined as the plasma volume), and then a slower, equilibrative distribution to extravascular spaces (e.g., certain tissues) occurs. Intravenous IL-10 administration is associated with such a two-compartment kinetic model (see Rachmawati, H. et al. (2004) Pharm. Res. 21(11):2072-78). The pharmacokinetics of subcutaneous recombinant hIL-10 has also been studied (Radwanski, E. et al. (1998) Pharm. Res. 15(12):1895-1901). Moreover, IL-10 modifications have been introduced in an attempt to target the cytokine to specific cell types (see Rachmawati, H. (May 2007) Drug Met. Dist. 35(5):814-21).

As described further hereafter, the IL-10 and PEG-IL-10 anti-tumor efficacy observed in mice results from induction of cytotoxic enzymes in CD8+ T cells, resulting in the killing of tumor cells. Many anti-cancer compounds, including, but not limited to, apoptosis-inducing agents, are administrated in cycles. Frequently, a single dose or a series of doses approaching the Maximum Tolerated Dose (MTD) are administered, including a single application or series of high doses approaching the maximally tolerated dose (MTD), followed by a cessation of dosing (a "drug holiday") to allow recovery of the patient's normal physiology. By way of example, this dosing strategy is applied to cytotoxic chemotherapeutic antibody therapies, such as anti-VEGF (AVASTIN), and to short-lived biologic reagents, such as PROLEUKIN (IL-2).

Murine studies were performed to generate data helpful in understanding the pharmacokinetic parameters of IL-10 therapy and in optimizing the tumor treatment regimens in humans. As described in the Experimental section, although mice receiving the same amount of drug over the course of a week administered in either one or several doses had similar overall exposures, mice receiving daily doses exhibited the greatest reduction in tumor size (Table 15). Moreover, treatment regimens that resulted in maintenance of serum trough concentrations greater than about 1 ng/mL (e.g., 1.1-2.1 ng/mL) exhibited the greatest reduction in tumor size and weight (Table 16).

The present disclosure contemplates administration of any dose that results in maintenance of serum trough concentrations greater than about 0.1 ng/mL (e.g., 0.1-2 ng/mL, 0.1-1 ng/mL, 0.5-1.5 ng/mL or 1.1-2.1 ng/mL). For example, when the subject is a human, non-pegylated hIL-10 may be administered at a dose greater than 15 µg/kg/day, greater than 18 µg/kg/day, greater than 20 µg/kg/day, greater than 21 µg/kg/day, greater than 22 µg/kg/day, greater than 23 µg/kg/day, greater than 24 µg/kg/day, or greater than 25 µg/kg/day. When the subject is a human, PEG-hIL-10 comprising a relatively small PEG (e.g., 5 kDa mono-di PEG-hIL10) may be administered at a dose greater than 2.0 µg/kg/day, greater than 2.3 µg/kg/day, greater than 2.5 µg/kg/day, greater than 2.6 µg/kg/day, greater than 2.7 µg/kg/day, greater than 2.8 µg/kg/day, greater than 2.9 µg/kg/day, greater than 3.0 µg/kg/day, greater than 3.1 µg/kg/day, greater than 3.2 µg/kg/day, greater than 3.3 µg/kg/day, greater than 3.4 µg/kg/day or greater than 3.5 µg/kg/day.

The Role of CD8+ T Cells in IL-10 Function

CD8 (cluster of differentiation 8) is a transmembrane glycoprotein that serves as a co-receptor for the T cell receptor (TCR). The CD8 co-receptor is predominantly expressed on the surface of cytotoxic T lymphocytes (CTL), but it is also found on other cell types, including natural killer cells (NK). Like the TCR, CD8 binds to a major histocompatibility complex (MHC) molecule, but is specific for the Class I MHC protein.

CD8 function requires formation of a dimer comprising a pair of CD8 chains. There are two isoforms of CD8, alpha and beta, and the most common form of CD8 comprises a CD8-α and a CD8-β chain, both members of the immunoglobulin superfamily. CD8-α interacts with the Class I MHC molecule, and this interaction keeps the T cell receptor of the cytotoxic T cell and the target cell closely bound during antigen-specific activation. Cytotoxic T cells with CD8 surface protein are referred to as "CD8+ T cells". CD8+ T cells (CTL and NK cells) recognize antigens (generally cell-surface peptides or proteins resulting from infection by intracellular pathogens) of specific infected target cells, and if those antigens differ from the normal antigen profile of the subject ("immunologic self"), the CD8+ T cells become activated and induce apoptosis of the target cells.

Several scenarios exist wherein antigen profiles differ. For example, when a pathogen (e.g., a virus) invades a cell, the cell produces "non-self" cell surface antigens, and CD8+ T cells initiate an immunological response in an attempt to eradicate the infected cells. Another scenario occurs wherein some of a cell's proteins are modified due to mutations at the nucleic acid and/or the amino acid level. Cancer cells generally carry many mutations and are recognized as 'different' by CD8+ T cells. The presence of CD8+ T cells in human cancer correlates with longer survival.

In both of the aforementioned scenarios, activated CD8+ T cells produce IFNγ, perforin and Granzyme B. IFNγ is important to further up-regulate the "presentation" of antigens on the target cells, which occurs on Class I MHC protein. Perforin and Granzyme B mediate the killing of the target cell (e.g., virus and cancer).

Perforin, a cytolytic protein found in the granules of CTLs and NKs, inserts itself into a target cell's plasma membrane upon degranulation. Perforin has structural and functional similarities to complement component 9 (C9), and, like C9, perforin creates transmembrane tubules and is capable of non-specifically lysing a variety of target cells. Perforin is a key effector molecule for T-cell- and NK-cell-mediated cytolysis.

As alluded to above, Granzyme B is a serine protease expressed by cytotoxic T lymphocytes (CTL) and natural killer (NK) cells. CTL and NK cells recognize specific infected target cell populations and induce apoptosis of cells that bear on their surface 'non-self' antigens, usually peptides or proteins resulting from infection by intracellular pathogens. Granzyme B is crucial for the rapid induction of target cell apoptosis by CTL in cell-mediated immune response.

IL-10 plays diverse roles in the activation of CD8+ T cells. For example, IL-10 induces the effector molecules (IFNγ, perforin and Granzyme B) in memory CD8+ T cells, cells which have been generated during a previous infection or vaccination. Such memory CD8+ T cells are the cells responsible for providing a subject's long-term protection against viruses. Although generation and amplification of memory CD8+ T cells may occur when IL-10 is not present (Vicari, A. and Trinchieri, G. (2004) Immuno. Rev. 202: 223-236), the fact that IL-10 directly activates such cells provides a unique and alternative therapeutic approach. Though chronic viral infection has been linked to CD8+ T cells (Virgin, H. et al. (2009) Cell 138, p. 30), treatment of subjects (e.g., mice) with unpegylated IL-10 or pegylated IL-10 has not been described.

In view of the above, an embodiment of the present disclosure is based on the nexus between CD8+ T cells and both cancer and viral infections. Thus, certain methods of treating and/or preventing cancer-related diseases, disorders and conditions, such as maintaining a mean IL-10 serum concentration of, e.g., ≥0.5 ng/mL, ≥1 ng/mL, or ≥2 ng/mL, should also be applicable in the treatment of viral-related diseases, disorders and conditions.

In contrast to other cytokines, IL-10 can be deemed both a potent immunostimulatory and immunosuppressive factor. The role of CD8+ T cells in chronic inflammation has not been completely elucidated. However, because the involvement of IFNγ in cancer and viral-related disorders is mediated, at least in part, through CD8+ T cells, and because the IL-10-T cell pathway implicated in the control of inflammation-related disorders (through down-regulation of inflammatory cytokines) also involves IFNγ, CD8+ T cells may also play a key role in inflammation. Thus, IL-10 may prove to be an important therapeutic in the current stable of anti-inflammatory agents.

Methods of Production of IL-10

A polypeptide of the present disclosure can be produced by any suitable method, including non-recombinant (e.g., chemical synthesis) and recombinant methods.

A. Chemical Synthesis

Where a polypeptide is chemically synthesized, the synthesis may proceed via liquid-phase or solid-phase. Solid-phase peptide synthesis (SPPS) allows the incorporation of unnatural amino acids and/or peptide/protein backbone modification. Various forms of SPPS, such as 9-fluorenyl-methoxycarbonyl (Fmoc) and t-butyloxycarbonyl (Boc), are available for synthesizing polypeptides of the present disclosure. Details of the chemical syntheses are known in the art (e.g., Ganesan A. (2006) Mini Rev. Med. Chem. 6:3-10; and Camarero J. A. et al., (2005) Protein Pept Lett. 12:723-8).

Solid phase peptide synthesis may be performed as described hereafter. The alpha functions (Nα) and any reactive side chains are protected with acid-labile or base-labile groups. The protective groups are stable under the conditions for linking amide bonds but can readily be cleaved without impairing the peptide chain that has formed. Suitable protective groups for the α-amino function include, but are not limited to, the following: Boc, benzyloxycarbonyl (Z), O-chlorbenzyloxycarbonyl, bi-phenylisopropyloxycarbonyl, tert-amyloxycarbonyl (Amoc), α,α-dimethyl-3,5-dimethoxy-benzyloxycarbonyl, o-nitrosulfenyl, 2-cyano-t-butoxy-carbonyl, Fmoc, 1-(4,4-dimethyl-2,6-dioxocylohex-1-ylidene)ethyl (Dde) and the like.

Suitable side chain protective groups include, but are not limited to: acetyl, allyl (All), allyloxycarbonyl (Alloc), benzyl (Bzl), benzyloxycarbonyl (Z), t-butyloxycarbonyl (Boc), benzyloxymethyl (Bom), o-bromobenzyloxycarbonyl, t-butyl (tBu), t-butyldimethylsilyl, 2-chlorobenzyl, 2-chlorobenzyloxycarbonyl, 2,6-dichlorobenzyl, cyclohexyl, cyclopentyl, 1-(4,4-dimethyl-2,6-dioxocyclohex-1-ylidene)ethyl (Dde), isopropyl, 4-methoxy-2,3-6-trimethyl-benzylsulfonyl (Mtr), 2,3,5,7,8-pentamethylchroman-6-sulfonyl (Pmc), pivalyl, tetrahydropyran-2-yl, tosyl (Tos), 2,4,6-trimethoxybenzyl, trimethylsilyl and trityl (Trt).

In the solid phase synthesis, the C-terminal amino acid is coupled to a suitable support material. Suitable support materials are those which are inert towards the reagents and reaction conditions for the step-wise condensation and cleavage reactions of the synthesis process and which do not dissolve in the reaction media being used. Examples of commercially-available support materials include styrene/divinylbenzene copolymers which have been modified with reactive groups and/or polyethylene glycol; chloromethylated styrene/divinylbenzene copolymers; hydroxymethylated or aminomethylated styrene/divinylbenzene copolymers; and the like. When preparation of the peptidic acid is desired, polystyrene (1%)-divinylbenzene or TentaGel® derivatized with 4-benzyloxybenzyl-alcohol (Wang-anchor) or 2-chlorotrityl chloride can be used. In the case of the peptide amide, polystyrene (1%) divinylbenzene or Tenta-Gel® derivatized with 5-(4'-aminomethyl)-3',5'-dimethoxy-phenoxy)valeric acid (PAL-anchor) or p-(2,4-dimethoxyphenyl-amino methyl)-phenoxy group (Rink amide anchor) can be used.

The linkage to the polymeric support can be achieved by reacting the C-terminal Fmoc-protected amino acid with the support material by the addition of an activation reagent in ethanol, acetonitrile, N,N-dimethylformamide (DMF), dichloromethane, tetrahydrofuran, N-methylpyrrolidone or similar solvents at room temperature or elevated temperatures (e.g., between 40° C. and 60° C.) and with reaction times of, e.g., 2 to 72 hours.

The coupling of the Nα-protected amino acid (e.g., the Fmoc amino acid) to the PAL, Wang or Rink anchor can, for example, be carried out with the aid of coupling reagents such as N,N'-dicyclohexylcarbodiimide (DCC), N,N'-diisopropylcarbodiimide (DIC) or other carbodiimides, 2-(1H-benzotriazol-1-yl)-1,1,3,3-tetramethyluronium tetrafluoroborate (TBTU) or other uronium salts, O-acyl-ureas, benzotriazol-1-yl-tris-pyrrolidino-phosphonium hexafluorophosphate (PyBOP) or other phosphonium salts, N-hydroxy-succinimides, other N-hydroxyimides or oximes in the presence or absence of 1-hydroxybenzotriazole or 1-hydroxy-7-azabenzotriazole, e.g., with the aid of TBTU with addition of HOBt, with or without the addition of a base such as, for example, diisopropylethylamine (DIEA), triethylamine or N-methylmorpholine, e.g., diisopropylethylamine with reaction times of 2 to 72 hours (e.g., 3 hours in a 1.5 to 3-fold excess of the amino acid and the coupling reagents, for example, in a 2-fold excess and at temperatures between about 10° C. and 50° C., for example, 25° C., in a solvent such as dimethylformamide, N-methylpyrrolidone or dichloromethane, e.g., dimethylformamide).

Instead of the coupling reagents, it is also possible to use the active esters (e.g., pentafluorophenyl, p-nitrophenyl or the like), the symmetric anhydride of the Nα-Fmoc-amino acid, its acid chloride or acid fluoride, under the conditions described above.

The Nα-protected amino acid (e.g., the Fmoc amino acid) can be coupled to the 2-chlorotrityl resin in dichloromethane with the addition of DIEA and having reaction times of 10 to 120 minutes, e.g., 20 minutes, but is not limited to the use of this solvent and this base.

The successive coupling of the protected amino acids can be carried out according to conventional methods in peptide synthesis, typically in an automated peptide synthesizer. After cleavage of the Nα-Fmoc protective group of the coupled amino acid on the solid phase by treatment with, e.g., piperidine (10% to 50%) in dimethylformamide for 5 to 20 minutes, e.g., 2×2 minutes with 50% piperidine in DMF and 1×15 minutes with 20% piperidine in DMF, the next protected amino acid in a 3 to 10-fold excess, e.g., in a 10-fold excess, is coupled to the previous amino acid in an inert, non-aqueous, polar solvent such as dichloromethane, DMF or mixtures of the two and at temperatures between about 10° C. and 50° C., e.g., at 25° C. The previously mentioned reagents for coupling the first Nα-Fmoc amino acid to the PAL, Wang or Rink anchor are suitable as coupling reagents. Active esters of the protected amino acid, or chlorides or fluorides or symmetric anhydrides thereof can also be used as an alternative.

At the end of the solid phase synthesis, the peptide is cleaved from the support material while simultaneously cleaving the side chain protecting groups. Cleavage can be carried out with trifluoroacetic acid or other strongly acidic media with addition of 5%-20% V/V of scavengers such as dimethylsulfide, ethylmethylsulfide, thioanisole, thiocresol, m-cresol, anisole ethanedithiol, phenol or water, e.g., 15% v/v dimethylsulfide/ethanedithiol/m-cresol 1:1:1, within 0.5 to 3 hours, e.g., 2 hours. Peptides with fully protected side chains are obtained by cleaving the 2-chlorotrityl anchor with glacial acetic acid/trifluoroethanol/dichloromethane 2:2:6. The protected peptide can be purified by chromatography on silica gel. If the peptide is linked to the solid phase via the Wang anchor and if it is intended to obtain a peptide with a C-terminal alkylamidation, the cleavage can be carried out by aminolysis with an alkylamine or fluoroalkylamine. The aminolysis is carried out at temperatures between about −10° C. and 50° C. (e.g., about 25° C.), and reaction times between about 12 and 24 hours (e.g., about 18 hours). In addition, the peptide can be cleaved from the support by re-esterification, e.g., with methanol.

The acidic solution that is obtained may be admixed with a 3 to 20-fold amount of cold ether or n-hexane, e.g., a 10-fold excess of diethyl ether, in order to precipitate the peptide and hence to separate the scavengers and cleaved protective groups that remain in the ether. A further purification can be carried out by re-precipitating the peptide several times from glacial acetic acid. The precipitate that is obtained can be taken up in water or tert-butanol or mixtures of the two solvents, e.g., a 1:1 mixture of tert-butanol/water, and freeze-dried.

The peptide obtained can be purified by various chromatographic methods, including ion exchange over a weakly basic resin in the acetate form; hydrophobic adsorption chromatography on non-derivatized polystyrene/divinylbenzene copolymers (e.g., Amberlite® XAD); adsorption chromatography on silica gel; ion exchange chromatography, e.g., on carboxymethyl cellulose; distribution chromatography, e.g., on Sephadex® G-25; countercurrent distribution chromatography; or high pressure liquid chromatography (HPLC) e.g., reversed-phase HPLC on octyl or octadecylsilylsilica (ODS) phases.

B. Recombinant Production

Methods describing the preparation of human and mouse IL-10 can be found in, for example, U.S. Pat. No. 5,231,012, which teaches methods for the production of proteins having IL-10 activity, including recombinant and other synthetic techniques. IL-10 can be of viral origin, and the cloning and expression of a viral IL-10 from Epstein Barr virus (BCRF1 protein) is disclosed in Moore et al., (1990) Science 248: 1230. IL-10 can be obtained in a number of ways using standard techniques known in the art, such as those described herein. Recombinant human IL-10 is also commercially available, e.g., from PeproTech, Inc., Rocky Hill, N.J.

Where a polypeptide is produced using recombinant techniques, the polypeptide may be produced as an intracellular protein or as a secreted protein, using any suitable construct and any suitable host cell, which can be a prokaryotic or eukaryotic cell, such as a bacterial (e.g., E. coli) or a yeast host cell, respectively. Other examples of eukaryotic cells that may be used as host cells include insect cells, mammalian cells, and/or plant cells. Where mammalian host cells are used, they may include human cells (e.g., HeLa, 293, H9 and Jurkat cells); mouse cells (e.g., NIH3T3, L cells, and C127 cells); primate cells (e.g., Cos 1, Cos 7 and CV1); and hamster cells (e.g., Chinese hamster ovary (CHO) cells).

A variety of host-vector systems suitable for the expression of a polypeptide may be employed according to standard procedures known in the art. See, e.g., Sambrook et al., 1989 Current Protocols in Molecular Biology Cold Spring Harbor Press, New York; and Ausubel et al. 1995 Current Protocols in Molecular Biology, Eds. Wiley and Sons. Methods for introduction of genetic material into host cells include, for example, transformation, electroporation, conjugation, calcium phosphate methods and the like. The method for transfer can be selected so as to provide for stable expression of the introduced polypeptide-encoding nucleic acid. The polypeptide-encoding nucleic acid can be provided as an inheritable episomal element (e.g., a plasmid) or can be genomically integrated. A variety of appropriate vectors for use in production of a polypeptide of interest are commercially available.

Vectors can provide for extrachromosomal maintenance in a host cell or can provide for integration into the host cell genome. The expression vector provides transcriptional and translational regulatory sequences, and may provide for inducible or constitutive expression where the coding region is operably-linked under the transcriptional control of the transcriptional initiation region, and a transcriptional and translational termination region. In general, the transcriptional and translational regulatory sequences may include, but are not limited to, promoter sequences, ribosomal binding sites, transcriptional start and stop sequences, translational start and stop sequences, and enhancer or activator sequences. Promoters can be either constitutive or inducible, and can be a strong constitutive promoter (e.g., T7).

Expression constructs generally have convenient restriction sites located near the promoter sequence to provide for the insertion of nucleic acid sequences encoding proteins of interest. A selectable marker operative in the expression host may be present to facilitate selection of cells containing the vector. Moreover, the expression construct may include additional elements. For example, the expression vector may have one or two replication systems, thus allowing it to be maintained in organisms, for example, in mammalian or insect cells for expression and in a prokaryotic host for cloning and amplification. In addition, the expression construct may contain a selectable marker gene to allow the selection of transformed host cells. Selectable genes are well known in the art and will vary with the host cell used.

Isolation and purification of a protein can be accomplished according to methods known in the art. For example, a protein can be isolated from a lysate of cells genetically modified to express the protein constitutively and/or upon induction, or from a synthetic reaction mixture by immunoaffinity purification, which generally involves contacting the sample with an anti-protein antibody, washing to remove non-specifically bound material, and eluting the specifically bound protein. The isolated protein can be further purified by dialysis and other methods normally employed in protein purification. In one embodiment, the protein may be isolated using metal chelate chromatography methods. Proteins may contain modifications to facilitate isolation.

The polypeptides may be prepared in substantially pure or isolated form (e.g., free from other polypeptides). The polypeptides can be present in a composition that is enriched for the polypeptide relative to other components that may be present (e.g., other polypeptides or other host cell components). For example, purified polypeptide may be provided such that the polypeptide is present in a composition that is substantially free of other expressed proteins, e.g., less than about 90%, less than about 60%, less than about 50%, less than about 40%, less than about 30%, less than about 20%, less than about 10%, less than about 5%, or less than about 1%.

An IL-10 polypeptide may be generated using recombinant techniques to manipulate different IL-10-related nucleic acids known in the art to provide constructs capable of encoding the IL-10 polypeptide. It will be appreciated that, when provided a particular amino acid sequence, the ordinary skilled artisan will recognize a variety of different nucleic acid molecules encoding such amino acid sequence in view of her background and experience in, for example, molecular biology.

Amide Bond Substitutions

In some cases, IL-10 includes one or more linkages other than peptide bonds, e.g., at least two adjacent amino acids are joined via a linkage other than an amide bond. For example, in order to reduce or eliminate undesired proteolysis or other means of degradation, and/or to increase serum stability, and/or to restrict or increase conformational flexibility, one or more amide bonds within the backbone of IL-10 can be substituted.

In another example, one or more amide linkages (—CO—NH—) in IL-10 can be replaced with a linkage which is an isostere of an amide linkage, such as —CH$_2$NH—, —CH$_2$S—, —CH$_2$CH$_2$—, —CH=CH-(cis and trans), —COCH$_2$—, —CH(OH)CH$_2$— or —CH$_2$SO—. One or more amide linkages in IL-10 can also be replaced by, for example, a reduced isostere pseudopeptide bond. See Couder et al. (1993) Int. J. Peptide Protein Res. 41:181-184. Such replacements and how to effect them are known to those of ordinary skill in the art.

Amino Acid Substitutions

One or more amino acid substitutions can be made in an IL-10 polypeptide. The following are non-limiting examples:

a) substitution of alkyl-substituted hydrophobic amino acids, including alanine, leucine, isoleucine, valine, norleucine, (S)-2-aminobutyric acid, (S)-cyclohexylalanine or other simple alpha-amino acids substituted by an aliphatic side chain from C$_1$-C$_{10}$ carbons including branched, cyclic and straight chain alkyl, alkenyl or alkynyl substitutions;

b) substitution of aromatic-substituted hydrophobic amino acids, including phenylalanine, tryptophan, tyrosine, sulfotyrosine, biphenylalanine, 1-naphthylalanine, 2-naphthylalanine, 2-benzothienylalanine, 3-benzothienylalanine, histidine, including amino, alkylamino, dialkylamino, aza, halogenated (fluoro, chloro, bromo, or iodo) or alkoxy (from C$_1$-C$_4$)-substituted forms of the above-listed aromatic amino acids, illustrative examples of which are: 2-, 3- or 4-aminophenylalanine, 2-, 3- or 4-chlorophenylalanine, 2-, 3- or 4-methylphenylalanine, 2-, 3- or 4-methoxyphenylalanine, 5-amino-, 5-chloro-, 5-methyl- or 5-methoxytryptophan, 2'-, 3'-, or 4'-amino-, 2'-, 3'-, or 4'-chloro-, 2, 3, or 4-biphenylalanine, 2'-, 3'-, or 4'-methyl-, 2-, 3- or 4-biphenylalanine, and 2- or 3-pyridylalanine;

c) substitution of amino acids containing basic side chains, including arginine, lysine, histidine, ornithine, 2,3-diaminopropionic acid, homoarginine, including alkyl, alkenyl, or aryl-substituted (from C$_1$-C$_{10}$ branched, linear, or cyclic) derivatives of the previous amino acids, whether the substituent is on the heteroatoms (such as the alpha nitrogen, or the distal nitrogen or nitrogens, or on the alpha carbon, in the pro-R position for example. Compounds that serve as illustrative examples include: N-epsilon-isopropyl-lysine, 3-(4-tetrahydropyridyl)-glycine, 3-(4-tetrahydropyridyl)-alanine, N,N-gamma,gamma'-diethyl-homoarginine. Included also are compounds such as alpha-methyl-arginine, alpha-methyl-2,3-diaminopropionic acid, alpha-methyl-histidine, alpha-methyl-ornithine where the alkyl group occupies the pro-R position of the alpha-carbon. Also included are the amides formed from alkyl, aromatic, heteroaromatic (where the heteroaromatic group has one or more nitrogens, oxygens or sulfur atoms singly or in combination), carboxylic acids or any of the many well-known activated derivatives such as acid chlorides, active esters, active azolides and related derivatives, and lysine, ornithine, or 2,3-diaminopropionic acid;

d) substitution of acidic amino acids, including aspartic acid, glutamic acid, homoglutamic acid, tyrosine, alkyl, aryl, arylalkyl, and heteroaryl sulfonamides of 2,4-diaminopriopionic acid, ornithine or lysine and tetrazole-substituted alkyl amino acids;

e) substitution of side chain amide residues, including asparagine, glutamine, and alkyl or aromatic substituted derivatives of asparagine or glutamine; and f) substitution of hydroxyl-containing amino acids, including serine, threonine, homoserine, 2,3-diaminopropionic acid, and alkyl or aromatic substituted derivatives of serine or threonine.

In some cases, IL-10 comprises one or more naturally occurring non-genetically encoded L-amino acids, synthetic L-amino acids, or D-enantiomers of an amino acid. For example, IL-10 can comprise only D-amino acids. For example, an IL-10 polypeptide can comprise one or more of the following residues: hydroxyproline, β-alanine, o-aminobenzoic acid, m-aminobenzoic acid, p-aminobenzoic acid, m-aminomethylbenzoic acid, 2,3-diaminopropionic acid, α-aminoisobutyric acid, N-methylglycine (sarcosine), ornithine, citrulline, t-butylalanine, t-butylglycine, N-methylisoleucine, phenylglycine, cyclohexylalanine, norleucine, naphthylalanine, pyridylalanine 3-benzothienyl alanine, 4-chlorophenylalanine, 2-fluorophenylalanine, 3-fluorophenylalanine, 4-fluorophenylalanine, penicillamine, 1,2,3,4-tetrahydroisoquinoline-3-carboxylic acid, β-2-thienylalanine, methionine sulfoxide, homoarginine, N-acetyl lysine, 2,4-diamino butyric acid, rho-aminophenylalanine, N-methylvaline, homocysteine, homoserine, ε-amino hexanoic acid, ω-aminohexanoic acid, ω-aminoheptanoic acid, ω-aminooctanoic acid, ω-aminodecanoic acid, ω-aminotetradecanoic acid, cyclohexylalanine, α,γ-diaminobutyric acid, α,β-diaminopropionic acid, δ-amino valeric acid, and 2,3-diaminobutyric acid.

Additional Modifications

A cysteine residue or a cysteine analog can be introduced into an IL-10 polypeptide to provide for linkage to another peptide via a disulfide linkage or to provide for cyclization of the IL-10 polypeptide. Methods of introducing a cysteine or cysteine analog are known in the art; see, e.g., U.S. Pat. No. 8,067,532.

An IL-10 polypeptide can be cyclized. One or more cysteines or cysteine analogs can be introduced into an IL-10 polypeptide, where the introduced cysteine or cysteine analog can form a disulfide bond with a second introduced cysteine or cysteine analog. Other means of cyclization include introduction of an oxime linker or a lanthionine linker; see, e.g., U.S. Pat. No. 8,044,175. Any combination of amino acids (or non-amino acid moieties) that can form a cyclizing bond can be used and/or introduced. A cyclizing bond can be generated with any combination of amino acids (or with an amino acid and —(CH2)$_n$-CO— or —(CH2)$_n$-C$_6$H$_4$—CO—) with functional groups which allow for the introduction of a bridge. Some examples are disulfides, disulfide mimetics such as the —(CH2)$_n$- carba bridge, thioacetal, thioether bridges (cystathionine or lanthionine) and bridges containing esters and ethers. In these examples, n can be any integer, but is frequently less than ten.

Other modifications include, for example, an N-alkyl (or aryl) substitution (ψ[CONR]), or backbone crosslinking to construct lactams and other cyclic structures. Other derivatives include C-terminal hydroxymethyl derivatives, o-modified derivatives (e.g., C-terminal hydroxymethyl benzyl ether), N-terminally modified derivatives including substituted amides such as alkylamides and hydrazides.

In some cases, one or more L-amino acids in an IL-10 polypeptide is replaced with one or more D-amino acids.

In some cases, an IL-10 polypeptide is a retroinverso analog (see, e.g., Sela and Zisman (1997) FASEB J. 11:449). Retro-inverso peptide analogs are isomers of linear polypeptides in which the direction of the amino acid sequence is reversed (retro) and the chirality, D- or L-, of one or more amino acids therein is inverted (inverso), e.g., using D-amino acids rather than L-amino acids. [See, e.g., Jameson et al. (1994) Nature 368:744; and Brady et al. (1994) Nature 368:692].

An IL-10 polypeptide can include a "Protein Transduction Domain" (PTD), which refers to a polypeptide, polynucleotide, carbohydrate, or organic or inorganic molecule that facilitates traversing a lipid bilayer, micelle, cell membrane, organelle membrane, or vesicle membrane. A PTD attached to another molecule facilitates the molecule traversing a membrane, for example going from extracellular space to intracellular space, or cytosol to within an organelle. In some embodiments, a PTD is covalently linked to the amino terminus of an IL-10 polypeptide, while in other embodiments, a PTD is covalently linked to the carboxyl terminus of an IL-10 polypeptide. Exemplary protein transduction domains include, but are not limited to, a minimal undecapeptide protein transduction domain (corresponding to residues 47-57 of HIV-1 TAT comprising YGRKKRRQRRR; SEQ ID NO://); a polyarginine sequence comprising a number of arginine residues sufficient to direct entry into a cell (e.g., 3, 4, 5, 6, 7, 8, 9, 10, or 10-50 arginines); a VP22 domain (Zender et al. (2002) Cancer Gene Ther. 9(6):489-96); a Drosophila Antennapedia protein transduction domain (Noguchi et al. (2003) Diabetes 52(7):1732-1737); a truncated human calcitonin peptide (Trehin et al. (2004) Pharm. Research 21:1248-1256); polylysine (Wender et al. (2000) Proc. Natl. Acad. Sci. USA 97:13003-13008); RRQR-RTSKLMKR (SEQ ID NO:/); Transportan GWTLN-SAGYLLGKINLKALAALAKKIL (SEQ ID NO:/); KALAWEAKLAKALAKALAKHLAKALAKALKCEA (SEQ ID NO:/); and RQIKIWFQNRRMKWKK (SEQ ID NO:/). Exemplary PTDs include, but are not limited to, YGRKKRRQRRR (SEQ ID NO:/), RKKRRQRRR (SEQ ID NO:/); an arginine homopolymer of from 3 arginine residues to 50 arginine residues; exemplary PTD domain amino acid sequences include, but are not limited to, any of the following: YGRKKRRQRRR (SEQ ID NO://); RKKRRQRR (SEQ ID NO://); YARAAARQARA (SEQ ID NO://); THRLPRRRRRR (SEQ ID NO://); and GGRRAR-RRRRR (SEQ ID NO://).

The carboxyl group COR$_3$ of the amino acid at the C-terminal end of an IL-10 polypeptide can be present in a free form (R$_3$=OH) or in the form of a physiologically-tolerated alkaline or alkaline earth salt such as, e.g., a sodium, potassium or calcium salt. The carboxyl group can also be esterified with primary, secondary or tertiary alcohols such as, e.g., methanol, branched or unbranched C$_1$-C$_6$-alkyl alcohols, e.g., ethyl alcohol or tert-butanol. The carboxyl group can also be amidated with primary or secondary amines such as ammonia, branched or unbranched C$_1$-C$_6$-alkylamines or C$_1$-C$_6$ di-alkylamines, e.g., methylamine or dimethylamine.

The amino group of the amino acid NR$_1$R$_2$ at the N-terminus of an IL-10 polypeptide can be present in a free form (R$_1$=H and R$_2$=H) or in the form of a physiologically-tolerated salt such as, e.g., a chloride or acetate. The amino group can also be acetylated with acids such that R$_1$=H and R$_2$=acetyl, trifluoroacetyl, or adamantyl. The amino group can be present in a form protected by amino-protecting groups conventionally used in peptide chemistry, such as those provided above (e.g., Fmoc, Benzyloxy-carbonyl (Z), Boc, and Alloc). The amino group can be N-alkylated in which R$_1$ and/or R$_2$=C$_1$-C$_6$ alkyl or C$_2$-C$_8$ alkenyl or C$_7$-C$_9$ aralkyl. Alkyl residues can be straight-chained, branched or cyclic (e.g., ethyl, isopropyl and cyclohexyl, respectively).

Particular Modifications to Enhance and/or Mimic IL-10 Function

It is frequently beneficial, and sometimes imperative, to improve one of more physical properties of the treatment modalities disclosed herein (e.g., IL-10) and/or the manner in which they are administered. Improvements of physical properties include, for example, modulating immunogenicity; methods of increasing water solubility, bioavailability, serum half-life, and/or therapeutic half-life; and/or modulating biological activity. Certain modifications may also be useful to, for example, raise of antibodies for use in detection assays (e.g., epitope tags) and to provide for ease of protein purification. Such improvements must generally be imparted without adversely impacting the bioactivity of the treatment modality and/or increasing its immunogenicity.

Pegylation of IL-10 is one particular modification contemplated by the present disclosure, while other modifications include, but are not limited to, glycosylation (N- and O-linked); polysialylation; albumin fusion molecules comprising serum albumin (e.g., human serum albumin (HSA), cyno serum albumin, or bovine serum albumin (BSA)); albumin binding through, for example a conjugated fatty acid chain (acylation); and Fc-fusion proteins.

Pegylation:

The clinical effectiveness of protein therapeutics is often limited by short plasma half-life and susceptibility to protease degradation. Studies of various therapeutic proteins (e.g., filgrastim) have shown that such difficulties may be overcome by various modifications, including conjugating or linking the polypeptide sequence to any of a variety of nonproteinaceous polymers, e.g., polyethylene glycol (PEG), polypropylene glycol, or polyoxyalkylenes. This is frequently effected by a linking moiety covalently bound to both the protein and the nonproteinaceous polymer, e.g., a PEG. Such PEG-conjugated biomolecules have been shown to possess clinically useful properties, including better physical and thermal stability, protection against susceptibility to enzymatic degradation, increased solubility, longer in vivo circulating half-life and decreased clearance, reduced immunogenicity and antigenicity, and reduced toxicity.

In addition to the beneficial effects of pegylation on pharmacokinetic parameters, pegylation itself may enhance activity. For example, PEG-IL-10 has been shown to be more efficacious against certain cancers than unpegylated IL-10 (see, e.g., EP 206636A2).

PEGs suitable for conjugation to a polypeptide sequence are generally soluble in water at room temperature, and have the general formula R(O—CH$_2$—CH$_2$)$_n$O—R, where R is hydrogen or a protective group such as an alkyl or an alkanol group, and where n is an integer from 1 to 1000. When R is a protective group, it generally has from 1 to 8 carbons. The PEG conjugated to the polypeptide sequence can be linear or branched. Branched PEG derivatives, "star-PEGs" and multi-armed PEGs are contemplated by the present disclosure. A molecular weight of the PEG used in the present disclosure is not restricted to any particular range, and examples are set forth elsewhere herein; by way of example, certain embodiments have molecular weights between 5 kDa and 20 kDa, while other embodiments have molecular weights between 4 kDa and 10 kDa.

The present disclosure also contemplates compositions of conjugates wherein the PEGs have different n values, and thus the various different PEGs are present in specific ratios. For example, some compositions comprise a mixture of conjugates where n=1, 2, 3 and 4. In some compositions, the percentage of conjugates where n=1 is 18-25%, the percentage of conjugates where n=2 is 50-66%, the percentage of conjugates where n=3 is 12-16%, and the percentage of conjugates where n=4 is up to 5%. Such compositions can be produced by reaction conditions and purification methods know in the art. Exemplary reaction conditions are described throughout the specification. Cation exchange chromatography may be used to separate conjugates, and a fraction is then identified which contains the conjugate having, for example, the desired number of PEGs attached, purified free from unmodified protein sequences and from conjugates having other numbers of PEGs attached.

Pegylation most frequently occurs at the alpha amino group at the N-terminus of the polypeptide, the epsilon amino group on the side chain of lysine residues, and the imidazole group on the side chain of histidine residues. Since most recombinant polypeptides possess a single alpha and a number of epsilon amino and imidazole groups, numerous positional isomers can be generated depending on the linker chemistry. General pegylation strategies known in the art can be applied herein. PEG may be bound to a polypeptide of the present disclosure via a terminal reactive group (a "spacer") which mediates a bond between the free amino or carboxyl groups of one or more of the polypeptide sequences and polyethylene glycol. The PEG having the spacer which may be bound to the free amino group includes N-hydroxysuccinylimide polyethylene glycol which may be prepared by activating succinic acid ester of polyethylene glycol with N-hydroxysuccinylimide. Another activated polyethylene glycol which may be bound to a free amino group is 2,4-bis(O-methoxypolyethyleneglycol)-6-chloro-s-triazine, which may be prepared by reacting polyethylene glycol monomethyl ether with cyanuric chloride. The activated polyethylene glycol which is bound to the free carboxyl group includes polyoxyethylenediamine.

Conjugation of one or more of the polypeptide sequences of the present disclosure to PEG having a spacer may be carried out by various conventional methods. For example, the conjugation reaction can be carried out in solution at a pH of from 5 to 10, at temperature from 4° C. to room temperature, for 30 minutes to 20 hours, utilizing a molar ratio of reagent to protein of from 4:1 to 30:1. Reaction conditions may be selected to direct the reaction towards producing predominantly a desired degree of substitution. In general, low temperature, low pH (e.g., pH=5), and short reaction time tend to decrease the number of PEGs attached, whereas high temperature, neutral to high pH (e.g., pH≥7), and longer reaction time tend to increase the number of PEGs attached. Various means known in the art may be used to terminate the reaction. In some embodiments the reaction is terminated by acidifying the reaction mixture and freezing at, e.g., −20° C. Pegylation of various molecules is discussed in, for example, U.S. Pat. Nos. 5,252,714; 5,643,575; 5,919,455; 5,932,462; and 5,985,263. PEG-IL-10 is described in, e.g., U.S. Pat. No. 7,052,686. Specific reaction conditions contemplated for use herein are set forth in the Experimental section.

The present disclosure also contemplates the use of PEG mimetics. Recombinant PEG mimetics have been developed that retain the attributes of PEG (e.g., enhanced serum half-life) while conferring several additional advantageous properties. By way of example, simple polypeptide chains (comprising, for example, Ala, Glu, Gly, Pro, Ser and Thr) capable of forming an extended conformation similar to PEG can be produced recombinantly already fused to the peptide or protein drug of interest (e.g., Amunix' XTEN technology; Mountain View, Calif.). This obviates the need for an additional conjugation step during the manufacturing process. Moreover, established molecular biology techniques enable control of the side chain composition of the polypeptide chains, allowing optimization of immunogenicity and manufacturing properties.

Glycosylation:

For purposes of the present disclosure, "glycosylation" is meant to broadly refer to the enzymatic process that attaches glycans to proteins, lipids or other organic molecules. The use of the term "glycosylation" in conjunction with the present disclosure is generally intended to mean adding or deleting one or more carbohydrate moieties (either by removing the underlying glycosylation site or by deleting the glycosylation by chemical and/or enzymatic means), and/or adding one or more glycosylation sites that may or may not be present in the native sequence. In addition, the phrase includes qualitative changes in the glycosylation of the native proteins involving a change in the nature and proportions of the various carbohydrate moieties present.

Glycosylation can dramatically affect the physical properties (e.g., solubility) of polypeptides such as IL-10 and can also be important in protein stability, secretion, and subcellular localization. Glycosylated polypeptides may also exhibit enhanced stability or may improve one or more pharmacokinetic properties, such as half-life. In addition, solubility improvements can, for example, enable the generation of formulations more suitable for pharmaceutical administration than formulations comprising the non-glycosylated polypeptide.

Proper glycosylation can be essential for biological activity. In fact, some genes from eukaryotic organisms, when expressed in bacteria (e.g., *E. coli*) which lack cellular processes for glycosylating proteins, yield proteins that are recovered with little or no activity by virtue of their lack of glycosylation.

Addition of glycosylation sites can be accomplished by altering the amino acid sequence. The alteration to the polypeptide may be made, for example, by the addition of, or substitution by, one or more serine or threonine residues (for O-linked glycosylation sites) or asparagine residues (for N-linked glycosylation sites). The structures of N-linked and O-linked oligosaccharides and the sugar residues found in each type may be different. One type of sugar that is commonly found on both is N-acetylneuraminic acid (hereafter referred to as sialic acid). Sialic acid is usually the terminal residue of both N-linked and O-linked oligosaccharides and, by virtue of its negative charge, may confer acidic properties to the glycoprotein. A particular embodiment of the present disclosure comprises the generation and use of N-glycosylation variants.

The polypeptide sequences of the present disclosure may optionally be altered through changes at the nucleic acid level, particularly by mutating the nucleic acid encoding the polypeptide at preselected bases such that codons are generated that will translate into the desired amino acids. Another means of increasing the number of carbohydrate moieties on the polypeptide is by chemical or enzymatic coupling of glycosides to the polypeptide. Removal of carbohydrates may be accomplished chemically or enzymatically, or by substitution of codons encoding amino acid residues that are glycosylated. Chemical deglycosylation techniques are known, and enzymatic cleavage of carbohydrate moieties on polypeptides can be achieved by the use of a variety of endo- and exo-glycosidases.

Dihydrofolate reductase (DHFR)—deficient Chinese Hamster Ovary (CHO) cells are a commonly used host cell for the production of recombinant glycoproteins. These cells do not express the enzyme beta-galactoside alpha-2,6-sialyltransferase and therefore do not add sialic acid in the alpha-2,6 linkage to N-linked oligosaccharides of glycoproteins produced in these cells.

Polysialylation:

The present disclosure also contemplates the use of polysialylation, the conjugation of polypeptides to the naturally occurring, biodegradable α-(2→8) linked polysialic acid ("PSA") in order to improve the polypeptides' stability and in vivo pharmacokinetics. PSA is a biodegradable, non-toxic natural polymer that is highly hydrophilic, giving it a high apparent molecular weight in the blood which increases its serum half-life. In addition, polysialylation of a range of peptide and protein therapeutics has led to markedly reduced proteolysis, retention of in vivo activity, and reduction in immunogenicity and antigenicity (see, e.g., G. Gregoriadis et al., Int. J. Pharmaceutics 300(1-2):125-30). As with modifications with other conjugates (e.g., PEG), various techniques for site-specific polysialylation are available (see, e.g., T. Lindhout et al., (2011) PNAS 108(18)7397-7402).

Albumin Fusion:

Additional suitable components and molecules for conjugation include albumins such as human serum albumin (HSA), cyno serum albumin, and bovine serum albumin (BSA).

Mature HSA, a 585 amino acid polypeptide (~67 kDa) having a serum half-life of ~20 days, is primarily responsible for the maintenance of colloidal osmotic blood pressure, blood pH, and transport and distribution of numerous endogenous and exogenous ligands. The protein has three structurally homologous domains (domains I, II and III), is almost entirely in the alpha-helical conformation, and is highly stabilized by 17 disulphide bridges. The three primary drug binding regions of albumin are located on each of the three domains within sub-domains IB, IIA and IIIA.

Albumin synthesis takes place in the liver, which produces the short-lived, primary product preproalbumin. Thus, the full-length HSA has a signal peptide of 18 amino acids (MKWVTFISLLFLFSSAYS; SEQ ID NO://) followed by a pro-domain of 6 amino acids (RGVFRR; SEQ ID NO://); this 24 amino acid residue peptide may be referred to as the pre-pro domain. HSA can be expressed and secreted using its endogenous signal peptide as a pre-pro-domain. Alternatively, HSA can be expressed and secreted using a IgK signal peptide fused to a mature construct. Preproalbumin is rapidly co-translationally cleaved in the endoplasmic reticulum lumen at its amino terminus to produce the stable, 609-amino acid precursor polypeptide, proalbumin. Proalbumin then passes to the Golgi apparatus, where it is converted to the 585 amino acid mature albumin by a furin-dependent amino-terminal cleavage.

The primary amino acid sequences, structure, and function of albumins are highly conserved across species, as are the processes of albumin synthesis and secretion. Albumin serum proteins comparable to HSA are found in, for example, cynomolgus monkeys, cows, dogs, rabbits and rats. Of the non-human species, bovine serum albumin (BSA) is the most structurally similar to HSA (see, e.g., Kosa et al., November 2007 J Pharm Sci. 96(11):3117-24). The present disclosure contemplates the use of albumin from non-human species, including, but not limited to, those set forth above, in, for example, the drug development process.

According to the present disclosure, albumin may be conjugated to a drug molecule (e.g., a polypeptide described herein) at the carboxyl terminus, the amino terminus, both the carboxyl and amino termini, and internally (see, e.g., U.S. Pat. No. 5,876,969 and U.S. Pat. No. 7,056,701).

In the HSA-drug molecule conjugates contemplated by the present disclosure, various forms of albumin may be used, such as albumin secretion pre-sequences and variants thereof, fragments and variants thereof, and HSA variants. Such forms generally possess one or more desired albumin activities. In additional embodiments, the present disclosure involves fusion proteins comprising a polypeptide drug molecule fused directly or indirectly to albumin, an albumin fragment, and albumin variant, etc., wherein the fusion protein has a higher plasma stability than the unfused drug molecule and/or the fusion protein retains the therapeutic activity of the unfused drug molecule. In some embodiments, the indirect fusion is effected by a linker, such as a peptide linker or modified version thereof.

Intracellular cleavage may be carried out enzymatically by, for example, furin or caspase. Cells express a low level of these endogenous enzymes, which are capable of cleaving a portion of the fusion molecules intracellularly; thus, some of the polypeptides are secreted from the cell without being conjugated to HSA, while some of the polypeptides are secreted in the form of fusion molecules that comprise HSA. Embodiments of the present disclosure contemplate the use of various furin fusion constructs. For example, constructs may be designed that comprise the sequence RGRR, RKRKKR, RKKR, or RRRKKR.

The present disclosure also contemplates extra-cellular cleavage (i.e., ex-vivo cleavage) whereby the fusion molecules are secreted from the cell, subjected to purification, and then cleaved. It is understood that the excision may dissociate the entire HSA-linker complex from the mature IL-10, or less that the entire HSA-linker complex.

As alluded to above, fusion of albumin to one or more polypeptides of the present disclosure can, for example, be achieved by genetic manipulation, such that the nucleic acid coding for HSA, or a fragment thereof, is joined to the nucleic acid coding for the one or more polypeptide sequences. Thereafter, a suitable host can be transformed or transfected with the fused nucleotide sequences in the form of, for example, a suitable plasmid, so as to express a fusion polypeptide. The expression may be effected in vitro from, for example, prokaryotic or eukaryotic cells, or in vivo from, for example, a transgenic organism. In some embodiments of the present disclosure, the expression of the fusion protein is performed in mammalian cell lines, for example, CHO cell lines. Transformation is used broadly herein to refer to the genetic alteration of a cell resulting from the direct uptake through the cell membrane, incorporation and expression of exogenous genetic material (exogenous nucleic acid). Transformation occurs naturally in some species of bacteria, but it can also be effected by artificial means in other cells.

Furthermore, albumin itself may be modified to extend its circulating half-life. Fusion of the modified albumin to IL-10 can be attained by the genetic manipulation techniques described above or by chemical conjugation; the resulting fusion molecule has a half-life that exceeds that of fusions with non-modified albumin (see WO2011/051489).

Alternative Albumin Binding Strategies:

Several albumin-binding strategies have been developed as alternatives to direct fusion, including albumin binding through a conjugated fatty acid chain (acylation). Because serum albumin is a transport protein for fatty acids, these natural ligands with albumin-binding activity have been used for half-life extension of small protein therapeutics. For example, insulin determir (LEVEMIR), an approved product for diabetes, comprises a myristyl chain conjugated to a genetically-modified insulin, resulting in a long-acting insulin analog.

The present disclosure also contemplates fusion proteins which comprise an albumin binding domain (ABD) polypeptide sequence and the sequence of one or more of the polypeptides described herein. Any ABD polypeptide sequence described in the literature can be a component of the fusion proteins. The components of the fusion proteins can be optionally covalently bonded through a linker, such as those linkers described herein. In some of the embodiments of the present disclosure, the fusion proteins comprise the ABD polypeptide sequence as an N-terminal moiety and the polypeptides described herein as a C-terminal moiety.

The present disclosure also contemplates fusion proteins comprising a fragment of an albumin binding polypeptide, which fragment substantially retains albumin binding; or a multimer of albumin binding polypeptides or their fragments comprising at least two albumin binding polypeptides or their fragments as monomer units. For a general discussion of ABD and related technologies, see WO 2012/050923, WO 2012/050930, WO 2012/004384 and WO 2009/016043.

Conjugation with Other Molecules:

Additional suitable components and molecules for conjugation include, for example, thyroglobulin; tetanus toxoid; Diphtheria toxoid; polyamino acids such as poly(D-lysine: D-glutamic acid); VP6 polypeptides of rotaviruses; influenza virus hemaglutinin, influenza virus nucleoprotein; Keyhole Limpet Hemocyanin (KLH); and hepatitis B virus core protein and surface antigen; or any combination of the foregoing.

Thus, the present disclosure contemplates conjugation of one or more additional components or molecules at the N- and/or C-terminus of a polypeptide sequence, such as another polypeptide (e.g., a polypeptide having an amino acid sequence heterologous to the subject polypeptide), or a carrier molecule. Thus, an exemplary polypeptide sequence can be provided as a conjugate with another component or molecule.

A conjugate modification may result in a polypeptide sequence that retains activity with an additional or complementary function or activity derived from the second molecule. For example, a polypeptide sequence may be conjugated to a molecule, e.g., to facilitate solubility, storage, in vivo or shelf half-life or stability, reduction in immunogenicity, delayed or controlled release in vivo, etc. Other functions or activities include a conjugate that reduces toxicity relative to an unconjugated polypeptide sequence, a conjugate that targets a type of cell or organ more efficiently than an unconjugated polypeptide sequence, or a drug to further counter the causes or effects associated with a disease, disorder or condition as set forth herein (e.g., cancer).

An IL-10 polypeptide may also be conjugated to large, slowly metabolized macromolecules such as proteins; polysaccharides, such as sepharose, agarose, cellulose, or cellulose beads; polymeric amino acids such as polyglutamic acid, or polylysine; amino acid copolymers; inactivated virus particles; inactivated bacterial toxins such as toxoid from diphtheria, tetanus, cholera, or leukotoxin molecules; inactivated bacteria; and dendritic cells. Such conjugated forms, if desired, can be used to produce antibodies against a polypeptide of the present disclosure.

Additional candidate components and molecules for conjugation include those suitable for isolation or purification. Particular non-limiting examples include binding molecules, such as biotin (biotin-avidin specific binding pair), an antibody, a receptor, a ligand, a lectin, or molecules that comprise a solid support, including, for example, plastic or polystyrene beads, plates or beads, magnetic beads, test strips, and membranes.

Purification methods such as cation exchange chromatography may be used to separate conjugates by charge difference, which effectively separates conjugates into their various molecular weights. For example, the cation exchange column can be loaded and then washed with ~20 mM sodium acetate, pH ~4, and then eluted with a linear (0 M to 0.5 M) NaCl gradient buffered at a pH from about 3 to 5.5, e.g., at pH ~4.5. The content of the fractions obtained by cation exchange chromatography may be identified by molecular weight using conventional methods, for example, mass spectroscopy, SDS-PAGE, or other known methods for separating molecular entities by molecular weight.

Fc-Fusion Molecules:

In certain embodiments, the amino- or carboxyl-terminus of a polypeptide sequence of the present disclosure can be fused with an immunoglobulin Fc region (e.g., human Fc) to form a fusion conjugate (or fusion molecule). Fc fusion conjugates have been shown to increase the systemic half-life of biopharmaceuticals, and thus the biopharmaceutical product may require less frequent administration. Fc binds to the neonatal Fc receptor (FcRn) in endothelial cells that line the blood vessels, and, upon binding, the Fc fusion molecule is protected from degradation and re-released into the circulation, keeping the molecule in circulation longer. This Fc binding is believed to be the mechanism by which endogenous IgG retains its long plasma half-life. More recent Fc-fusion technology links a single copy of a biopharmaceutical to the Fc region of an antibody to optimize the pharmacokinetic and pharmacodynamic properties of the biopharmaceutical as compared to traditional Fc-fusion conjugates. Examples of other Fc-related technologies suitable for use with the polypeptides disclosed herein are described in WO 2013/113008.

Other Modifications:

The present disclosure contemplates the use of other modifications, currently known or developed in the future, of IL-10 to improve one or more properties. One such method for prolonging the circulation half-life, increasing the stability, reducing the clearance, or altering the immunogenicity or allergenicity of a polypeptide of the present disclosure involves modification of the polypeptide sequences by hesylation, which utilizes hydroxyethyl starch derivatives linked to other molecules in order to modify the polypeptide sequences' characteristics. Various aspects of hesylation are described in, for example, U.S. Patent Appln. Nos. 2007/0134197 and 2006/0258607.

The present disclosure also contemplates fusion molecules comprising SUMO as a fusion tag (LifeSensors, Inc.; Malvern, Pa.). Fusion of a polypeptide described herein to SUMO may convey several beneficial effects, including enhancement of expression, improvement in solubility, and/or assistance in the development of purification methods. SUMO proteases recognize the tertiary structure of SUMO and cleave the fusion protein at the C-terminus of SUMO, thus releasing a polypeptide described herein with the desired N-terminal amino acid.

Linkers:

Linkers and their use have been described above. Any of the foregoing components and molecules used to modify the polypeptide sequences of the present disclosure may optionally be conjugated via a linker. Suitable linkers include "flexible linkers" which are generally of sufficient length to permit some movement between the modified polypeptide sequences and the linked components and molecules. The linker molecules are generally about 6-50 atoms long. The linker molecules may also be, for example, aryl acetylene, ethylene glycol oligomers containing 2-10 monomer units, diamines, diacids, amino acids, or combinations thereof. Suitable linkers can be readily selected and can be of any suitable length, such as 1 amino acid (e.g., Gly), 2, 3, 4, 5, 6, 7, 8, 9, 10, 10-20, 20-30, 30-50 or more than 50 amino acids.

Exemplary flexible linkers include glycine polymers $(G)_n$, glycine-serine polymers (for example, $(GS)_n$, $GSGGS_n$, $GGGS_n$, $(G_mS_o)_n$, $(G_mS_oG_m)_n$, $(G_mS_oG_mS_oG_m)_n$, $(GSGGS_m)_n$, $(GSGS_mG)_n$ and $(GGGS_m)_n$, and combinations thereof, where m, and o are each independently selected from an integer of at least one), glycine-alanine polymers, alanine-serine polymers, and other flexible linkers. Glycine and glycine-serine polymers are relatively unstructured, and therefore may serve as a neutral tether between components. Exemplary flexible linkers include, but are not limited to GGSG, GGSGG, GSGSG, GSGGG, GGGSG, and GSSSG.

Therapeutic and Prophylactic Uses

The present disclosure contemplates the use of the IL-10 polypeptides described herein (e.g., PEG-IL-10) in the treatment or prevention of a broad range of diseases, disorders and/or conditions, and/or the symptoms thereof. Indeed, the teachings of the present disclosure are meant to apply to any disease, disorder or condition for which achieving or maintaining the above-described IL-10 mean serum trough concentration parameters may be beneficial. While particular uses are described in detail hereafter, it is to be understood that the present disclosure is not so limited. Furthermore, although general categories of particular diseases, disorders and conditions are set forth hereafter, some of the diseases, disorders and conditions may be a member of more than one category (e.g., cancer- and fibrotic-related disorders), and others may not be a member of any of the disclosed categories.

Fibrotic Disorders and Cancer.

In accordance with the present disclosure, IL-10 (e.g., PEG-IL-10) can be used to treat or prevent a proliferative condition or disorder, including a cancer (e.g., cancer of the uterus, cervix, breast, prostate, testes, gastrointestinal tract (e.g., esophagus, oropharynx, stomach, small or large intestines, colon, or rectum), kidney, renal cell, bladder, bone, bone marrow, skin, head or neck, skin, liver, gall bladder, heart, lung, pancreas, salivary gland, adrenal gland, thyroid, brain (e.g., gliomas), ganglia, central nervous system (CNS) and peripheral nervous system (PNS), and cancers of the hematopoietic system and the immune system (e.g., spleen or thymus). The present disclosure also provides methods of treating or preventing other cancer-related diseases, disorders or conditions, including, for example, immunogenic tumors, non-immunogenic tumors, dormant tumors, virus-induced cancers (e.g., epithelial cell cancers, endothelial cell cancers, squamous cell carcinomas and papillomavirus), adenocarcinomas, lymphomas, carcinomas, melanomas, leukemias, myelomas, sarcomas, teratocarcinomas, chemically-induced cancers, metastasis, and angiogenesis. The disclosure contemplates reducing tolerance to a tumor cell or cancer cell antigen, e.g., by modulating activity of a regulatory T cell and/or a CD8+ T cell (see, e.g., Ramirez-Montagut, et al. (2003) Oncogene 22:3180-3187; and Sawaya, et al. (2003) New Engl. J. Med. 349:1501-1509). In particular embodiments, the tumor or cancer is colon cancer, ovarian cancer, breast cancer, melanoma, lung cancer, glioblastoma, or leukemia. The use of the term(s) cancer-related diseases, disorders and conditions is meant to refer broadly to conditions that are associated, directly or indirectly, with cancer, and includes, e.g., angiogenesis and precancerous conditions such as dysplasia.

In some embodiments, the present disclosure provides methods for treating a proliferative condition, cancer, tumor, or precancerous condition with an IL-10 polypeptide (e.g., PEG-IL-10) and at least one additional therapeutic or diagnostic agent, examples of which are set forth elsewhere herein.

The present disclosure also provides methods of treating or preventing fibrotic diseases, disorders and conditions. As used herein, the phrase "fibrotic diseases, disorders and conditions", and similar terms (e.g., "fibrotic disorders") and phrases, is to be construed broadly such that it includes any condition which may result in the formation of fibrotic tissue or scar tissue (e.g., fibrosis in one or more tissues). By way of example, injuries (e.g., wounds) that may give rise to scar tissue include wounds to the skin, eye, lung, kidney, liver, central nervous system, and cardiovascular system. The phrase also encompasses scar tissue formation resulting from stroke, and tissue adhesion, for example, as a result of injury or surgery.

As used herein the term "fibrosis" refers to the formation of fibrous tissue as a reparative or reactive process, rather than as a normal constituent of an organ or tissue. Fibrosis is characterized by fibroblast accumulation and collagen deposition in excess of normal deposition in any particular tissue.

Fibrotic disorders include, but are not limited to, fibrosis arising from wound healing, systemic and local scleroderma, atherosclerosis, restenosis, pulmonary inflammation and fibrosis, idiopathic pulmonary fibrosis, interstitial lung disease, liver cirrhosis, fibrosis as a result of chronic hepatitis B or C infection, kidney disease (e.g., glomerulonephritis), heart disease resulting from scar tissue, keloids and hypertrophic scars, and eye diseases such as macular degeneration, and retinal and vitreal retinopathy. Additional fibrotic diseases include chemotherapeutic drug-induced fibrosis, radiation-induced fibrosis, and injuries and burns.

Fibrotic disorders are often hepatic-related, and there is frequently a nexus between such disorders and the inappropriate accumulation of liver cholesterol and triglycerides within the hepatocytes. This accumulation appears to result in a pro-inflammatory response that leads to liver fibrosis and cirrhosis. Hepatic disorders having a fibrotic component include non-alcoholic fatty liver disease (NAFLD) and non-alcoholic steatohepatitis (NASH).

Cardiovascular Diseases.

The present disclosure also contemplates the use of the IL-10 polypeptides (e.g., PEG-IL-10) described herein to treat and/or prevent certain cardiovascular- and/or associated metabolic-related diseases, disorders and conditions, as well as disorders associated therewith.

As used herein, the terms "cardiovascular disease", "heart disease" and the like refer to any disease that affects the cardiovascular system, primarily cardiac disease, vascular diseases of the brain and kidney, and peripheral arterial diseases. Cardiovascular disease is a constellation of diseases that includes coronary heart disease (i.e., ischemic heart disease or coronary artery disease), atherosclerosis, cardiomyopathy, hypertension, hypertensive heart disease, cor pulmonale, cardiac dysrhythmias, endocarditis, cerebrovascular disease, and peripheral arterial disease. Cardiovascular disease is the leading cause of deaths worldwide, and while it usually affects older adults, the antecedents of cardiovascular disease, notably atherosclerosis, begin in early life.

Particular embodiments of the present disclosure are directed to the use of IL-10 polypeptides to treat and/or prevent atherosclerosis, a chronic condition in which an artery wall thickens to form plaques as a result of the accumulation of fatty materials such as cholesterol and triglycerides. Atherosclerosis frequently involves a chronic inflammatory response in the walls of arteries, caused largely by the accumulation of macrophages and promoted by low-density lipoproteins (LDL) without adequate removal of fats and cholesterol from the macrophages by functional high-density lipoproteins. Chronically expanding atherosclerotic lesions can cause complete closure of the lumen, which may only manifest when the lumen stenosis is so severe that blood supply to downstream tissue(s) is insufficient, resulting in ischemia.

The IL-10 polypeptides may be particularly advantageous in the treatment and/or prevention of cholesterol-related disorders, which may be associated with, for example, cardiovascular disease (e.g. atherosclerosis), cerebrovascular disease (e.g., stroke), and peripheral vascular disease. By way of example, but not limitation, the IL-10 polypeptides may be used for lowering a subject's blood cholesterol level. In determining whether a subject has hypercholesterolemia, there is no firm demarcation between normal and abnormal cholesterol levels, and interpretation of values needs to be made in relation to other health conditions and risk factors. Nonetheless, the following guidelines are generally used in the United States: total cholesterol <200 mg/dL is desirable, 200-239 mg/dL is borderline high, and ≥240 mg/dL is high. Higher levels of total cholesterol increase the risk of cardiovascular disease, and levels of LDL or non-HDL cholesterol are both predictive of future coronary heart disease. When assessing hypercholesterolemia, it is frequently useful to measure all lipoprotein subfractions (VLDL, IDL, LDL and HDL). A particular therapeutic goal is to decrease LDL while maintaining or increasing HDL.

Thrombosis and Thrombotic Conditions.

Thrombosis, the formation of a thrombus (blood clot) inside a blood vessel resulting in obstruction of the flow of blood through the circulatory system, may be caused by abnormalities in one or more of the following (Virchow's triad): hypercoagulability or increased blood clotting, endothelial cell injury, or disturbed blood flow (stasis, turbulence).

Thrombosis is generally categorized as venous or arterial, each of which can be presented by several subtypes. Venous thrombosis includes deep vein thrombosis (DVT), portal vein thrombosis, renal vein thrombosis, jugular vein thrombosis, Budd-Chiari syndrome, Paget-Schroetter disease, and cerebral venous sinus thrombosis. Arterial thrombosis includes stroke and myocardial infarction.

Other diseases, disorders and conditions are contemplated by the present disclosure, including atrial thrombosisand Polycythemia vera (also known as erythema, primary polycythemia and polycythemia rubra vera), a myeloproliferative blood disorder in which the bone marrow makes too many RBCs, WBCs and/or platelets.

Immune and Inflammatory Conditions.

As used herein, terms such as "immune disease", "immune condition", "immune disorder", "inflammatory disease", "inflammatory condition", "inflammatory disorder" and the like are meant to broadly encompass any immune- or inflammatory-related condition (e.g., pathological inflammation and autoimmune diseases). Such conditions frequently are inextricably intertwined with other diseases, disorders and conditions. By way of example, an "immune condition" may refer to proliferative conditions, such as cancer, tumors, and angiogenesis, including infections (acute and chronic), tumors, and cancers that resist eradication by the immune system.

A non-limiting list of immune- and inflammatory-related diseases, disorders and conditions which may, for example, be caused by inflammatory cytokines, include, arthritis, kidney failure, lupus, asthma, psoriasis, colitis, pancreatitis, allergies, fibrosis, surgical complications (e.g., where inflammatory cytokines prevent healing), anemia, and fibromyalgia. Other diseases and disorders which may be associated with chronic inflammation include Alzheimer's disease, congestive heart failure, stroke, aortic valve stenosis, arteriosclerosis, osteoporosis, Parkinson's disease, infections, inflammatory bowel disease (e.g., Crohn's disease and ulcerative colitis), allergic contact dermatitis and other eczemas, systemic sclerosis, transplantation and multiple sclerosis.

Some of the aforementioned diseases, disorders and conditions for which IL-10 (e.g., PEG-IL-10) may be particularly efficacious (due to, for example, limitations of current therapies) are described in more detail hereafter.

The IL-10 polypeptides of the present disclosure may be particularly effective in the treatment and prevention of inflammatory bowel diseases (IBD). IBD comprises Crohn's disease (CD) and ulcerative colitis (UC), both of which are idiopathic chronic diseases that can affect any part of the gastrointestinal tract, and are associated with many untoward effects, and patients with prolonged UC are at an increased risk of developing colon cancer. Current IBD treatments are aimed at controlling inflammatory symptoms, and while certain agents (e.g., corticosteroids, aminosalicylates and standard immunosuppressive agents (e.g., cyclosporine, azathioprine, and methotrexate)) have met with limited success, long-term therapy may cause liver damage (e.g., fibrosis or cirrhosis) and bone marrow suppression, and patients often become refractory to such treatments.

Psoriasis, a constellation of common immune-mediated chronic skin diseases, affects more than 4.5 million people in the U.S., of which 1.5 million are considered to have a moderate-to severe form of the disease. Moreover, over 10% of patients with psoriasis develop psoriatic arthritis, which damages the bone and connective tissue around the joints. An improved understanding of the underlying physiology of psoriasis has resulted in the introduction of agents that, for example, target the activity of T lymphocytes and cytokines responsible for the inflammatory nature of the disease. Such agents include the TNF-α inhibitors (also used in the treatment of rheumatoid arthritis (RA)), including ENBREL (etanercept), REMICADE (infliximab) and HUMIRA (adalimumab)), and T-cell inhibitors such as AMEVIVE (alefacept) and RAPTIVA (efalizumab). Though several of these agents are effective to some extent in certain patient populations, none have been shown to effectively treat all patients.

Rheumatoid Arthritis (RA), which is generally characterized by chronic inflammation in the membrane lining (the synovium) of the joints, affects approximately 1% of the U.S. population, or 2.1 million people in the U.S. Further understanding of the role of cytokines, including TNF-α and IL-1, in the inflammatory process has enabled the development and introduction of a new class of disease-modifying antirheumatic drugs (DMARDs). Agents (some of which overlap with treatment modalities for RA) include ENBREL (etanercept), REMICADE (infliximab), HUMIRA (adalimumab) and KINERET (anakinra) Though some of these agents relieve symptoms, inhibit progression of structural damage, and improve physical function in particular patient populations, there is still a need for alternative agents with improved efficacy, complementary mechanisms of action, and fewer/less severe adverse effects.

Subjects suffering from multiple sclerosis (MS), a seriously debilitating autoimmune disease comprising multiple areas of inflammation and scarring of the myelin in the brain and spinal cord, may be particularly helped by the IL-10 polypeptides described herein, as current treatments only alleviate symptoms or delay the progression of disability.

Similarly, the IL-10 polypeptides may be particularly advantageous for subjects afflicted with neurodegenerative disorders, such as Alzheimer's disease (AD), a brain disorder that seriously impairs patients' thought, memory, and language processes, and Parkinson's disease (PD), a progressive disorder of the CNS characterized by, for example, abnormal movement, rigidity and tremor. These disorders are progressive and debilitating, and no curative agents are available.

Viral Diseases.

There has been increased interest in the role of IL-10 in viral diseases. IL-10 has been postulated to produce both stimulatory and inhibitory effects depending on its receptor binding activity.

For example, the effect of inhibiting IL-10 function in order to increase antiviral immunity and vaccine efficacy has been considered (see Wilson, E., (2011) Curr Top Microbiol Immunol. 350: 39-65). Moreover, the role of IL-10 in human immunodeficiency virus (HIV) function has been studied. In addition to the inhibition of human immunodeficiency virus type 1 (HIV-1) replication, IL-10 may also promote viral persistence by inactivation of effector immune mechanisms (Naicker, D., et al., (2009) J Infect Dis. 200 (3):448-452). Another study has identified an IL-10-producing subset of B cells able to regulate T cell immunity in chronic hepatitis B virus (HBV) infection.

Although the aforementioned studies indicate that IL-10 inhibition may be beneficial, particular viral infections that comprise a CD8+ T cell component may be candidates for treatment and/or prevention through the administration of IL-10. This is supported by the positive role that IL-10 plays in certain cancers by modulation of regulatory T cells and/or CD8+ T cells.

The present disclosure contemplates the use of the IL-10 polypeptides in the treatment and/or prevention of any viral disease, disorder or condition for which treatment with IL-10 may be beneficial. Examples of viral diseases, disorders and conditions that are contemplated include hepatitis B, hepatitis C, HIV, herpes virus and cytomegalovirus (CMV).

Pharmaceutical Compositions

The IL-10 polypeptides of the present disclosure may be in the form of compositions suitable for administration to a subject. In general, such compositions are "pharmaceutical compositions" comprising IL-10 and one or more pharmaceutically acceptable or physiologically acceptable diluents, carriers or excipients. In certain embodiments, the IL-10 polypeptides are present in a therapeutically acceptable amount. The pharmaceutical compositions may be used in the methods of the present disclosure; thus, for example, the pharmaceutical compositions can be administered ex vivo or in vivo to a subject in order to practice the therapeutic and prophylactic methods and uses described herein.

The pharmaceutical compositions of the present disclosure can be formulated to be compatible with the intended method or route of administration; exemplary routes of administration are set forth herein. Furthermore, the pharmaceutical compositions may be used in combination with other therapeutically active agents or compounds as described herein in order to treat or prevent the diseases, disorders and conditions as contemplated by the present disclosure.

The pharmaceutical compositions typically comprise a therapeutically effective amount of an IL-10 polypeptide contemplated by the present disclosure and one or more pharmaceutically and physiologically acceptable formulation agents. Suitable pharmaceutically acceptable or physiologically acceptable diluents, carriers or excipients include, but are not limited to, antioxidants (e.g., ascorbic acid and sodium bisulfate), preservatives (e.g., benzyl alcohol, methyl parabens, ethyl or n-propyl, p-hydroxybenzoate), emulsifying agents, suspending agents, dispersing agents, solvents, fillers, bulking agents, detergents, buffers, vehicles, diluents, and/or adjuvants. For example, a suitable vehicle may be physiological saline solution or citrate buffered saline, possibly supplemented with other materials common in pharmaceutical compositions for parenteral administration. Neutral buffered saline or saline mixed with serum albumin are further exemplary vehicles. Those skilled in the art will readily recognize a variety of buffers that can be used in the pharmaceutical compositions and dosage forms contemplated herein. Typical buffers include, but are not limited to, pharmaceutically acceptable weak acids, weak bases, or mixtures thereof. As an example, the buffer components can be water soluble materials such as phosphoric acid, tartaric acids, lactic acid, succinic acid, citric acid, acetic acid, ascorbic acid, aspartic acid, glutamic acid, and salts thereof. Acceptable buffering agents include, for example, a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), and N-tris[Hydroxymethyl]methyl-3-aminopropanesulfonic acid (TAPS).

After a pharmaceutical composition has been formulated, it may be stored in sterile vials as a solution, suspension, gel, emulsion, solid, or dehydrated or lyophilized powder. Such formulations may be stored either in a ready-to-use form, a lyophilized form requiring reconstitution prior to use, a liquid form requiring dilution prior to use, or other acceptable form. In some embodiments, the pharmaceutical composition is provided in a single-use container (e.g., a single-use vial, ampoule, syringe, or autoinjector (similar to, e.g., an EpiPen®)), whereas a multi-use container (e.g., a multi-use vial) is provided in other embodiments. Any drug delivery apparatus may be used to deliver IL-10, including implants (e.g., implantable pumps) and catheter systems, slow injection pumps and devices, all of which are well known to the skilled artisan. Depot injections, which are generally administered subcutaneously or intramuscularly, may also be utilized to release the polypeptides disclosed herein over a defined period of time. Depot injections are usually either solid- or oil-based and generally comprise at least one of the formulation components set forth herein. One of ordinary skill in the art is familiar with possible formulations and uses of depot injections.

The pharmaceutical compositions may be in the form of a sterile injectable aqueous or oleagenous suspension. This suspension may be formulated according to the known art using those suitable dispersing or wetting agents and suspending agents mentioned herein. The sterile injectable preparation may also be a sterile injectable solution or suspension in a non-toxic parenterally-acceptable diluent or solvent, for example, as a solution in 1,3-butane diol. Acceptable diluents, solvents and dispersion media that may be employed include water, Ringer's solution, isotonic sodium chloride solution, Cremophor EL™ (BASF, Parsippany, N.J.) or phosphate buffered saline (PBS), ethanol, polyol (e.g., glycerol, propylene glycol, and liquid polyethylene glycol), and suitable mixtures thereof. In addition, sterile, fixed oils are conventionally employed as a solvent or suspending medium. For this purpose any bland fixed oil may be employed, including synthetic mono- or diglycerides. Moreover, fatty acids such as oleic acid, find use in the preparation of injectables. Prolonged absorption of particular injectable formulations can be achieved by including an agent that delays absorption (e.g., aluminum monostearate or gelatin).

The pharmaceutical compositions containing the active ingredient may be in a form suitable for oral use, for example, as tablets, capsules, troches, lozenges, aqueous or oily suspensions, dispersible powders or granules, emulsions, hard or soft capsules, or syrups, solutions, microbeads or elixirs. Pharmaceutical compositions intended for oral use may be prepared according to any method known to the art for the manufacture of pharmaceutical compositions, and such compositions may contain one or more agents such as, for example, sweetening agents, flavoring agents, coloring agents and preserving agents in order to provide pharmaceutically elegant and palatable preparations. Tablets, capsules and the like contain the active ingredient in admixture with non-toxic pharmaceutically acceptable excipients which are suitable for the manufacture of tablets. These excipients may be, for example, diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc.

The tablets, capsules and the like suitable for oral administration may be uncoated or coated by known techniques to delay disintegration and absorption in the gastrointestinal tract and thereby provide a sustained action. For example, a time-delay material such as glyceryl monostearate or glyceryl distearate may be employed. They may also be coated by techniques known in the art to form osmotic therapeutic tablets for controlled release. Additional agents include biodegradable or biocompatible particles or a polymeric substance such as polyesters, polyamine acids, hydrogel, polyvinyl pyrrolidone, polyanhydrides, polyglycolic acid, ethylene-vinylacetate, methylcellulose, carboxymethylcellulose, protamine sulfate, or lactide/glycolide copolymers, polylactide/glycolide copolymers, or ethylenevinylacetate copolymers in order to control delivery of an administered composition. For example, the oral agent can be entrapped in microcapsules prepared by coacervation techniques or by interfacial polymerization, by the use of hydroxymethylcellulose or gelatin-microcapsules or poly (methylmethacrolate) microcapsules, respectively, or in a colloid drug delivery system. Colloidal dispersion systems include macromolecule complexes, nano-capsules, microspheres, microbeads, and lipid-based systems, including oil-in-water emulsions, micelles, mixed micelles, and liposomes. Methods for the preparation of the above-mentioned formulations will be apparent to those skilled in the art.

Formulations for oral use may also be presented as hard gelatin capsules wherein the active ingredient is mixed with an inert solid diluent, for example, calcium carbonate, calcium phosphate, kaolin or microcrystalline cellulose, or as soft gelatin capsules wherein the active ingredient is mixed with water or an oil medium, for example peanut oil, liquid paraffin, or olive oil.

Aqueous suspensions contain the active materials in admixture with excipients suitable for the manufacture thereof. Such excipients can be suspending agents, for example sodium carboxymethylcellulose, methylcellulose, hydroxy-propylmethylcellulose, sodium alginate, polyvinylpyrrolidone, gum tragacanth and gum acacia; dispersing or wetting agents, for example a naturally-occurring phosphatide (e.g., lecithin), or condensation products of an alkylene oxide with fatty acids (e.g., polyoxy-ethylene stearate), or condensation products of ethylene oxide with long chain aliphatic alcohols (e.g., for heptadecaethyleneoxycetanol), or condensation products of ethylene oxide with partial esters derived from fatty acids and a hexitol (e.g., polyoxy-ethylene sorbitol monooleate), or condensation products of ethylene oxide with partial esters derived from fatty acids and hexitol anhydrides (e.g., polyethylene sorbitan monooleate). The aqueous suspensions may also contain one or more preservatives.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified herein.

The pharmaceutical compositions of the present disclosure may also be in the form of oil-in-water emulsions. The oily phase may be a vegetable oil, for example olive oil or arachis oil, or a mineral oil, for example, liquid paraffin, or mixtures of these. Suitable emulsifying agents may be naturally occurring gums, for example, gum acacia or gum tragacanth; naturally occurring phosphatides, for example, soy bean, lecithin, and esters or partial esters derived from fatty acids; hexitol anhydrides, for example, sorbitan monooleate; and condensation products of partial esters with ethylene oxide, for example, polyoxyethylene sorbitan monooleate.

Formulations can also include carriers to protect the composition against rapid degradation or elimination from the body, such as a controlled release formulation, including implants, liposomes, hydrogels, prodrugs and microencapsulated delivery systems. For example, a time delay material such as glyceryl monostearate or glyceryl stearate alone, or in combination with a wax, may be employed.

The present disclosure contemplates the administration of the IL-10 polypeptides in the form of suppositories for rectal administration. The suppositories can be prepared by mixing the drug with a suitable non-irritating excipient which is solid at ordinary temperatures but liquid at the rectal temperature and will therefore melt in the rectum to release the drug. Such materials include, but are not limited to, cocoa butter and polyethylene glycols.

The IL-10 polypeptides contemplated by the present disclosure may be in the form of any other suitable pharmaceutical composition (e.g., sprays for nasal or inhalation use) currently known or developed in the future.

The concentration of a polypeptide or fragment thereof in a formulation can vary widely (e.g., from less than about 0.1%, usually at or at least about 2% to as much as 20% to 50% or more by weight) and will usually be selected primarily based on fluid volumes, viscosities, and subject-based factors in accordance with, for example, the particular mode of administration selected.

Routes of Administration

The present disclosure contemplates the administration of IL-10, and compositions thereof, in any appropriate manner. Suitable routes of administration include parenteral (e.g., intramuscular, intravenous, subcutaneous (e.g., injection or implant), intraperitoneal, intracisternal, intraarticular, intraperitoneal, intracerebral (intraparenchymal) and intracerebroventricular), oral, nasal, vaginal, sublingual, intraocular, rectal, topical (e.g., transdermal), sublingual and inhalation. Depot injections, which are generally administered subcutaneously or intramuscularly, may also be utilized to release the IL-10 polypeptides disclosed herein over a defined period of time.

Particular embodiments of the present disclosure contemplate parenteral administration, and in further particular embodiments the parenteral administration is subcutaneous.

Combination Therapy

The present disclosure contemplates the use of IL-10 (e.g., PEG-IL-10) in combination with one or more active therapeutic agents (e.g., cytokines) or other prophylactic or therapeutic modalities (e.g., radiation). In such combination therapy, the various active agents frequently have different mechanisms of action. Such combination therapy may be especially advantageous by allowing a dose reduction of one or more of the agents, thereby reducing or eliminating the adverse effects associated with one or more of the agents; furthermore, such combination therapy may have a synergistic therapeutic or prophylactic effect on the underlying disease, disorder, or condition.

As used herein, "combination" is meant to include therapies that can be administered separately, for example, formulated separately for separate administration (e.g., as may be provided in a kit), and therapies that can be administered together in a single formulation (i.e., a "co-formulation").

In certain embodiments, the IL-10 polypeptides are administered or applied sequentially, e.g., where one agent is administered prior to one or more other agents. In other embodiments, the IL-10 polypeptides are administered simultaneously, e.g., where two or more agents are administered at or about the same time; the two or more agents may be present in two or more separate formulations or combined into a single formulation (i.e., a co-formulation). Regardless of whether the two or more agents are administered sequentially or simultaneously, they are considered to be administered in combination for purposes of the present disclosure.

The IL-10 polypeptides of the present disclosure may be used in combination with one or more other (active) agent in any manner appropriate under the circumstances. In one embodiment, treatment with the at least one active agent and at least one IL-10 polypeptide of the present disclosure is maintained over a period of time. In another embodiment, treatment with the at least one active agent is reduced or discontinued (e.g., when the subject is stable), while treatment with the IL-10 polypeptide of the present disclosure is maintained at a constant dosing regimen. In a further embodiment, treatment with the at least one active agent is reduced or discontinued (e.g., when the subject is stable), while treatment with the IL-10 polypeptide of the present disclosure is reduced (e.g., lower dose, less frequent dosing or shorter treatment regimen). In yet another embodiment, treatment with the at least one active agent is reduced or discontinued (e.g., when the subject is stable), and treatment with the IL-10 polypeptide of the present disclosure is increased (e.g., higher dose, more frequent dosing or longer treatment regimen). In yet another embodiment, treatment with the at least one active agent is maintained and treatment with the IL-10 polypeptide of the present disclosure is reduced or discontinued (e.g., lower dose, less frequent dosing or shorter treatment regimen). In yet another embodiment, treatment with the at least one active agent and treatment with the IL-10 polypeptide of the present disclosure are reduced or discontinued (e.g., lower dose, less frequent dosing or shorter treatment regimen).

Fibrotic Disorders and Cancer.

The present disclosure provides methods for treating and/or preventing a proliferative condition, cancer, tumor, or precancerous disease, disorder or condition with an IL-10 polypeptide (e.g., PEG-IL-10) and at least one additional therapeutic or diagnostic agent.

Examples of chemotherapeutic agents include, but are not limited to, alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamime; nitrogen mustards such as chiorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside (Ara-C); cyclophosphamide; thiotepa; taxoids, e.g., paclitaxel and doxetaxel; chlorambucil; gemcitabine; 6-thioguanine; mercaptopurine; methotrexate; platinum and platinum coordination complexes such as cisplatin and carboplatin; vinblastine; etoposide (VP-16); ifosfamide; mitomycin C; mitoxantrone; vincristine; vinorelbine; navelbine; novantrone; teniposide; daunomycin; aminopterin; xeloda; ibandronate; CPT11; topoisomerase inhibitors; difluoromethylornithine (DMFO); retinoic acid; esperamicins; capecitabine; and pharmaceutically acceptable salts, acids or derivatives of any of the above.

Chemotherapeutic agents also include anti-hormonal agents that act to regulate or inhibit hormone action on tumors such as anti-estrogens, including for example tamoxifen, raloxifene, aromatase inhibiting 4(5)-imidazoles, 4-hydroxytamoxifen, trioxifene, keoxifene, onapristone, and toremifene; and antiandrogens such as flutamide, nilutamide, bicalutamide, leuprolide, and goserelin; and pharmaceutically acceptable salts, acids or derivatives of any of the above. In certain embodiments, combination therapy comprises administration of a hormone or related hormonal agent.

Additional treatment modalities that may be used in combination with the IL-10 polypeptides include a cytokine or cytokine antagonist, such as IL-12, INFα, or anti-epidermal growth factor receptor, radiotherapy, a monoclonal antibody against another tumor antigen, a complex of a monoclonal antibody and toxin, a T-cell adjuvant, bone marrow transplant, or antigen presenting cells (e.g., dendritic cell therapy). Vaccines (e.g., as a soluble protein or as a nucleic acid encoding the protein) are also provided herein.

Cardiovascular Diseases.

The present disclosure provides methods for treating and/or preventing certain cardiovascular- and/or metabolic-related diseases, disorders and conditions, as well as disorders associated therewith, with an IL-10 polypeptide (e.g., PEG-IL-10) and at least one additional therapeutic or diagnostic agent.

Examples of therapeutic agents useful in combination therapy for the treatment of hypercholesterolemia (and thus frequently atherosclerosis) include statins (e.g., CRESTOR, LESCOL, LIPITOR, MEVACOR, PRAVACOL, and ZOCOR), which inhibit the enzymatic synthesis of cholesterol; bile acid resins (e.g., COLESTID, LO-CHOLEST, PREVALITE, QUESTRAN, and WELCHOL), which sequester cholesterol and prevent its absorption; ezetimibe (ZETIA), which blocks cholesterol absorption; fibric acid (e.g., TRICOR), which reduce triglycerides and may modestly increase HDL; niacin (e.g., NIACOR), which modestly lowers LDL cholesterol and triglycerides; and/or a combination of the aforementioned (e.g., VYTORIN (ezetimibe with simvastatin)). Alternative cholesterol treatments that may be candidates for use in combination with the IL-10 polypeptides described herein include various supplements and herbs (e.g., garlic, policosanol, and guggul). The present disclosure encompasses pharmaceutically acceptable salts, acids or derivatives of any of the above.

Immune and Inflammatory Conditions.

The present disclosure provides methods for treating and/or preventing immune- and/or inflammatory-related diseases, disorders and conditions, as well as disorders associated therewith, with an IL-10 polypeptide (e.g., PEG-IL-10) and at least one additional therapeutic or diagnostic agent.

Examples of therapeutic agents useful in combination therapy include, but are not limited to, the following: non-steroidal anti-inflammatory drug (NSAID) such as aspirin, ibuprofen, and other propionic acid derivatives (alminoprofen, benoxaprofen, bucloxic acid, carprofen, fenbufen, fenoprofen, fluprofen, flurbiprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, fuirofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone). Other combinations include cyclooxygenase-2 (COX-2) inhibitors.

Other active agents for combination include steroids such as prednisolone, prednisone, methylprednisolone, betamethasone, dexamethasone, or hydrocortisone. Such a combination may be especially advantageous, since one or more sideeffects of the steroid can be reduced or even eliminated by tapering the steroid dose required when treating patients in combination with the present IL-10 polypeptides.

Additional examples of active agents for combinations for treating, for example, rheumatoid arthritis include cytokine suppressive anti-inflammatory drug(s) (CSAIDs); antibodies to or antagonists of other human cytokines or growth factors, for example, TNF, LT, IL-1β., IL-2, IL-6, IL-7, IL-8, IL-15, IL-16, IL-18, EMAP-II, GM-CSF, FGF, or PDGF.

Particular combinations of active agents may interfere at different points in the autoimmune and subsequent inflammatory cascade, and include TNF antagonists like chimeric, humanized or human TNF antibodies, REMICADE, anti-TNF antibody fragments (e.g., CDP870), and soluble p55 or p75 TNF receptors, derivatives thereof, p75TNFRIgG (ENBREL.) or p55TNFR1gG (LENERCEPT), soluble IL-13 receptor (sIL-13), and also TNFα converting enzyme (TACE) inhibitors; similarly IL-1 inhibitors (e.g., Interleukin-1-converting enzyme inhibitors) may be effective. Other combinations include Interleukin 11, anti-P7s and p-selectin glycoprotein ligand (PSGL). Other examples of agents useful in combination with the IL-10 polypeptides described herein include interferon-β1a (AVONEX); interferon-β1b (BETASERON); copaxone; hyperbaric oxygen; intravenous immunoglobulin; clabribine; and antibodies to or antagonists of other human cytokines or growth factors (e.g., antibodies to CD40 ligand and CD80).

The present disclosure encompasses pharmaceutically acceptable salts, acids or derivatives of any of the above.

Viral Diseases.

The present disclosure provides methods for treating and/or preventing viral diseases, disorders and conditions, as well as disorders associated therewith, with an IL-10 polypeptide (e.g., PEG-IL-10) and at least one additional therapeutic or diagnostic agent (e.g., one or more other anti-viral agents and/or one or more other non-viral agents).

Such combination therapy includes anti-viral agents targeting various viral life-cycle stages and having different mechanisms of action, including, but not limiting to, the following: inhibitors of viral uncoating (e.g., amantadine and rimantidine); reverse transcriptase inhibititors (e.g., acyclovir, zidovudine, and lamivudine); agents that target integrase; agents that block attachment of transcription factors to viral DNA; agents (e.g., antisense molecules) that impact translation (e.g., fomivirsen); agents that modulate translation/ribozyme function; protease inhibitors; viral assembly modulators (e.g., rifampicin); and agents that prevent release of viral particles (e.g., zanamivir and oseltamivir). Treatment and/or prevention of certain viral infections (e.g., HIV) frequently entail a group ("cocktail") of antiviral agents.

Other antiviral agents contemplated for use in combination with IL-10 polypeptides include, but are not limited to, the following: abacavir, adefovir, amantadine, amprenavir, ampligen, arbidol, atazanavir, atripla, boceprevirertet, cidofovir, combivir, darunavir, delavirdine, didanosine, docosanol, edoxudine, efavirenz, emtricitabine, enfuvirtide, entecavir, famciclovir, fosamprenavir, foscarnet, fosfonet, ganciclovir, ibacitabine, imunovir, idoxuridine, imiquimod, indinavir, inosine, various interferons (e.g., peginterferon alfa-2a), lopinavir, loviride, maraviroc, moroxydine, methisazone, nelfinavir, nevirapine, nexavir, penciclovir, peramivir, pleconaril, podophyllotoxin, raltegravir, ribavirin, ritonavir, pyramidine, saquinavir, stavudine, telaprevir, tenofovir, tipranavir, trifluridine, trizivir, tromantadine, truvada, valaciclovir, valganciclovir, vicriviroc, vidarabine, viramidine, and zalcitabine.

The present disclosure encompasses pharmaceutically acceptable salts, acids or derivatives of any of the above.

Dosing

The IL-10 polypeptides of the present disclosure may be administered to a subject in an amount that is dependent upon, for example, the goal of the administration (e.g., the degree of resolution desired); the age, weight, sex, and health and physical condition of the subject the formulation being administered; the route of administration; and the nature of the disease, disorder, condition or symptom thereof. The dosing regimen may also take into consideration the existence, nature, and extent of any adverse effects associated with the agent(s) being administered. Effective dosage amounts and dosage regimens can readily be determined from, for example, safety and dose-escalation trials, in vivo studies (e.g., animal models), and other methods known to the skilled artisan.

The present disclosure contemplates administration of IL-10 to achieve certain serum trough concentrations and/or maintain certain mean serum trough concentrations. Methodologies specific to IL-10 are described elsewhere herein and in this section below.

In general, dosing parameters dictate that the dosage amount be less than an amount that could be irreversibly toxic to the subject (i.e., the maximum tolerated dose, "MTD") and not less than an amount required to produce a measurable effect on the subject. Such amounts are determined by, for example, the pharmacokinetic and pharmacodynamic parameters associated with ADME, taking into consideration the route of administration and other factors.

An effective dose (ED) is the dose or amount of an agent that produces a therapeutic response or desired effect in some fraction of the subjects taking it. The "median effective dose" or ED50 of an agent is the dose or amount of an agent that produces a therapeutic response or desired effect in 50% of the population to which it is administered. Although the ED50 is commonly used as a measure of reasonable expectance of an agent's effect, it is not necessarily the dose that a clinician might deem appropriate taking into consideration all relevant factors. Thus, in some situations the effective amount is more than the calculated ED50, in other situations the effective amount is less than the calculated ED50, and in still other situations the effective amount is the same as the calculated ED50.

In addition, an effective dose of the IL-10 polypeptide of the present disclosure may be an amount that, when administered in one or more doses to a subject, produces a desired result relative to a healthy subject. For example, for a subject experiencing a particular disorder, an effective dose may be one that improves a diagnostic parameter, measure, marker and the like of that disorder by at least about 5%, at least about 10%, at least about 20%, at least about 25%, at least about 30%, at least about 40%, at least about 50%, at least about 60%, at least about 70%, at least about 80%, at least about 90%, or more than 90%, where 100% is defined as the diagnostic parameter, measure, marker and the like exhibited by a normal subject.

The amount of PEG-IL-10 necessary to treat a disease, disorder or condition described herein is based on the IL-10 activity of the conjugated protein, which can be determined by IL-10 activity assays known in the art. By way of example, in the tumor context, suitable IL-10 activity includes, for example, CD8+ T-cell infiltrate into tumor sites, expression of inflammatory cytokines, such as IFN-γ, IL-4, IL-6, IL-10, and RANK-L, from these infiltrating cells, and increased levels of IFN-γ in biological samples.

The therapeutically effective amount of an IL-10 agent can range from about 0.01 to about 100 μg protein/kg of body weight/day, from about 0.1 to 20 μg protein/kg of body weight/day, from about 0.5 to 10 μg protein/kg of body weight/day, or about 1 to 4 μg protein/kg of body weight/day. In some embodiments, an IL-10 agent is administered by continuous infusion to deliver about 50 to 800 μg protein/kg of body weight/day (e.g., about 1 to 16 μg protein/kg of body weight/day of the IL-10 agent). The infusion rate may be varied based on evaluation of, for example, adverse effects and blood cell counts.

For administration of an oral agent, the compositions can be provided in the form of tablets, capsules and the like containing from 1.0 to 1000 milligrams of the active ingredient, particularly 1.0, 3.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient.

Particular dosing regimens (e.g., dosing frequencies) for the IL-10 polypeptides are described elsewhere herein.

In certain embodiments, the dosage of the disclosed IL-10 polypeptide is contained in a "unit dosage form". The phrase "unit dosage form" refers to physically discrete units, each unit containing a predetermined amount of a IL-10 polypeptide of the present disclosure, either alone or in combination with one or more additional agents, sufficient to produce the desired effect. It will be appreciated that the parameters of a unit dosage form will depend on the particular agent and the effect to be achieved.

Kits

The present disclosure also contemplates kits comprising IL-10, and pharmaceutical compositions thereof. The kits are generally in the form of a physical structure housing various components, as described below, and may be utilized, for example, in practicing the methods described above (e.g., administration of a IL-10 polypeptide to a subject in need of restoring cholesterol homeostasis).

A kit can include one or more of the IL-10 polypeptides disclosed herein (provided in, e.g., a sterile container), which may be in the form of a pharmaceutical composition suitable for administration to a subject. The IL-10 polypeptides can be provided in a form that is ready for use or in a form requiring, for example, reconstitution or dilution prior to administration. When the IL-10 polypeptides are in a form that needs to be reconstituted by a user, the kit may also include buffers, pharmaceutically acceptable excipients, and the like, packaged with or separately from the IL-10 polypeptides. When combination therapy is contemplated, the kit may contain the several agents separately or they may already be combined in the kit. Each component of the kit may be enclosed within an individual container, and all of the various containers may be within a single package. A kit of the present disclosure may be designed for conditions necessary to properly maintain the components housed therein (e.g., refrigeration or freezing).

A kit may contain a label or packaging insert including identifying information for the components therein and instructions for their use (e.g., dosing parameters, clinical pharmacology of the active ingredient(s), including mechanism of action, pharmacokinetics and pharmacodynamics, adverse effects, contraindications, etc.). Labels or inserts can include manufacturer information such as lot numbers and expiration dates. The label or packaging insert may be, e.g., integrated into the physical structure housing the components, contained separately within the physical structure, or affixed to a component of the kit (e.g., an ampule, tube or vial).

Labels or inserts can additionally include, or be incorporated into, a computer readable medium, such as a disk (e.g., hard disk, card, memory disk), optical disk such as CD- or DVD-ROM/RAM, DVD, MP3, magnetic tape, or an electrical storage media such as RAM and ROM or hybrids of these such as magnetic/optical storage media, FLASH media or memory-type cards. In some embodiments, the actual instructions are not present in the kit, but means for obtaining the instructions from a remote source, e.g., via the internet, are provided.

EXPERIMENTAL

The following examples are put forth so as to provide those of ordinary skill in the art with a complete disclosure and description of how to make and use the present invention, and are not intended to limit the scope of what the inventors regard as their invention nor are they intended to represent that the experiments below were performed and are all of the experiments that may be performed. It is to be understood that exemplary descriptions written in the present tense were not necessarily performed, but rather that the descriptions can be performed to generate the data and the like described therein. Efforts have been made to ensure accuracy with respect to numbers used (e.g., amounts, temperature, etc.), but some experimental errors and deviations should be accounted for.

Unless indicated otherwise, parts are parts by weight, molecular weight is weight average molecular weight, temperature is in degrees Celsius (° C.), and pressure is at or near atmospheric. Standard abbreviations are used, including the following: bp=base pair(s); kb=kilobase(s); pl=picoliter(s); s or sec=second(s); min=minute(s); h or hr=hour(s); aa=amino acid(s); kb=kilobase(s); nt=nucleotide(s); ng=nanogram; µg=microgram; mg=milligram; g=gram; kg=kilogram; dl or dL=deciliter; µl or µL=microliter; ml or mL=milliliter; l or L=liter; µM=micromolar; mM=millimolar; M=molar; kDa=kilodalton; i.m.=intramuscular(ly); i.p.=intraperitoneal (ly); i.v. or IV=intravenous(ly); s.c. or SC=subcutaneous (ly); QD=daily; BID=twice daily; QW=weekly; QM=monthly; HPLC=high performance liquid chromatography; BW=body weight; U=unit; ns=not statistically significant; PBS=phosphate-buffered saline; PCR=polymerase chain reaction; NHS=N-Hydroxysuccinimide; DMEM=Dulbeco's Modification of Eagle's Medium; GC=genome copy; EDTA=ethylenediaminetetraacetic acid.

Materials and Methods

The following general materials and methods may be used in the Examples below:

Standard methods in molecular biology are described (see, e.g., Sambrook and Russell (2001) Molecular Cloning, 3$^{rd}$ ed., Cold Spring Harbor Laboratory Press, Cold Spring Harbor, N.Y.; and Ausubel, et al. (2001) Current Protocols in Molecular Biology, Vols. 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4)).

The scientific literature describes methods for protein purification, including immunoprecipitation, chromatography, electrophoresis, centrifugation, and crystallization, as well as chemical analysis, chemical modification, post-translational modification, production of fusion proteins, and glycosylation of proteins (see, e.g., Coligan, et al. (2000) Current Protocols in Protein Science, Vols. 1-2, John Wiley and Sons, Inc., NY).

Production, purification, and fragmentation of polyclonal and monoclonal antibodies are described (e.g., Harlow and Lane (1999) Using Antibodies, Cold Spring Harbor Laboratory Press, Cold Spring Harbor, N.Y.); standard techniques for characterizing ligand/receptor interactions are available (see, e.g., Coligan et al. (2001) Current Protocols in Immunology, Vol. 4, John Wiley, Inc., NY); methods for flow cytometry, including fluorescence-activated cell sorting (FACS), are available (see, e.g., Shapiro (2003) Practical Flow Cytometry, John Wiley and Sons, Hoboken, N.J.); and fluorescent reagents suitable for modifying nucleic acids, including nucleic acid primers and probes, polypeptides, and antibodies, for use, for example, as diagnostic reagents, are available (Molecular Probes (2003) Catalogue, Molecular Probes, Inc., Eugene, Oreg.; Sigma-Aldrich (2003) Catalogue, St. Louis, Mo.).

Standard methods of histology of the immune system are described (see, e.g., Louis et al. (2002) Basic Histology: Text and Atlas, McGraw-Hill, New York, N.Y.).

Depletion of immune cells (CD4$^+$ and CD8$^+$ T-cells) may be effected by antibody-mediated elimination. For example, 250 µg of CD4- or CD8-specific antibodies may be injected weekly, and cell depletions verified using FACS and IHC analysis.

Software packages and databases for determining, e.g., antigenic fragments, leader sequences, protein folding, functional domains, glycosylation sites, and sequence alignments, are available (see, e.g., GCG Wisconsin Package (Accelrys, Inc., San Diego, Calif.); and DeCypher™ (Time-Logic Corp., Crystal Bay, Nev.).

Immunocompetent Balb/C or B-cell-deficient Balb/C mice were obtained from The Jackson Lab., Bar Harbor, Me. and used in accordance with standard procedures (see, e.g., Martin et al (2001) Infect. Immun., 69(11):7067-73 and Compton et al. (2004) Comp. Med. 54(6):681-89). Other mice strains suitable for the experimental work contemplated by the present disclosure are known to the skilled artisan and are generally available from The Jackson Lab.

Unless otherwise indicated, PDV6 squamous cell carcinoma of the skin was used in the experiments described herein (see, e.g., Langowski et al. (2006) Nature 442:461-465). Other oncology-related models and cell lines, such as Ep2 mammary carcinoma, CT26 colon carcinoma, and 4T1 breast carcinoma models, may be used (see, e.g., Langowski et al. (2006) Nature 442:461-465) and are known to the skilled artisan. Non-oncology-related models and cell lines (e.g., models of inflammation) may also be used and are known to the skilled artisan.

Serum IL-10 concentration levels and exposure levels may be determined by standard methods used in the art. For example, a serum exposure level assay can be performed by collecting whole blood (~50 μl/mouse) from mouse tail snips into plain capillary tubes, separating serum and blood cells by centrifugation, and determining IL-10 exposure levels by standard ELISA kits and techniques. Additional means of determining IL-10 serum concentrations are described hereafter.

Production of Pegylated IL-10

The present disclosure contemplates the synthesis of pegylated IL-10 by any means known to the skilled artisan. The description hereafter of several alternative synthetic schemes for producing mono-PEG-IL-10 and a mix of mono-/di-PEG-IL-10 is meant to be illustrative only. While both mono-PEG-IL-10 and a mix of mono-/di-PEG-IL-10 have many comparable properties, a mix of selectively pegylated mono- and di-PEG-IL-10 improves the yield of the final pegylated product (see, e.g., U.S. Pat. No. 7,052,686 and US Pat. Publn. No. 2011/0250163).

In addition to leveraging her own skills in the production and use of PEGs (and other drug delivery technologies) suitable in the practice of the present disclosure, the skilled artisan is also familiar with many commercial suppliers of PEG-related technologies (and other drug delivery technologies). By way of example, NOF America Corp (Irvine, Calif.) supplies mono-functional Linear PEGs, bi-functional PEGs, multi-arm PESs, branched PEGs, heterofunctional PEGs, forked PEGs, and releasable PEGs; and Parchem (New Rochelle, N.Y.) is a global distributor of PEG products and other specialty raw materials.

Exemplary PEG-IL-10 Synthetic Scheme No. 1.

IL-10 may be dialyzed against 10 mM sodium phosphate at pH 7.0, 100 mM NaCl. The dialyzed IL-10 may then be diluted 3.2 times to a concentration of 4 mg/mL using the dialysis buffer. Prior to the addition of the linker, SC-PEG-12K (Delmar Scientific Labs, Maywood, Ill.), 1 volume of 100 mM Na-tetraborate at pH 9.1 can be added into 9 volumes of the diluted IL-10 to raise the pH of the IL-10 solution to 8.6. The SC-PEG-12K linker can be dissolved in the dialysis buffer and the appropriate volume of the linker solution (1.8 to 3.6 mole of linker/mole of IL-10) can be added into the diluted IL-10 solution to start the pegylation reaction. The reaction can be carried out at 5° C. in order to control the rate of the reaction. The reaction solution can be mildly agitated during the pegylation reaction. When the mono-PEG-IL-10 yield, as determined by size exclusion HPLC (SE-HPLC), is close to 40%, the reaction is stopped by adding 1M glycine solution to a final concentration of 30 mM. The pH of the reaction solution is slowly adjusted to 7.0 using an HCl solution, and the reaction solution is then filtered using a 0.2 micron filter and stored at −80° C.

Exemplary PEG-IL-10 Synthetic Scheme No. 2.

Mono-PEG-IL-10 is prepared using methoxy-PEG-aldehyde (PALD-PEG) as a linker (Inhale Therapeutic Systems Inc., Huntsville, Ala.; also available from NOF America Corp (Irvine, Calif.)). PALD-PEG can have molecular weights of 5 KDa, 12 KDa, or 20 KDa. IL-10 is dialyzed and diluted as described above, except the pH of the reaction buffer is between 6.3 and 7.5. Activated PALD-PEG linker is added to reaction buffer at a 1:1 molar ratio. Aqueous cyanoborohydride is added to the reaction mixture to a final concentration of 0.5 to 0.75 mM. The reaction is carried out at room temperature (18-25° C.) for 15-20 hours with mild agitation. The reaction is quenched with 1M glycine. Yields are analyzed by SE-HPLC. Mono-PEG-IL-10 is separated from unreacted IL-10, PEG linker and di-PEG-IL-10 by gel filtration chromatography and characterized by RP-HPLC and bioassay (e.g., stimulation of IL-10-responsive cells or cell lines).

Exemplary PEG-IL-10 Synthetic Scheme No. 3

IL-10 (e.g., rodent or primate) is dialyzed against 50 mM sodium phosphate, 100 mM sodium chloride pH ranges 5-7.4. A 1:1-1:7 molar ratio of 5K PEG-propyladehyde is reacted with IL-10 at a concentration of 1-12 mg/mL in the presence of 0.75-30 mM sodium cyanoborohydride. Alternatively the reaction can be activated with picoline borane in a similar manner. The reaction is incubated at 5-30° C. for 3-24 hours.

The pH of the pegylation reaction is adjusted to 6.3, 7.5 mg/mL of hIL-10 is reacted with PEG to make the ratio of IL-10 to PEG linker 1:3.5. The final concentration of cyanoborohydride is ~25 mM, and the reaction is carried out at 15° C. for 12-15 hours. The mono- and di-PEG IL-10 are the largest products of the reaction, with the concentration of each at ~45-50% at termination. The reaction may be quenched using an amino acid such as glycine or lysine or, alternatively, Tris buffers. Multiple purification methods can be employed such as gel filtration, anion and cation exchange chromatographies, and size exclusion HPLC (SE-HPLC) to isolate the desired pegylated IL-10 molecules.

Exemplary PEG-IL-10 Synthetic Scheme No. 4.

IL-10 is dialyzed against 10 mM sodium phosphate pH 7.0, 100 mM NaCl. The dialyzed IL-10 is diluted 3.2 times to a concentration of about 0.5 to 12 mg/mL using the dialysis buffer. Prior to the addition of the linker, SC-PEG-12K (Delmar Scientific Laboratories, Maywood, Ill.), one volume of 100 mM Na-tetraborate at pH 9.1 is added into 9 volumes of the diluted IL-10 to raise the pH of the IL-10 solution to 8.6. The SC-PEG-12K linker is dissolved in the dialysis buffer and the appropriate volume of the linker solution (1.8 to 3.6 mole linker per mole of IL-10) is added into the diluted IL-10 solution to initiate the pegylation reaction. The reaction is carried out at 5° C. in order to control the rate of the reaction, and the reaction solution is mildly agitated. When the mono-PEG-IL-10 yield, as determined by size exclusion HPLC (SE-HPLC), is close to 40%, the reaction is stopped by adding 1M glycine solution to a final concentration of 30 mM. The pH of the reaction solution is slowly adjusted to 7.0 using an HCl solution, and the reaction is 0.2 micron filtered and stored at −80° C.

The material set forth below, up to and including Table 15 and the description thereof, was essentially extracted from US Pat. Publn. No. 2011/00911419 (a co-inventor of US Pat. Publn. No. 2011/00911419 is also an inventor of the instant application), and the teachings therein, and variations thereof, are broadly applicable and can be utilized and/or modified in a number of different contexts. Similarly, the teachings of other publications in related fields and/or technology areas (see, e.g., U.S. Pat. Nos. 6,387,364 and 7,052,684, and PCT Publn No. WO 2006/075138), along with the general knowledge of the skilled artisan, can form the basis for additional experimental work.

Tumor Models and Tumor Analysis

Any art-accepted tumor model, assay, and the like can be used to evaluate the effect of IL-10 and PEG-IL-10 on various tumors. The tumor models and tumor analyses described hereafter are representative of those that can be utilized, and they were used to generate and assess the data set forth in Tables 1-15.

Syngeneic mouse tumor cells are injected subcutaneously or intradermally at $10^4$, $10^5$ or $10^6$ cells per tumor inoculation. Ep2 mammary carcinoma, CT26 colon carcinoma, PDV6 squamous carcinoma of the skin and 4T1 breast carcinoma models can be used (see, e.g., Langowski et al. (2006) Nature 442:461-465). Immunocompetent Balb/C or B cell deficient Balb/C mice can be used. PEG-mIL-10 can be administered to the immunocompetent mice, while PEG-hIL-10 treatment can be used in the B-cell deficient mice. Tumors are allowed to reach a size of 100-250 mm$^3$ before treatment is started. IL-10, PEG-mIL-10, PEG-hIL-10, or buffer control is administered subcutaneously at a site distant from the tumor implantation. Tumor growth is typically monitored twice weekly using electronic calipers.

Tumor tissues and lymphatic organs are harvested at various endpoints to measure mRNA expression for a number of inflammatory markers and to perform immunohistochemistry for several inflammatory cell markers. The tissues are snap-frozen in liquid nitrogen and stored at −80° C. Primary tumor growth is typically monitored twice weekly using electronic calipers. Tumor volume may be calculated using the formula (width$^2$×length/2) where length is the longer dimension. Tumors are allowed to reach a size of 90-250 mm$^3$ before treatment is started.

Administration of IL-10 and/or PEG-IL-10

The tumor models and tumor analysis methods described above were utilized to generate the data set forth hereafter. However, as alluded to above, these same models and methodologies may be used in other experimental settings.

Murine IL-10 (mIL-10) or PEG-mIL-10 were administered to the immunocompetent mice, while PEG-hIL-10 treatment was used in the B-cell deficient mice. Murine IL-10, PEG-mIL-10, PEG-hIL-10, or vehicle control was administered subcutaneously at a site distant from the tumor implant. PEG-mIL-10 used in these studies was prepared with the SC-PEG-12K linker. The biological activities of mIL-10 and PEG-m IL-10 were assessed by the application of a short-term proliferation bioassay that utilizes MC/9, a mouse mast cell line, which expresses endogenous mIL-10 receptors (R1 and R2). The MC/9 cells proliferate in response to co-stimulation with mIL-4 and mIL-10 (MC/9 cells do not proliferate with only mIL-4 or mIL-10). Proliferation was measured by colorimetric means using Alamar Blue, a growth indicator dye based on detection of metabolic activity. The biological activity of recombinant or PEG-mIL-10 was assessed by the EC50 value, or the concentration of protein at which half-maximal stimulation is observed in a dose-response curve (Table 1).

TABLE 1

MC/9 Proliferation bioassay for the assessment of bioactivity of mIL-10 and PEG-mIL10 reagents used in these studies

| Protein | EC50 (ng/mL) in MC/9 Assay |
| --- | --- |
| mIL-10 | 0.5711 |
| PEG-mIL-10 | 4.039 |

As indicated in Table 1, based on the MC/9 bioassay the specific activity of the PEG-mIL-10 used in the experiments is approximately 7-fold lower than the activity of the mIL-10.

PEG-mIL-10 may also be administered every second day to mice harboring Ep2 breast cancer tumors. Treatment was effective in reducing tumor size and inducing tumor rejections.

TABLE 2

PEG mIL-10 reduces tumor size (mm$^3$) in Ep2 breast cancer model in Balb/C mice.

| | Days after Inoculation | | | | | | |
| --- | --- | --- | --- | --- | --- | --- | --- |
| | 11 | 15 | 18 | 21 | 25 | 27 | 33 |
| Control | 300 | 450 | 500 | 750 | 1300 | 1500 | 2700 |
| PEG-IL-10 | 300 | 400 | 310 | 280 | 250 | 50 | 0 |

Treatment with PEG-mIL-10 was also effective in reducing tumor size in PDV6, CT-26, and 4T1 syngeneic immune competent mouse tumor models (see Tables 3, 4, and 5).

TABLE 3

Study 04-M52 338: PEG mIL-10 beginning day 36 after implant reduces PDV6 tumor size (mm$^3$) in C57B/6 mice..

| | Days after Inoculation | | | | | | |
| --- | --- | --- | --- | --- | --- | --- | --- |
| | 36 | 38 | 42 | 44 | 46 | 48 | 52 |
| Control | 200 | 255 | 290 | 380 | 395 | 420 | 485 |
| PEG-mIL-10 | 210 | 265 | 200 | 190 | 155 | 110 | 55 |

TABLE 4

PEG mIL-10 beginning day 7 after implant reduces tumor size relative to vehicle control of CT26 tumors (mm$^3$) in BALB/c mice.

| | Days after Inoculation | | | | | |
| --- | --- | --- | --- | --- | --- | --- |
| | 10 | 15 | 17 | 20 | 22 | 24 |
| Vehicle Control | 155 | 424 | 791 | 1274 | 1737 | 2170 |
| PEG-mIL-10 | 136 | 212 | 291 | 336 | 450 | 455 |

TABLE 5

IL-10 and PEG mIL-10 reduces tumor size (mm³) of 4T1 breast carcinoma

| Days of Treatment | 20 | 24 | 29 | 33 |
|---|---|---|---|---|
| Control | 200 | 410 | 584 | 1000 |
| PEG-mIL-10 | 200 | 320 | 560 | 350 |
| IL-10 | 200 | 290 | 575 | 400 |

Dose Titration Studies

In dose titration studies, tail-vein bleeds were collected from representative mice of each group at times corresponding to the expected peak and trough dose levels. Serum harvested was assayed for mIL-10 concentrations using the Meso Scale Discovery platform which is based on multi-array technology, a combination of electrochemiluminescence detection and patterned arrays. A two-tailed unpaired student t-test was used to compare the mean tumor volume of mIL-10 or PEG-mIL-10-treated mice grouped by serum mIL-10 concentration with the mean tumor volume of their corresponding vehicle control group. A Welch's correction was used when two groups had unequal variance (p<0.05 from t-test).

Dose titrations of PEG-mIL-10 and mIL-10 in 4T1 breast carcinoma-bearing mice show that control of primary tumor and lung metastases are dosetitratable with both mIL-10 and with PEG-mIL-10. As set forth in Table 6, at any given dose PEG-mIL-10 is more effective than mIL-10. Twice daily treatment was started on Day 17 after implant, when the mean tumor volumes were 84-90 mm³. Treatment groups consisted of 14 mice per group while the control groups had 8 mice in each group. Tris and Hepes buffers were the controls for mIL-10 and PEG mIL-10, respectively.

TABLE 6

Study 06-M175-1103. mIL-10 and PEG-mIL-10 reduce primary tumor size (mm³) of 4T1breast carcinoma in BALB/c mice in a dose-dependent manner.

| | Days after Implant | | | | | | | |
|---|---|---|---|---|---|---|---|---|
| | 17 | 21 | 24 | 27 | 30 | 34 | 38 | 42 |
| Tris Vehicle control | 90 | 184 | 288 | 448 | 560 | 861 | 1126 | 1248 |
| Hepes Vehicle control | 90 | 215 | 344 | 476 | 658 | 940 | 1261 | 1520 |
| PEG-mIL-10 (0.5 mg/kg) | 86 | 107 | 117 | 129 | 150 | 165 | 204 | 195 |
| PEG-mIL-10 (0.1 mg/kg) | 84 | 112 | 142 | 152 | 224 | 256 | 286 | 356 |
| PEG-mIL-10 (0.01 mg/kg) | 85 | 140 | 200 | 240 | 288 | 462 | 627 | 773 |
| PEG-mIL-10 (0.001 mg/kg) | 88 | 168 | 239 | 262 | 373 | 532 | 729 | 942 |
| mIL-10 (1.0 mg/kg) | 85 | 117 | 168 | 207 | 256 | 350 | 446 | 497 |
| mIL-10 (0.1 mg/kg) | 84 | 136 | 180 | 251 | 337 | 424 | 641 | 704 |
| mIL-10 (0.01 mg/kg) | 86 | 121 | 165 | 231 | 331 | 436 | 631 | 809 |

Dose titrations of PEG-mIL-10 and mIL-10 in PDV6 squamous cell carcinoma-bearing mice show that control of primary tumor is dosetitratable with both mIL-10 and with PEG-mIL-10, though at any given dose PEG-mIL-10 is more effective than mIL-10 (Table 7). The high dose PEG-mIL-10 treatment resulted in a near 100% tumor regression and subsequent resistance to re-challenge (Table 8). Twice daily treatment was started on Day 23 after implant, when the mean tumor volumes were 107-109 mm³ and continued through day 55 for all mIL10-treated groups and 0.01 mg/kg PEG mIL-10 treated group. The 0.1 mg/kg PEG-mIL-10 treatment was stopped on day 48 when 100% tumor regression was seen, while the remaining groups were treated until day 51. Treatment groups consisted of 10 mice per group while each vehicle control contained 6 mice. Tris buffer and Hepes buffer were the vehicle control for mIL-10 and PEG mIL-10, respectively. Re-implant was done 85 days after the primary implant and 4 weeks after the last PEG-mIL 10 treatment. There were 10 mice per group.

TABLE 7

Study 06-M52-1106. mIL-10 and PEG-mIL-10 reduce tumor size (mm³) of PDV6 squamous cell carcinoma in C57Bl6/J mice in a dose dependent manner.

| | Days after Implant | | | | | | | | | |
|---|---|---|---|---|---|---|---|---|---|---|
| | 23 | 27 | 30 | 33 | 36 | 40 | 43 | 47 | 51 | 55 |
| Tris Vehicle control | 111 | 179 | 232 | 318 | 412 | 493 | 635 | 848 | 958 | |
| Hepes Vehicle control | 107 | 210 | 293 | 433 | 541 | 653 | 712 | 761 | 986 | |
| PEG-mIL-10 (0.1 mg/kg) | 108 | 99 | 55 | 31 | 17 | 11 | 3 | 1 | 1 | 1 |
| PEG-mIL-10 (0.01 mg/kg) | 107 | 131 | 92 | 97 | 95 | 114 | 119 | 123 | 183 | 228 |
| PEG-mIL-10 (0.001 mg/kg) | 109 | 191 | 191 | 241 | 327 | 455 | 535 | | | |
| mIL-10 (1.0 mg/kg) | 107 | 129 | 144 | 143 | 124 | 87 | 51 | 36 | 52 | 75 |

TABLE 7-continued

Study 06-M52-1106. mIL-10 and PEG-mIL-10 reduce tumor size (mm³) of PDV6 squamous cell carcinoma in C57Bl6/J mice in a dose dependent manner.

| | Days after Implant | | | | | | | | | |
|---|---|---|---|---|---|---|---|---|---|---|
| | 23 | 27 | 30 | 33 | 36 | 40 | 43 | 47 | 51 | 55 |
| mIL-10 (0.1 mg/kg) | 107 | 85 | 85 | 88 | 117 | 121 | 130 | 143 | 182 | 217 |
| mIL-10 (0.01 mg/kg) | 107 | 120 | 150 | 146 | 196 | 244 | 262 | 263 | 249 | 250 |

TABLE 8

Study 06-M52-1106. C57Bl/6J mice that have cleared PDV6 squamous cell carcinoma tumors after 3 weeks of PEG-mIL-10 treatment are resistant to re-implant in the absence of additional treatment.

| | Days after Implant | | | | | | % mice that are tumor positive |
|---|---|---|---|---|---|---|---|
| | 0 | 16 | 21 | 28 | 36 | 49 | |
| Vehicle Control | 0 | 113 | 145 | 188 | 418 | 761 | 100 |
| PEG-mIL-10 (0.1 mg/kg) | 0 | 0.3 | 0 | 7 | 16 | 47 | 10 |

Lung Metastasis Studies

Lung metastases in the 4T1 breast carcinoma model were either quantified macroscopically after lung resection (Table 9) or by counting the lung metastatic colonies after culture (Table 10) as described in Current Protocols in Immunology (Section 20.2.4) John Wiley and Sons, Inc., New York; Harlow and Lane (1999). Briefly, lungs harvested from a 4T1 tumor-bearing mouse were minced and digested with a collagenase/elastase cocktail followed by culture in a limiting dilution assay, in medium containing 6-thioguanine. Only 4T1 cells are 6-thioguanine-resistant and can be quantified by counting the number of colonies after 10-14 days of culture. Twice daily treatment was started on Day 17 after implant, when the mean tumor volumes were 84-90 mm³. Tris and Hepes buffers were the controls for mIL-10 and PEG mIL-10, respectively. Lung metastases were measured as the number of metastatic colonies cultured per lung.

TABLE 9

Study 05-M52-496. 2 week treatment with mIL-10 and PEG-mIL-10 beginning 19 days after implant reduces metastasis of 4T1 breast carcinoma (measured as number of lung metastases per mouse)

| | Lung Metastasis 33 days after Inoculation | | |
|---|---|---|---|
| | Vehicle Control | mIL-10 | PEG-mIL-10 |
| Mouse #1 | 7 | 0 | 0 |
| Mouse #2 | 7 | 0 | 0 |
| Mouse #3 | 7 | 0 | 0 |
| Mouse #4 | 8 | 0 | 0 |
| Mouse #5 | 20 | 4 | 0 |

TABLE 10

Study 06-M175-1103. mIL-10 and PEG-mIL-10 reduce lung metastases of 4T1 breast carcinoma in BALB/c mice in a dose-dependent manner.

| | Lung Metastases 42-45 days after Implant Colonies per lung (×10³) | | | | | | | | |
|---|---|---|---|---|---|---|---|---|---|
| Mouse | Tris buffer vehicle control | Hepes buffer vehicle control | mIL-10 1.0 mg/kg | mIL-10 0.1 mg/kg | mIL-10 0.01 mg/kg | PEG-mIL-10 0.5 mg/kg | PEG-mIL-10 0.1 mg/kg | PEG-mIL-10 0.01 mg/kg | PEG-mIL-10 0.001 mg/kg |
| 1 | 362 | 481 | 76 | 116 | 1064 | 7.1 | 89 | 0.43 | 366 |
| 2 | 2.12 | 533 | 20 | 5.6 | 150 | 1.0 | 0.7 | 234 | 212 |
| 3 | 152 | 264 | 28.1 | 8.1 | 67.4 | 0.4 | 0.01 | 377 | 0.6 |
| 4 | 0.4 | 218 | 1.2 | 137 | 18 | 1.5 | 223 | 315 | 586 |
| 5 | 1000 | 517 | 45.7 | 257 | 77 | 0.3 | 0.07 | 0.54 | 486 |
| 6 | 474 | 93 | 21.7 | 2.72 | 1.2 | 0.02 | 10.1 | 1.67 | 844 |
| 7 | 524 | 1000 | 4.4 | 364 | 285 | 0 | 7.6 | 68 | 6.5 |
| 8 | 1000 | 1026 | 128.6 | 772 | 9.7 | 0.002 | 1.85 | 27 | 265 |
| 9 | | | 13.3 | 348 | 878 | 0.3 | 0.01 | 139 | 338 |
| 10 | | | 51.2 | 204 | 45 | 0.03 | 0.01 | 177 | 824 |
| 11 | | | 9.4 | 49 | 56 | 0.01 | 2.68 | 597 | 263 |
| 12 | | | 0.1 | 635 | 17.1 | 240 | 0.01 | 7.4 | |
| 13 | | | 5.1 | 19.7 | 1014 | 0.02 | 2.94 | 0.01 | |
| 14 | | | 0.02 | 750 | 72.2 | 0.01 | 0.01 | 0.01 | |
| Median | 418.0 | 499.0 | 16.7 | 170.5 | 69.8 | 0.17 | 1.28 | 47.5 | 338.0 |
| Mean | 502.0 | 579.0 | 28.9 | 262.0 | 268.2 | 17.9 | 24.1 | 138.9 | 381.0 |
| S.D. | 519.0 | 467.0 | 36.5 | 276.9 | 397.1 | 64.0 | 61.8 | 183.7 | 284.0 |

Administering PEG-mIL-10 or IL-10 to 4T1 breast carcinoma-bearing mice reduces the rate of metastasis and increases CD8+ T-cell infiltration and expression of immune stimulatory cytokines, as measured by quantitative RT-PCR (Tables 11 and 12). The number of infiltrating CD8+ T-cells was counted from representative sections of several tumors stained by immunohistochemistry for the CD8 surface marker and verified by staining with anti-CD3 and anti-TCRαβ antibodies.

TABLE 11

IL-10 and PEG mIL-10 induce CD8+
T-cell infiltration in 4T1 carcinoma

|  | control | IL-10 | PEG-IL-10 |
|---|---|---|---|
| Average Number of CD8+ Cells/Field | 6.4 | 25.8 | 39.2 |

PEG-mIL-10 is more effective than IL-10 in the induction of inflammatory cytokines. Total RNA from homogenized tumor samples was extracted and reverse-transcribed as previously described (see, e.g., Homey, et al. (2000) J. Immunol. 164:3465-3470). Complementary DNA was quantitatively analyzed for expression of cytokines by the fluorgenic 5'-nuclease PCR assay (see, e.g., Holland, et al. (1991) Proc. Natl. Acad. Sci. 88:7276-7280). Specific PCR products were continuously measured by means of an ABI PRISM 7700 Sequence Detection System (Applied Biosystems) during 40 cycles. Values were normalized to ubiquitin. Log-transformed data were subjected to Kruskal-Wallis statistical analysis (median method). The expression level (log transformed) corresponds to the amount of inflammatory cytokine expressed in the tumor sample, such that the higher the expression level (log transformed), the greater the amount of inflammatory cytokine expressed in the tumor sample.

TABLE 12

Administered PEG-mIL-10 induces sustained levels of inflammatory
cytokines in 4T1 carcinoma 24 h after dose administration.

| Cytokine | control | IL-10 | PEG-mIL-10 |
|---|---|---|---|
| IFNγ | 36.04 | 68.51 | 98.96 |
| IL-4 | 7.77 | 13.13 | 40.32 |
| IL-6 | 43.64 | 50.59 | 111.98 |
| IL-10 | 9.94 | 41.62 | 106.16 |
| RANK-Ligand | 19.14 | 36.13 | 46.08 |

Depletion of Immune Cells

CD4+ and CD8+ T-cells were depleted by antibody-mediated elimination. 250 μg of CD4- or CD8-specific antibodies were injected weekly for this purpose. Cell depletions were verified using FACS and IHC analysis.

Depletion of CD4+ T cells in B cell deficient BALB/c mice (C.129-Igh-6$^{tm1Cgn}$) with CD4 antibodies inhibits PEG-hIL-10 function on tumors (Table 13).

TABLE 13

PEG-hIL-10 treatment beginning 8 days after tumor implant fails
to reduce tumor size (mm³) of CT-26 colon carcinoma after CD4 depletion
in B cell deficient BALB/c mice (C.129-Igh-6$^{tm1Cgn}$).

| Days after Implant | 8 | 10 | 13 | 19 | 27 |
|---|---|---|---|---|---|
| PBS | 173 | 322 | 391 | 841 | 1979 |
| PEG-hIL-10 | 184 | 276 | 251 | 602 | 1332 |

Depletion of CD8+ T-cells completely inhibits the effect of PEG mIL-10 on syngeneic tumor growth (Table 14).

TABLE 14

PEG-hIL-10 treatment beginning 8 days after tumor implant
fails to reduce tumor size (mm³) of CT-26 colon carcinoma
after CD8 depletion in B cell deficient BALB/c mice.

| Days after Implant | 8 | 10 | 13 | 19 | 27 |
|---|---|---|---|---|---|
| PBS | 151 | 335 | 584 | 1434 | 2746 |
| PEG-hIL-10 | 226 | 575 | 1047 | 2449 | 4799 |

IL-10 Dosing Frequency and Serum Trough Concentration

Murine studies were designed and performed in order to enhance understanding of the pharmacokinetic parameters of IL-10 therapy and to generate data in mice useful in optimizing the tumor treatment regimens for recombinant human IL-10 (rhIL-10) in human subjects.

Mice were inoculated with PDV6 tumor cells, and tumors were allowed to grow for 2.5 weeks to reach 100 mm³. Groups of tumor-bearing mice (n=10/group) were then treated with identical weekly doses (0.7 mg/kg/week), administering 5 kDa mono-di PEGmIL-10 as a) one bolus SC injection once a week, or b) several SC injections in divided doses throughout the week, including twice weekly (0.35 mg/kg), every second day (~0.25 mg/kg, such that the total weekly dose=0.7 mg/kg), and daily (0.1 mg/kg/day). As all mice received the same amount of drug over the course of a week, similar overall exposures (Area Under the Curve, AUC) were observed. The peak exposure was highest in the once-weekly dosed animals, while the minimum drug exposure (trough) was highest in the mice receiving smaller, daily doses. Surprisingly, as indicated in Table 15, animals dosed daily exhibited the highest anti-tumor efficacy, indicating that the serum trough exposure was important for anti-tumor function, while the influence of the peak exposure on anti-tumor function was not determinative.

TABLE 15

| Dosing Schedule | Tumor Size (mm³) |
|---|---|
| Control | 813.9522 |
| Daily | 43.196 |
| Every second day | 170.186 |
| Bi-weekly | 347.315 |
| Weekly | 425.572 |

The required serum trough concentration was further explored in two tumor models: PDV6 tumors in C57BL/6 mice and CT26 colon cancer cells in Balb/C mice. Utilizing standard procedures, mice were allowed to grow to 100 mm³, and treatment was then initiated with administration of 5 kDa mono-di PEGmIL-10 for 4 weeks. Thereafter, the serum trough concentrations of IL-10 were measured in tumor-bearing mice receiving different treatment schedules. The IL-10 serum trough concentrations were then correlated with the resulting tumor size. As indicated in Table 16, mice with a serum trough of IL-10 over 1 ng/mL had consistently small tumors and rejected their tumors.

TABLE 16

| IL-10 serum trough Range [pg/ml] | IL-10 serum trough (Mean) [pg/ml] | Tumor size (Mean) [mm3] | Tumor weight (Mean) [g] |
|---|---|---|---|
| 30-73 | 47 | 846 | 1.1 |
| 105-246 | 164 | 610 | 0.7 |

TABLE 16-continued

| IL-10 serum trough Range [pg/ml] | IL-10 serum trough (Mean) [pg/ml] | Tumor size (Mean) [mm3] | Tumor weight (Mean) [g] |
|---|---|---|---|
| 250-629 | 433 | 570 | 0.6 |
| 1155-2095 | 1619 | 148 | 0.2 |

Figure 2B:
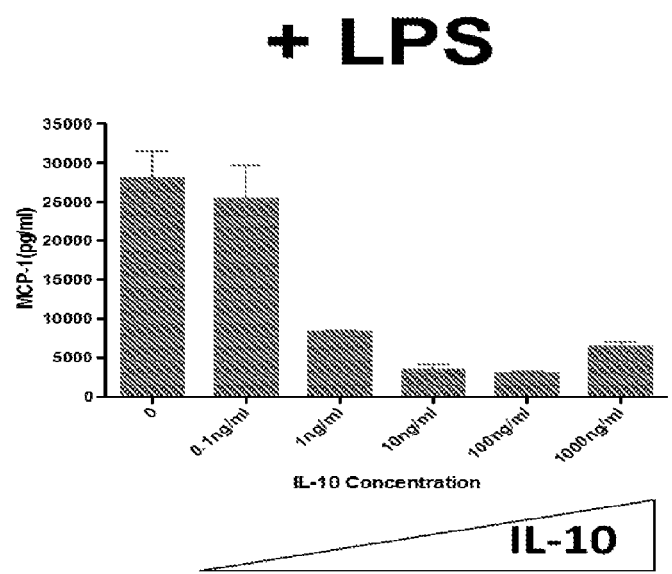
FIG. 2B depicts the concentration of MCP-1 (pg/mL) in PBMCs stimulated with LPS at increasing concentrations of IL-10. IL-10 is an inhibitor of LPS-mediated activation of PBMCs, and the addition of IL-10 at concentrations of 1 ng/mL and above significantly inhibited the secretion of MCP-1.

To confirm the critical trough concentration in human cells, hIL-10 was added at increasing concentrations to cultures of human peripheral blood monocyte cells (PB-MCs). The PBMC cultures were left untreated or stimulated with lipopolysaccharide (LPS). IL-10 is known to inhibit the LPS-mediated activation of PBMCs. Activity was measured as the secretion of the chemokine MCP-1. Both LPS and IL-10 induce the secretion of MCP-1, but inhibit each others' activity in inducing the chemokine. At concentrations of 1 ng/mL and above, IL-10 increased the secretion of MCP-1 in the absence of LPS (FIG. 2A). In contrast, in PBMCs stimulated with LPS, addition of IL-10 at a concentration of 1 ng/mL significantly inhibited the secretion of MCP-1 (FIG. 2B). This confirmed the biological activity of IL-10 for both the induction and the inhibition of respective biological processes.

Effect of IL-10 on Cytokines and Cholesterol in Human Subjects

Determination of Serum IL-10 Concentrations in Human Subjects.

Human volunteers were administered the desired amount of rhIL-10 SC or IV, and whole blood samples were drawn into heparin anticoagulant-containing vessels at desired time(s) post-administration. Serum rhIL-10 or PEG-rhIL-10 concentrations were determined using a standard sandwich enzyme-linked immune absorbent assay (ELISA) kit. Typically, the ELISA assay was determined to be selective, linear and reproducible in the concentration range of 0.1 to 10 ng/mL, and the limit of quantitation (LOQ) was 0.1 ng/mL. Serum samples were also analyzed by an ELISA for the presence of antibodies that bind hIL-10. In addition, selected serum samples were analyzed using a validated bioassay comprising the mouse mast cell line MC9; this cell line proliferates in response to IL-10. The bioassay was used to determine the bioactivity of GMP-produced rHuIL-10 and PEG-rHuIL-10 and to determine the biological activity of the IL-10 in patient serum. Typically, ELISA and Bioassay determinations of IL-10 concentration and activity revealed corresponding values.

Determination of TNFα and IL-1β Concentrations in Human Subjects.

IL-10 has anti-inflammatory function in patients suffering from chronic inflammatory diseases, and TNFα and IL-1β represent the key inflammatory cytokines released in such diseases. TNFα and IL-1β concentrations were determined in blood samples obtained from human subjects. Typically, 3 mL of venous blood was aseptically collected just prior to SC or IV administration (0 hour) of rhIL-10 and at 0.5, 2, 3, 4, 6, 8, 12, 16, 24, 48, 72 and 96 hours post-dose. The samples were subjected to a whole blood cytokine release assay in the presence of LPS and an anticoagulant, and TNFα and IL-1β concentrations were measured with an ELISA assay. LPS stimulated the release of TNFα and IL-1β from blood cells.

In samples collected 0.5-12 hours after individuals were dosed IV with rHuIL-10, the release of TNFα and IL-1β was inhibited. In samples collected from individuals dosed SC with rHuIL-10, the release of TNFα and IL-1β was inhibited from 0.5 hours to 24 hours. The serum concentration of rHuIL-10 in those human subjects was determined by ELISA. The inhibition of TNFα and IL-1β correlated with the serum concentration of rHuIL-10. The serum concentration of rHuIL-10 increased after dosing and remained elevated for 48 hours. However, the release of TNFα and IL-1β was inhibited only as long as the concentration of rHuIL-10 was at or above 0.2 ng/mL; the release of TNFα and IL-1β was not inhibited when the concentration was below 0.1 ng/mL. After 12 h following IV dosing of rHuIL-10 and after 24 h following SC dosing, the serum concentration dropped below 0.2 ng/mL and the release of TNFα and IL-1β was observed. These data indicate that it is necessary to achieve an IL-10 serum trough concentration at or above 0.2 ng/mL in or to observe an anti-inflammatory function in patients suffering from chronic inflammatory diseases.

Determination of INFγ and Cholesterol Modulation by PEG-IL-10 in Human Cancer Patients.

IL-10 induces IFNγ in CD8+T cells, and IFNγ induction is essential for IL-10-mediated tumor rejection in mice. IFNγ-deficient mice failed to reject their tumors when treated with PEG-mIL-10 at concentrations inducing tumor resolution in control mice (data not shown). IFNγ was therefore measured in the serum of patients treated with PEG-rhIL-10.

After education regarding appropriate administration techniques, cancer patients self-injected PEG-rhIL-10 SC daily at various doses. Serum IL-10 concentrations were determined using a sandwich ELISA as previously described. IFNγ was measured using a Luminex bead assay (Luminex Corp.; Austin, Tex.) in serum samples taken prior to the first dose or after 28 days of dosing.

As indicated in Table 17, patients receiving 1 µg/kg PEG-IL-10 had serum trough levels between ~0.4 and ~1.1 ng/mL IL-10, while patients receiving 2.5 µg/kg PEG-IL-10 doses had serum trough levels between ~0.4 and ~2.6 ng/mL of IL-10.

IFNγ signals primarily through the Jak-Stat pathway. Jak-Stat signaling involves sequential receptor recruitment and activation of members of the Janus family of kinases (Jaks: Jaks 1-3 and Tyk2) and the Stats (Stats 1-6, including Stat5a and Stat5b) to control transcription of target genes via specific response elements. As this signaling mechanism is a characteristic of many members of the cytokine receptor superfamily, IFNγ-induced Jak-Stat signaling is the current paradigm for class II cytokine receptor signal transduction. As indicated in Table 17, patients having serum trough levels of 1 ng/mL or greater showed an induction of IFNγ in the serum, while patients who had serum trough levels below 1 ng/mL failed to show induction of IFNγ. Referring to Table 17, IFNγ induction is defined as a value greater than 1.

TABLE 17

| Patient | 01 | 02 | 03 | 04 | 05 |
|---|---|---|---|---|---|
| Dose (µg/kg PEG-rHuIL-10) | 1 | 1 | 2.5 | 2.5 | 2.5 |
| Serum Trough (ng/mL) | 0.392 | 1.11 | 2.64 | 0.42 | 1.84 |
| IFNγ Induction | 0.55 | 1.35 | 2.4 | 0.97 | 11.2 |

These data indicate that it is necessary to achieve an IL-10 serum trough concentration at or above 1 ng/mL in or to observe a therapeutic effect in the cancer/tumor setting. Importantly, the serum trough concentration was the determining factor for IFNγ induction, not the dose level.

Cholesterol was measured in serum samples drawn from cancer patients prior to administration of PEG-rhIL-10 or after one week of daily SC dosing (1 μg/kg; 2.5 μg/kg; or 5 μg/kg; n=3-4 patients/dose). Referring to Table 18, patients receiving 1 μg/kg achieved an average daily serum cholesterol concentration of 0.4 ng/mL and had a 7.8% reduction in cholesterol; the patient receiving 2.5 μg/kg achieved an average daily serum cholesterol concentration of 1 ng/mL and had a 19% reduction in cholesterol; and the patient receiving 5 μg/kg achieved an average serum trough cholesterol concentration of 2 ng/mL and had a 38% reduction in cholesterol. Thus, each of the dosing regimens resulted in a therapeutically relevant reduction in serum cholesterol, indicating that average IL-10 serum trough concentrations of approximately 0.2 ng/mL to 0.4 ng/mL were efficacious.

TABLE 18

| Dose | 1 ug/kg | 2.5 | 5 |
| --- | --- | --- | --- |
| n | 4 | 4 | 3 |
| Avg. Serum Trough (day 15) | 0.4 | 1.8 | 3.6 |
| Avg. Cholesterol Reduction (1 week) | 7.8% | 20% | 37% |

Particular embodiments of this invention are described herein, including the best mode known to the inventors for carrying out the invention. Upon reading the foregoing, description, variations of the disclosed embodiments may become apparent to individuals working in the art, and it is expected that those skilled artisans may employ such variations as appropriate. Accordingly, it is intended that the invention be practiced otherwise than as specifically described herein, and that the invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All publications, patent applications, accession numbers, and other references cited in this specification are herein incorporated by reference as if each individual publication or patent application were specifically and individually indicated to be incorporated by reference.

What is claimed is:

1. A method of treating cancer in a human subject, comprising administering to the human subject a therapeutically effective amount of a PEG-IL-10 agent sufficient to maintain an IL-10 serum trough concentration of the PEG-IL-10 agent in the human subject at or above 1 ng/ml over a period of time of at least one week; wherein said administering treats cancer in the human subject.

2. The method of claim 1, wherein the PEG-IL-10 agent comprises mature human IL-10.

3. The method of claim 1, wherein the PEG-IL-10 agent comprises a variant of mature human IL-10, and wherein the variant exhibits activity comparable to the activity of mature human IL-10.

4. The method of claim 1, wherein the PEG-IL-10 agent comprises at least one PEG molecule covalently attached to at least one amino acid residue of at least one subunit of mature human IL-10.

5. The method of claim 1, wherein the PEG-IL-10 agent comprises a mixture of mono-pegylated and di-pegylated IL-10.

6. The method of claim 1, wherein the PEG component of the PEG-IL-10 agent has a molecular mass from about 5 kDa to about 20 kDa.

7. The method of claim 1, wherein the PEG component of the PEG-IL-10 agent has a molecular mass greater than about 20 kDa.

8. The method of claim 4, wherein at least one PEG molecule is covalently attached to at least one IL-10 subunit via a linker.

9. The method of claim 1, wherein the PEG-IL-10 agent is administered to the subject at least once daily.

10. The method of claim 1, further comprising administering at least one additional prophylactic or therapeutic agent.

11. The method of claim 1, wherein the IL-10 serum trough concentration is at least 1.25 ng/mL.

12. The method of claim 1, wherein the IL-10 serum trough concentration is at least 1.75 ng/mL.

13. The method of claim 1, wherein the PEG-IL-10 agent is administered to maintain an IL-10 serum trough concentration at or above 1 ng/ml is maintained over a period of time of at least two weeks.

14. The method of claim 1, wherein the PEG-IL-10 agent is administered to maintain an IL-10 serum trough concentration at or above 1 ng/ml is maintained over a period of time of at least one month.

15. The method of claim 1, wherein said administering is subcutaneous.

16. The method of claim 15, wherein said administering is once daily.

* * * * *